(12) United States Patent
Palani et al.

(10) Patent No.: US 8,283,360 B2
(45) Date of Patent: Oct. 9, 2012

(54) BICYCLIC HETEROCYCLIC DERIVATIVES AND METHODS OF USE THEREOF

(75) Inventors: Anandan Palani, Bridgewater, NJ (US); Ashwin U. Rao, Avenel, NJ (US); Xiao Chen, Edison, NJ (US); Ning Shao, Clark, NJ (US); Ying R. Huang, Berkeley Heights, NJ (US); Robert G. Aslanian, Rockaway, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/139,656

(22) PCT Filed: Dec. 18, 2009

(86) PCT No.: PCT/US2009/068774
§ 371 (c)(1),
(2), (4) Date: Jun. 14, 2011

(87) PCT Pub. No.: WO2010/071819
PCT Pub. Date: Jun. 24, 2010

(65) Prior Publication Data
US 2011/0319434 A1 Dec. 29, 2011

Related U.S. Application Data

(60) Provisional application No. 61/139,071, filed on Dec. 19, 2008.

(51) Int. Cl.
*A61K 31/437* (2006.01)
*C07D 498/04* (2006.01)
(52) U.S. Cl. ......... 514/301; 514/302; 546/114; 546/115
(58) Field of Classification Search .................. 546/198; 514/357
See application file for complete search history.

(56) References Cited

U.S. PATENT DOCUMENTS

2005/0256310 A1 11/2005 Hulin et al.

FOREIGN PATENT DOCUMENTS

| WO | WO2006097691 | 9/2006 |
| WO | WO2007080191 | 7/2007 |
| WO | WO2008012010 | 1/2008 |

OTHER PUBLICATIONS

West, Anthony R., Solid State Chemistry and its Applications, Wiley, New York, 1988, pp. 358 & 365.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Patani et. al., "Bioisosterism: A Rational Approach in Drug Design", Chem. Rev. 1996, 96, 3147-3176.*

* cited by examiner

*Primary Examiner* — Zinna Northington Davis
(74) *Attorney, Agent, or Firm* — J. Eric Thies; Gerard M. Devlin

(57) ABSTRACT

The present invention relates to novel Bicyclic Heterocyclic Derivatives, pharmaceutical compositions comprising the Bicyclic Heterocyclic Derivatives and the use of these compounds for treating or preventing treating allergy, an allergy-induced airway response, congestion, a cardiovascular disease, an inflammatory disease, a gastrointestinal disorder, a neurological disorder, a cognitive disorder, a metabolic disorder, obesity or an obesity-related disorder, diabetes, a diabetic complication, impaired glucose tolerance or impaired fasting glucose.

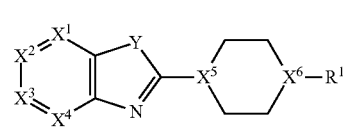

(I)

2 Claims, No Drawings

BICYCLIC HETEROCYCLIC DERIVATIVES AND METHODS OF USE THEREOF

CROSS REFERENCE TO RELATED APPLICATIONS

This application is a U.S. National Phase application under 35 U.S.C. §371 of PCT Application No. PCT/US2009/068774 filed Dec. 18, 2009, which claims priority under 35 U.S.C. §119(e) from U.S. Ser. No. 61/139,071, filed Dec. 19, 2008.

FIELD OF THE INVENTION

The present invention relates to novel Bicyclic Heterocyclic Derivatives, pharmaceutical compositions comprising the Bicyclic Heterocyclic Derivatives and the use of these compounds for treating or preventing treating allergy, an allergy-induced airway response, congestion, a cardiovascular disease, an inflammatory disease, a gastrointestinal disorder, a neurological disorder, a cognitive disorder, a metabolic disorder, obesity or an obesity-related disorder, diabetes, a diabetic complication, impaired glucose tolerance or impaired fasting glucose.

BACKGROUND OF THE INVENTION

The histamine receptors, $H_1$, $H_2$ and $H_3$ are well-identified forms. The $H_1$ receptors are those that mediate the response antagonized by conventional antihistamines. $H_1$ receptors are present, for example, in the ileum, the skin, and the bronchial smooth muscle of humans and other mammals. Through $H_2$ receptor-mediated responses, histamine stimulates gastric acid secretion in mammals and the chronotropic effect in isolated mammalian atria.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilation.

Imidazole $H_3$ receptor antagonists are well known in the art. More recently, non-imidazole $H_3$ receptor antagonists have been disclosed in U.S. Pat. Nos. 6,720,328 and 6,849,621.

U.S. Pat. No. 5,869,479 discloses compositions for the treatment of the symptoms of allergic rhinitis using a combination of at least one histamine $H_1$ receptor antagonist and at least one histamine $H_3$ receptor antagonist.

Diabetes refers to a disease process derived from multiple causative factors and is characterized by elevated levels of plasma glucose, or hyperglycemia in the fasting state or after administration of glucose during an oral glucose tolerance test. Persistent or uncontrolled hyperglycemia is associated with increased and premature morbidity and mortality. Abnormal glucose homeostasis is associated with alterations of the lipid, lipoprotein and apolipoprotein metabolism and other metabolic and hemodynamic disease. As such, the diabetic patient is at an especially increased risk of macrovascular and microvascular complications, including coronary heart disease, stroke, peripheral vascular disease, hypertension, nephropathy, neuropathy, and retinopathy. Accordingly, therapeutic control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce lithe or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissue (muscle, liver and adipose tissue), and the plasma insulin levels, while elevated, are insufficient to overcome the pronounced insulin resistance.

Insulin resistance is not associated with a diminished number of insulin receptors but rather to a post-insulin receptor binding defect that is not well understood. This resistance to insulin responsiveness results in insufficient insulin activation of glucose uptake, oxidation and storage in muscle, and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic [beta]-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a class of agents that can increase insulin sensitivity and bring about some degree of correction of hyperglycemia. However, the biguanides can induce lactic acidosis and nausea/diarrhea.

The glitazones (i.e. 5-benzylthiazolidine-2,4-dioses) are a separate class of compounds with potential for the treatment of type 2 diabetes. These agents increase insulin sensitivity in muscle, liver and adipose tissue in several animal models of type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of type 2 diabetes are agonists of the alpha, gamma or delta subtype, or a combination of these, and in many cases are chemically different from the glitazones (i.e., they are not thiazolidinediones). Serious side effects (e.g. liver toxicity) have been noted in some patients treated with glitazone drugs, such as troglitazone.

Additional methods of treating the disease are currently under investigation. New biochemical approaches include treatment with alpha-glucosidase inhibitors (e.g. acarbose) and protein tyrosine phosphatase-1B (PTP-1B) inhibitors.

Compounds that are inhibitors of the dipeptidyl peptidase-IV enzyme are also under investigation as drugs that may be useful in the treatment of diabetes, and particularly type 2 diabetes.

Despite a widening body of knowledge concerning the treatment of diabetes, there remains a need in the art for small-molecule drugs with increased safety profiles and/or improved efficacy that are useful for the treatment of diabetes and related metabolic diseases. This invention addresses that need.

SUMMARY OF THE INVENTION

In one aspect, the present invention provides Compounds of Formula (I) (also referred to herein as the "Bicyclic Heterocyclic Derivatives"):

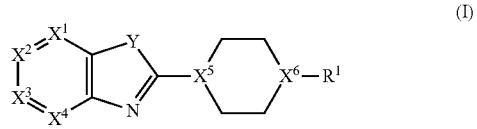

(I)

and pharmaceutically acceptable salts, solvates, esters and prodrugs thereof, wherein:

each occurrence of W is independently a bond, alkylene, —O—, —CH(OH)—, —C(O)—, —NHC(O)—, —C(O)NH—, —NHS(O)$_2$—, —S(O)$_2$NH— or —NH—;

each occurrence of Q is independently is H, halo, alkyl, alkenyl, alkynyl, aryl, cycloalkyl, heterocycloalkyl, heterocycloalkenyl, heteroaryl, haloalkyl, -alkylene-aryl, —OH, —NO$_2$ or —CN, wherein a aryl, cycloalkyl, heterocycloalkyl, heterocycloalkenyl or heteroaryl group can be optionally substituted with $R^2$;

$X^1$, $X^2$, $X^3$ and $X^4$ are each independently —N— or —C(—W-Q)-, such that at least one of $X^1$, $X^2$, $X^3$ and $X^4$ is —N—;

$X^5$ and $X^6$ are each independently —N—, —N-oxide- or —CH—;

Y is —O—, —S—, —S(O)—, —S(O)$_2$— or —N—;

$R^1$ is cycloalkyl, cycloalkenyl, heterocycloalkyl or heterocycloalkenyl, any of which can be unsubstituted or substituted with $R^2$, such that when $R^1$ is heterocycloalkyl or heterocycloalkenyl and $X^6$ is N, then $R^1$ is joined to $X^6$ via a ring carbon atom;

each occurrence of $R^2$ represents up to 3 substituents, which can be the same or different, and are selected from halo, alkyl, —OR$^3$, —N(R$^3$)$_2$—, —CN, —NO$_2$, —NHC(O)-alkyl, —C(O)N(R$^3$)$_2$, heteroaryl, haloalkyl, alkenyl, —C(O)—R$^3$ or hydroxyalkyl; and each occurrence of $R^3$ is independently H, alkyl, aryl, cycloalkyl, heterocycloalkyl or heteroaryl.

The Compounds of Formula (I) and pharmaceutically acceptable salts, solvates, prodrugs and esters thereof can be useful for treating or preventing allergy, an allergy-induced airway response, congestion, a cardiovascular disease, an inflammatory disease, a gastrointestinal disorder, a neurological disorder, a cognitive disorder, a metabolic disorder, obesity or an obesity-related disorder, diabetes, a diabetic complication, impaired glucose tolerance or impaired fasting glucose (each being a "Condition") in a patient.

Also provided by the invention are methods for treating or preventing Condition in a patient, comprising administering to the patient an effective amount of one or more compounds of Formula (I).

In addition, the present invention provides methods for treating or preventing Condition in a patient, comprising administering to the patient one or more Compounds of Formula (I) and an additional therapeutic agent that is not a Compound of Formula (I), wherein the amounts administered are together effective to treat or prevent the Condition.

The present invention further provides pharmaceutical compositions comprising an effective amount of one or more compounds of Formula (I) or a pharmaceutically acceptable salt, solvate thereof, and a pharmaceutically acceptable carrier. The compositions can be useful for treating or preventing a Condition in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "obesity" as used herein, refers to a patient being overweight and having a body mass index (BMI) of 25 or greater. In one embodiment, an obese patient has a BMI of about 25 or greater. In another embodiment, an obese patient has a BMI of between about 25 and about 30. In another embodiment, an obese patient has a BMI of between about 35 and about 40. In still another embodiment, an obese patient has a BMI greater than 40.

The term "obesity-related disorder" as used herein refers to: (i) disorders which result from a patient having a BM of about 25 or greater; and (ii) eating disorders and other disorders associated with excessive food intake. Non-limiting examples of an obesity-related disorder include edema, shortness of breath, sleep apnea, skin disorders and high blood pressure.

The term "metabolic syndrome" as used herein, refers to a set of risk factors that make a patient more succeptible to cardiovascular disease and/or type 2 diabetes. As defined herein, a patient is considered to have metabolic syndrome if the patient has one or more of the following five risk factors:
1) central/abdominal obesity as measured by a waist circumference of greater than 40 inches in a male and greater than 35 inches in a female;
2) a fasting triglyceride level of greater than or equal to 150 mg/dL;
3) an HDL cholesterol level in a male of less than 40 mg/dL or in a female of less than 50 mg/dL;
4) blood pressure greater than or equal to 130/85 mm Hg; and
5) a fasting glucose level of greater than or equal to 110 mg/dL.

The term "impaired glucose tolerance" as used herein, is defined as a two-hour glucose level of 140 to 199 mg per dL (7.8 to 11.0 mmol) as measured using the 75-g oral glucose tolerance test. A patient is said to be under the condition of impaired glucose tolerance when he/she has an intermediately raised glucose level after 2 hours, wherein the level is less than would qualify for type 2 diabetes mellitus.

The term "impaired fasting glucose" as used herein, is defined as a fasting plasma glucose level of 100 to 125 mg/dL; normal fasting glucose values are below 100 mg per dL.

The term "upper airway" as used herein, refers to the upper respiratory system—i.e., the nose, throat, and associated structures.

The term "effective amount" as used herein, refers to an amount of compound of formula I and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

The term "alkyl," as used herein, refers to an aliphatic hydrocarbon group which may be straight or branched and which contains from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkyl, aryl, cycloalkyl, cyano, hydroxy, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is unsubstituted. In another embodiment, an alkyl group is linear. In another embodiment, an alkyl group is branched.

The term "alkenyl," as used herein, refers to an aliphatic hydrocarbon group containing at least one carbon-carbon double bond and which may be straight or branched and contains from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkyl, aryl, cycloalkyl, cyano, —O-alkyl, and —S(alkyl). In one embodiment, an alkenyl group is unsubstituted.

The term "alkynyl," as used herein, refers to an aliphatic hydrocarbon group containing at least one carbon-carbon triple bond and which may be straight or branched and contains from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of alkyl, aryl and cycloalkyl. In one embodiment, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$— and —CH$_2$CH(CH$_3$)CH$_2$—. An alkylene group may be unsubstituted or substituted by one or more substituents which may be the same or different, each substituent being independently selected from the group consisting of halo, alkyl, aryl, cycloalkyl, cyano, —O-alkyl, and —S(alkyl). In one embodiment, an alkylene group is unsubstituted. In another embodiment, an alkylene group has from 1 to about 6 carbon atoms. In another embodiment, an alkylene group is branched. In still another embodiment, an alkylene group is linear.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH$_2$CH=CH—, —CH$_2$CH=CHCH$_2$—, —CH=CHCH$_2$CH$_2$—, —CH$_2$CHCH=CH—, —CH(CH$_3$)CH=CH— and —CH=C(CH$_3$)CH$_2$—. In one embodiment, an alkenylene group has from 2 to about 6 carbon atoms. In another embodiment, an alkenylene group is branched. In another embodiment, an alkenylene group is linear.

The term "alkynylene," as used herein, refers to an alkynyl group, as defined above, wherein one of the alkynyl group's hydrogen atoms has been replaced with a bond. Non-limiting examples of alkynylene groups include —C≡C—, —CH$_2$C≡C—, —CH$_2$C≡CCH$_2$—, —C≡CCH$_2$CH$_2$—, —CH$_2$CHC≡C—, —CH(CH$_3$)C≡C— and —C≡CCH$_2$—. In one embodiment, an alkynylene group has from 2 to about 6 carbon atoms. In another embodiment, an alkynylene group is branched. In another embodiment, an alkynylene group is linear.

"Aryl" means an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. Non-limiting examples of aryl groups include phenyl and naphthyl. In one embodiment, an aryl group is unsubstituted. In another embodiment, an aryl group is phenyl.

The term "cycloalkyl," as used herein, refers to a non-aromatic mono- or multicyclic ring system comprising from about 3 to about 10 ring carbon atoms. In one embodiment, a cycloalkyl contains from about 3 to about 7 ring carbon atoms. In another embodiment, a cycloalkyl contains from about 5 to about 7 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. A cycloalkyl group may also have one of its ring carbon atoms substituted as a carbonyl group to form a cycloalkanoyl group (such as cyclobutanoyl, cyclopentanoyl, cyclohexanoyl, etc. . . . ). In one embodiment, a cycloalkyl group is unsubstituted.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which has been fused to a benzene ring. Non-limiting examples of heteroaryls include pyridyl, pyrazinyl, furanyl, thienyl, pyrimidinyl, pyridonyl (including N-substituted pyridones), isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl.

The term "heterocycloalkyl," as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. A heterocycloalkyl group can be joined via a ring carbon or ring nitrogen atom. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include piperidyl, pyrrolidinyl, piperazinyl, morpholinyl, oxetanyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

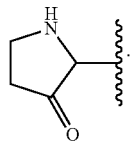

In one embodiment, a heterocycloalkyl group is unsubstituted. In another embodiment, a heterocycloalkyl group is a 5-membered heterocycloalkyl. In another embodiment, a heterocycloalkyl group is a 6-membered heterocycloalkyl.

The term "heterocycloalkenyl," as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can be optionally substituted by one or more ring system substituents, wherein "ring system substituent" is as defined below. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. An illustrative example of such a heterocycloalkenyl group is:

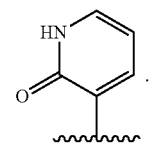

In one embodiment, a heterocycloalkenyl group is unsubstituted. In another embodiment, a heterocycloalkenyl group is a 5-membered heterocycloalkenyl. In another embodiment, a heterocycloalkenyl group is a 6-membered heterocycloalkenyl.

It should also be noted that tautomeric forms such as, for example, the moieties:

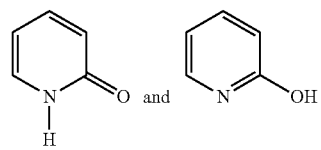

are considered equivalent in certain embodiments of this invention.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -alkylene-heteroaryl, -alkenylene-heteroaryl, -alkynylene-heteroaryl, hydroxy, hydroxyalkyl, haloalkyl, —O-alkyl, -alkylene-O-alkyl, —O-aryl, aralkoxy, acyl, aroyl, halo, nitro, cyano, carboxy, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), $Y_1Y_2N$—, $Y_1Y_2N$-alkyl-, $Y_1Y_2NC(O)$— and $Y_1Y_2NSO_2$—, wherein $Y_1$ and $Y_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH₃)₂— and the like which form moieties such as, for example:

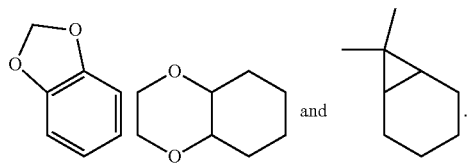

"Halo" means —Cl, —Br or —I. In one embodiment, halo refers to —Cl or —Br.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH₂F, —CHF₂, —CF₃, —CH₂Cl and —CCl₃.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH₂OH, —CH₂CH₂OH, —CH₂CH₂CH₂OH and —CH₂CH(OH)CH₃.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "purified", "in purified form" or "in isolated and purified form" for a compound refers to the physical state of the compound after being isolated from a synthetic process (e.g. from a reaction mixture), or natural source or combination thereof. Thus, the term "purified", "in purified form" or "in isolated and purified form" for a compound refers to the physical state of the compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et at, *Protective Groups in Organic Synthesis* (1991), Wiley, New York.

When any variable (e.g., aryl, heterocycle, R², etc.) occurs more than one time in any constituent or in Formula (I), its definition on each occurrence is independent of its definition at every other occurrence, unless otherwise noted.

Prodrugs and solvates of the compounds of the invention are also contemplated herein. A discussion of prodrugs is provided in T. Higuchi and V, Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a Compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol, 14 of the A.C.S. Symposium Series, and in Bioreversible Carriers in Drug Design, ed. Edward B. Roche, American Pharmaceutical Association and Pergamon Press, 1987.

For example, if a Compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$) alkyl, and the like.

Similarly, if a Compound of Formula (I) contains an alcohol functional group, a prodrug can be formed by the replacement of the hydrogen atom of the alcohol group with a group such as, for example, ($C_1$-$C_8$)alkanoyloxymethyl, $C_6$)alkanoyloxy)ethyl, 1-methyl-1-(($C_1$-$C_8$)alkanoyloxy)ethyl, ($C_1$-$C_8$)alkoxycarbonyloxymethyl, N—($C_1$-$C_6$)alkoxycarbonylaminomethyl, succinoyl, ($C_1$-$C_8$)alkanoyl, α-amino ($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, P(O)(OH)₂, —P(O)(O($C_1$-$C_8$) alkyl)₂ or glycosyl (the radical resulting from the removal of a hydroxyl group of the hemiacetal form of a carbohydrate), and the like.

If a Compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl, —C(OH)C(O)OY¹ wherein Y¹ is H, ($C_1$-$C_6$)alkyl or benzyl, —C(OY²)Y³ wherein Y² is ($C_1$-$C_4$) alkyl and Y³ is ($C_1$-$C_6$) alkyl, carboxy ($C_1$-$C_6$)alkyl, amino($C_1$-$C_4$)alkyl or mono-N— or di-N,N—($C_1$-$C_6$)alkylaminoalkyl, —C(Y⁴)Y⁵ wherein Y⁴ is H or methyl and Y⁵ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al., *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al., *AAPS PharmSciTechours.*, 5(1), article 12 (2004); and A. L. Bingham et al., *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R, spectroscopy, show the presence of the solvent (or water) in the crystals as a solvate (or hydrate).

The Compounds of Formula (I) can form salts which are also within the scope of this invention. Reference to a Compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a Compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl at al., Camille G. (eds.) *Handbook of Pharmaceutical Salts. Properties, Selection and Use*. (2002) Zurich: Wiley-VCH; S. Berge at al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, choline, t-butyl amine, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl, sec-butyl or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Masher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Compounds of Formula (I) may be atropisomers (e.g., substituted biaryls) and are considered as part of this invention. Enantiomers can also be separated by use of chiral HPLC column.

It is also possible that the Compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a Compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.)

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances.

Isotopically labelled Compounds of Formula (I) can generally be prepared using synthetic chemical procedures analogous to those disclosed herein for making the Compounds of Formula (I), by substituting an appropriate isotopically labelled starting material or reagent for a non-isotopically labelled starting material or reagent.

Polymorphic forms of the Compounds of Formula (I), and of the salts, solvates, hydrates, esters and prodrugs of the Compounds of Formula (I), are intended to be included in the present invention.

Unless otherwise stated, the following abbreviations have the stated meanings: AcOH is acetic acid, BINAP is, Boc is tert-butoxycarbonyl, CPBA is chloroperbenzoic acid, DBU is 1,8-diazabicyclo[5.4.0]undec-7-ene, DCM is dichloromethane, DIEA and DIPEA are diisopropylethylamine, DME is dimethyl ether, DMF is dimethylformamide, $Et_3N$ is triethylamine, $Et_2O$ is diethyl ether, EtOAc is ethyl acetate, EtOH is ethanol, HPLC is high performance liquid chromatography, KO$^t$Bu is potassium t-butoxide, MeI is methyl iodide, MeOH is methanol, $Mo(CO)_6$ is molybdenumhexacarbonyl, NaOAc is sodium acetate, Pd/C is palladium-on-carbon, $PdCl_2(PPh_3)_2$ is bis(triphenylphosphine)palladium (II) dichloride, Pd(dppf)$Cl_2$ is (1,1'-bis(diphenylphosphino)ferrocene)dichloropalladium(II), Pd(OAc)$_2$ is palladium(II) acetate, Pd(PPh$_3$)$_4$ is tetrakis(triphenylphosphine)palladium (0), TFA is trifluoroacetic acid, THF is tetrahydrofuran and TLC is thin layer chromatography.

The Compounds of Formula (I)

The present invention provides Compounds of Formula (I):

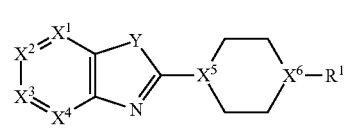

and pharmaceutically acceptable salts and solvates thereof, wherein $X^1$, $X^2$, $X^3$, $X^4$, $X^5$, $X^6$, Y and $R^1$ are defined above for the Compounds of Formula (I).

In one embodiment, $X^1$ is N.
In another embodiment, $X^1$ is —CH—.
In another embodiment, $X^1$ is —C(—W-Q)-.
In one embodiment, $X^2$ is N.
In another embodiment, $X^2$ is —CH—.
In another embodiment, $X^2$ is —C(—W-Q)-.
In one embodiment, $X^3$ is N.
In another embodiment, $X^3$ is —CH—.
In another embodiment, $X^3$ is —C(—W-Q)-.
In one embodiment, $X^4$ is N.
In another embodiment, $X^4$ is —CH—,
In another embodiment, $X^4$ is —C(—W-Q)-.
In one embodiment, one of $X^1$-$X^4$ is N.
In another embodiment, two of $X^1$-$X^4$ are —CH—, one of $X^1$-$X^4$ is —C(—W-Q)- and one of $X^1$-$X^4$ is N.
In one embodiment, $X^1$ and $X^3$ are each —CH—, $X^2$ is —C(—W-Q)- and $X^4$ is N.
In another embodiment, $X^1$ and $X^4$ are each —CH—, $X^2$ is —C(—W-Q)- and $X^3$ is N.
In another embodiment, $X^3$ and $X^4$ are each —CH—, $X^2$ is —C(—W-Q)- and $X^1$ is N.
In still another embodiment, $X^2$ and $X^4$ are each —CH—, $X^1$ is —C(—W-Q)- and $X^4$ is N.
In another embodiment, three of $X^1$-$X^4$ are —CH— and the other is N.
In one embodiment, $X^5$ is N.
In another embodiment, $X^5$ is —CH—.
In another embodiment, $X^5$ is —N-oxide-.
In one embodiment, $X^6$ is N.
In another embodiment, $X^6$ is —CH—.
In one embodiment, $X^5$ is N and $X^6$ is —CH—.
In another embodiment, $X^5$ is —CH— and $X^6$ is N.
In another embodiment, $X^5$ and $X^6$ are each —CH—,
In still another embodiment, $X^5$ and $X^6$ are each N.
In one embodiment, $X^1$ and $X^3$ are each —CH—, $X^2$ is —C(—W-Q)-, $X^4$ is N, $X^5$ is N and $X^6$ is —CH—.
In one embodiment, Y is —O—, —S— or —S(O)—.
In another embodiment, Y is —O—.
In another embodiment, Y is —S—.
In another embodiment, Y is —S(O)—.
In one embodiment W is a bond.
In another embodiment, W is —NHC(O)—.
In another embodiment, W is —NHS(O)$_2$—.
In another embodiment, W is —NH—.
In another embodiment, W is —C(O)NH—.
In another embodiment, W is —C(O)—.
In another embodiment, W is —O—.
In another embodiment, W is —CH(OH)—.
In one embodiment, Q is H.
In another embodiment, Q is halo.
In another embodiment, Q is alkyl.
In another embodiment, Q is alkenyl.

In another embodiment, Q is alkynyl.
In another embodiment, Q is aryl.
In another embodiment, Q is cycloalkyl.
In another embodiment, Q is heterocycloalkyl.
In another embodiment, Q is heterocycloalkenyl.
In another embodiment, Q is heteroaryl.
In another embodiment, Q is haloalkyl.
In another embodiment, Q is -alkylene-aryl.
In another embodiment, Q is —OH.
In another embodiment, Q is —NO$_2$.
In another embodiment, Q is —CN.

In one embodiment, W is a bond and Q is H, halo, —OH, —NO$_2$ or —CN.

In another embodiment, W is a bond and Q is haloalkyl.
In another embodiment, W is a bond and Q is alkenyl.
In another embodiment, W is a bond and Q is cycloalkyl.
In another embodiment, W is a bond and Q is heterocycloalkyl.
In another embodiment, W is a bond and Q is heterocycloalkenyl.
In another embodiment, W is a bond and Q is aryl.
In another embodiment, W is a bond and Q is phenyl.
In another embodiment, W is a bond and Q is heteroaryl.
In another embodiment, W is a bond and Q is a 5-membered heteroaryl.
In another embodiment, W is a bond and Q is a 6-membered heteroaryl.
In another embodiment, W is a bond and Q is pyridyl, pyrazolyl, pyrimidinyl, pyrazinyl, quinolinyl, isoquinolinyl, benzpyrazolyl, isothiazolyl or isoxazoyl.

In one embodiment, W is —C(O)— and Q is alkyl or heterocycloalkyl.

In another embodiment, W is —NHC(O)— and Q is alkyl, aryl or cycloalkyl.

In another embodiment, W is —C(O)NH— and Q is -alkylene-aryl.

In still another embodiment, W is —NHS(O)$_2$— and Q is alkyl.

In another embodiment, W is —NH— and Q is heteroaryl or -alkylene-aryl,

In another embodiment, W is —O— and Q is -alkylene-aryl.

In another embodiment, W is —CH(OH)— and Q is aryl.
In one embodiment, R$^1$ is heterocycloalkyl.
In another embodiment, R$^1$ is piperidinyl.
In another embodiment, R$^1$ is:

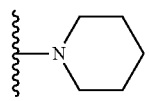

In one embodiment, the Compound of Formula (I) has the formula:

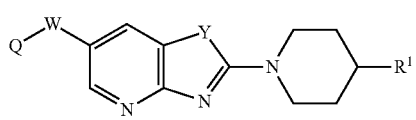

(Ia)

wherein:

Q is H, halo, alkyl, alkenyl, alkynyl, aryl, cycloalkyl, heterocycloalkyl, heterocycloalkenyl, heteroaryl, haloalkyl, -alkylene-aryl, —OH, —NO$_2$ or —CN, wherein a aryl, cycloalkyl, heterocycloalkyl, heterocycloalkenyl or heteroaryl group can be optionally substituted with R$^2$;

W is a bond, —O—, —CH(OH)—, —C(O)—, —NHC(O)—, —C(O)NH—, —NHS(O)$_2$— or —NH—;

Y is —O— or —S—;

R$^1$ is heterocycloalkyl;

each occurrence of R$^2$ represents up to 3 substituents, which can be the same or different, and are selected from halo, alkyl, —OR$^3$, —N(R$^3$)$_2$—, —CN, —NO$_2$, —NHC(O)-alkyl, —C(O)N(R$^3$)$_2$, heteroaryl, haloalkyl, alkenyl, —C(O)—R$^3$ or hydroxyalkyl; and each occurrence of R$^3$ is independently H or alkyl.

In one embodiment, for the compounds of formula (Ia), R$^1$ is piperidinyl.

In another embodiment, for the compounds of formula (Ia), Y is —O— or —S—.

In another embodiment, for the compounds of formula (Ia), Y is —O—.

In another embodiment, for the compounds of formula (Ia), Y is —S—.

In one embodiment, for the compounds of formula (Ia), R$^1$ is piperidinyl and Y is —S—.

In another embodiment, for the compounds of formula (Ia), R$^1$ is piperidinyl and Y is —O—.

In one embodiment, for the compounds of formula (Ia), W is a bond and Q is aryl or heteroaryl.

In another embodiment, for the compounds of formula (Ia), R$^1$ is piperidinyl, W is a bond and Q is aryl or heteroaryl.

In another embodiment, for the compounds of formula (Ia), R$^1$ is piperidinyl, Y is —O—, W is a bond and Q is aryl or heteroaryl.

In still another embodiment, for the compounds of formula (Ia), R$^1$ is piperidinyl, Y is —S—, W is a bond and Q is aryl or heteroaryl.

In one embodiment, the Compound of Formula (I) has the formula:

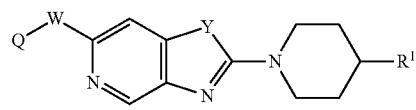

(Ib)

wherein:

Q is H, halo, alkyl, alkenyl, alkynyl, aryl, cycloalkyl, heterocycloalkyl, heterocycloalkenyl, heteroaryl, haloalkyl, -alkylene-aryl, —OH, —NO$_2$ or —CN, wherein a aryl, cycloalkyl, heterocycloalkyl, heterocycloalkenyl or heteroaryl group can be optionally substituted with R$^2$;

W is a bond, —O—, —CH(OH)—, —C(O)—, —NHC(O)—, —C(O)NH—, —NHS(O)$_2$— or —NH—;

Y is —O— or —S—;

R$^1$ is heterocycloalkyl;

each occurrence of R$^2$ represents up to 3 substituents, which can be the same or different, and are selected from halo, alkyl, —OR$^3$, —N(R$^3$)$_2$—, —CN, —NO$_2$, —NHC(O)-alkyl, —C(O)N(R$^3$)$_2$, heteroaryl, haloalkyl, alkenyl, —C(O)—R$^3$ or hydroxyalkyl; and each occurrence of R$^3$ is independently H or alkyl.

In one embodiment, for the compounds of formula (Ib), R$^1$ is piperidinyl.

In another embodiment, for the compounds of formula (Ib), Y is —O— or —S—.

In another embodiment, for the compounds of formula (Ib), Y is —O—.

In another embodiment, for the compounds of formula (Ib), Y is —S—.

In one embodiment, for the compounds of formula (Ib), $R^1$ is piperidinyl and Y is —S—.

In another embodiment, for the compounds of formula (Ib), is piperidinyl and Y is —O—.

In one embodiment, for the compounds of formula (Ib), W is a bond and Q is aryl or heteroaryl.

In another embodiment, for the compounds of formula (Ib), $R^1$ is piperidinyl, W is a bond and Q is aryl or heteroaryl.

In another embodiment, for the compounds of formula (Ib), $R^1$ is piperidinyl, Y is —O—, W is a bond and Q is aryl or heteroaryl.

In still another embodiment, for the compounds of formula (Ib), $R^1$ is piperidinyl, Y is —S—, W is a bond and Q is aryl or heteroaryl.

In one embodiment, the Compound of Formula (I) has the formula:

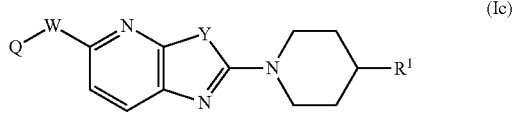

wherein:

Q is H, halo, alkyl, alkenyl, alkynyl, aryl, cycloalkyl, heterocycloalkyl, heterocycloalkenyl, heteroaryl, haloalkyl, -alkylene-aryl, —OH, —$NO_2$ or —CN, wherein a aryl, cycloalkyl, heterocycloalkyl, heterocycloalkenyl or heteroaryl group can be optionally substituted with $R^2$;

W is a bond, —O—, —CH(OH)—, —C(O)—, —NHC(O)—, —C(O)NH—, —NHS(O)$_2$— or —NH—;

Y is —O— or —S—;

$R^1$ is heterocycloalkyl;

each occurrence of $R^2$ represents up to 3 substituents, which can be the same or different, and are selected from halo, alkyl, —$OR^3$, —$N(R^3)_2$—, —CN, —$NO_2$, —NHC(O)-alkyl, —C(O)N($R^3)_2$, heteroaryl, haloalkyl, alkenyl, —C(O)—$R^3$ or hydroxyalkyl; and each occurrence of $R^3$ is independently H or alkyl.

In one embodiment, for the compounds of formula (Ic), $R^1$ is piperidinyl.

In another embodiment, for the compounds of formula (Ic), Y is —O— or —S—.

In another embodiment, for the compounds of formula (Ic), Y is —O—.

In another embodiment, for the compounds of formula (Ic), Y is —S—.

In one embodiment, for the compounds of formula (Ic), $R^1$ is piperidinyl and Y is —S—.

In another embodiment, for the compounds of formula (Ic), $R^1$ is piperidinyl and Y is —O—.

In one embodiment, for the compounds of formula (Ic), W is a bond and Q is aryl or heteroaryl.

In another embodiment, for the compounds of formula (Ic), $R^1$ is piperidinyl, W is a bond and Q is aryl or heteroaryl.

In another embodiment, for the compounds of formula (Ic), $R^1$ is piperidinyl, Y is —O—, W is a bond and Q is aryl or heteroaryl.

In still another embodiment, for the compounds of formula (Ic), $R^1$ is piperidinyl, Y is —S—, W is a bond and Q is aryl or heteroaryl.

In one embodiment, the Compound of Formula (I) has the formula:

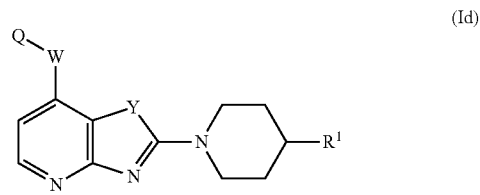

wherein:

Q is H, halo, alkyl, alkenyl, alkynyl, aryl, cycloalkyl, heterocycloalkyl, heterocycloalkenyl, heteroaryl, haloalkyl, -alkylene-aryl, —OH, —$NO_2$ or —CN, wherein a aryl, cycloalkyl, heterocycloalkyl, heterocycloalkenyl or heteroaryl group can be optionally substituted with $R^2$;

W is a bond, —O—, —CH(OH)—, —C(O)—, —NHC(O)—, —C(O)NH—, —NHS(O)$_2$— or —NH—;

Y is —O— or —S—;

$R^1$ is heterocycloalkyl;

each occurrence of $R^2$ represents up to 3 substituents, which can be the same or different, and are selected from halo, alkyl, —$OR^3$, —$N(R^3)_2$—, —CN, —$NO_2$, —NHC(O)-alkyl, —C(O)N($R^3)_2$, heteroaryl, haloalkyl, alkenyl, —C(O)—$R^3$ or hydroxyalkyl; and each occurrence of $R^3$ is independently H or alkyl.

In one embodiment, for the compounds of formula (Id), $R^1$ is piperidinyl.

In another embodiment, for the compounds of formula (Id), Y is —O— or —S—.

In another embodiment, for the compounds of formula (Ic), Y is —O—.

In another embodiment, for the compounds of formula (Id), Y is —S—.

In one embodiment, for the compounds of formula (Id), $R^1$ is piperidinyl and Y is —S—.

In another embodiment, for the compounds of formula (Id), $R^1$ is piperidinyl and Y is —O—.

In one embodiment, for the compounds of formula (Id), W is a bond and Q is aryl or heteroaryl.

In another embodiment, for the compounds of formula (Id), $R^1$ is piperidinyl, W is a bond and Q is aryl or heteroaryl.

In another embodiment, for the compounds of formula (Id), $R^1$ is piperidinyl, is —O—, W is a bond and Q is aryl or heteroaryl.

In still another embodiment, for the compounds of formula (Id), $R^1$ is piperidinyl, Y is —S—, W is a bond and Q is aryl or heteroaryl.

In one embodiment, for the Compounds of Formulas (Ia)-(Id), variables Q, W, Y and $R^1$ are selected independently from each other.

In another embodiment, the Compounds of Formulas (Ia)-(Id) are in purified form.

Non-limiting Illustrative examples of the Compounds of Formula (I) include the following compounds:

| Compound No. | Structure |
|---|---|
| 1 | 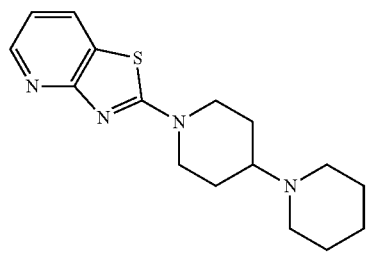 |
| 2 | 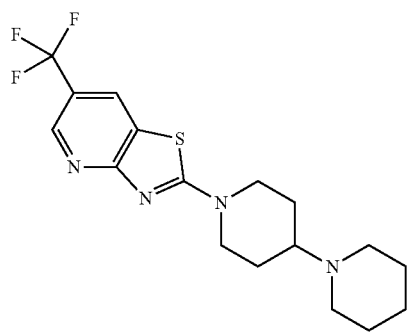 |
| 3 | 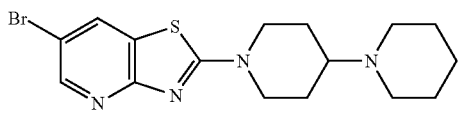 |
| 4 | 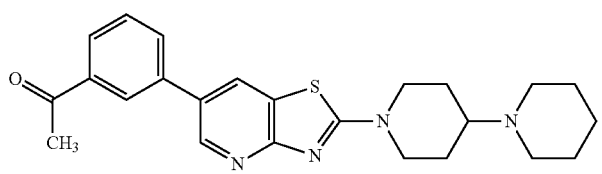 |
| 5 | 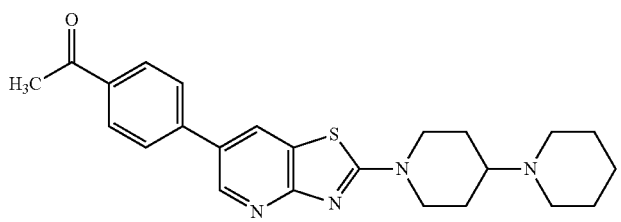 |
| 6 | 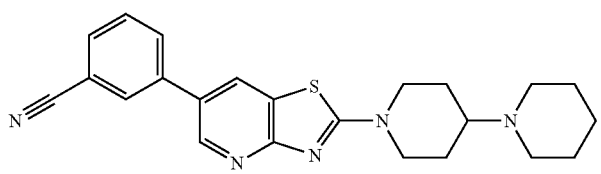 |
| 7 | 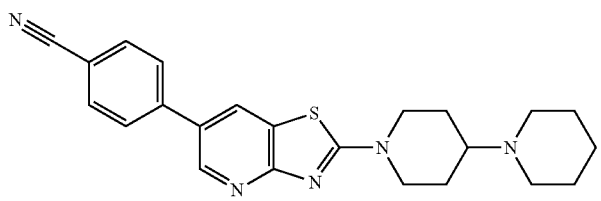 |

-continued

| Compound No. | Structure |
|---|---|
| 8 | [Structure: N-(4-(2-([1,4'-bipiperidin]-1'-yl)thiazolo[4,5-b]pyridin-6-yl)phenyl)acetamide] |
| 9 | [Structure: 2-([1,4'-bipiperidin]-1'-yl)-6-(4-methoxyphenyl)thiazolo[4,5-b]pyridine] |
| 10 | [Structure: 5-(2-([1,4'-bipiperidin]-1'-yl)thiazolo[4,5-b]pyridin-6-yl)-2-fluorobenzonitrile] |
| 11 | [Structure: 2-([1,4'-bipiperidin]-1'-yl)-6-(2-fluoropyridin-4-yl)thiazolo[4,5-b]pyridine] |
| 12 | [Structure: 2-([1,4'-bipiperidin]-1'-yl)-6-(6-fluoropyridin-3-yl)thiazolo[4,5-b]pyridine] |

-continued

| Compound No. | Structure |
|---|---|
| 13 | 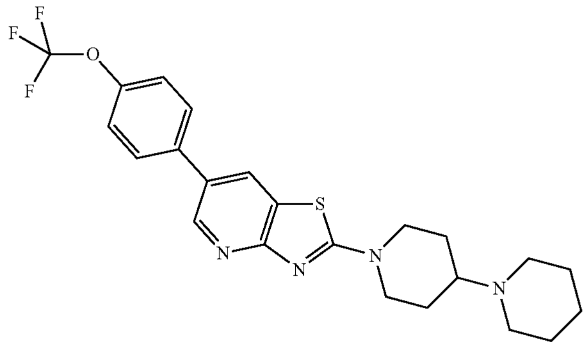 |
| 14 | 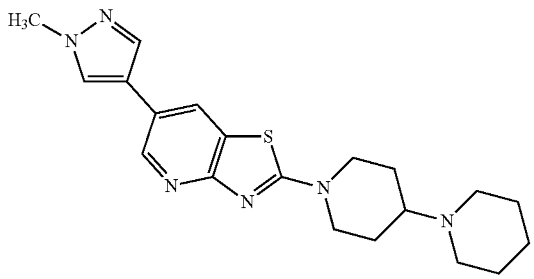 |
| 15 | 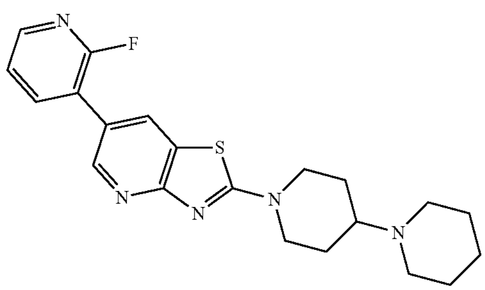 |
| 16 | 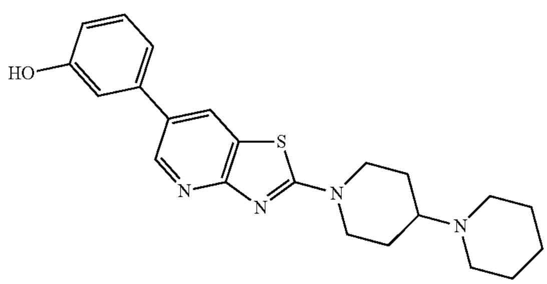 |
| 17 | 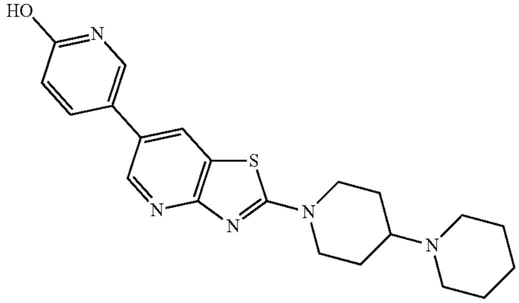 |

-continued
| Compound No. | Structure |
|---|---|
| 18 | 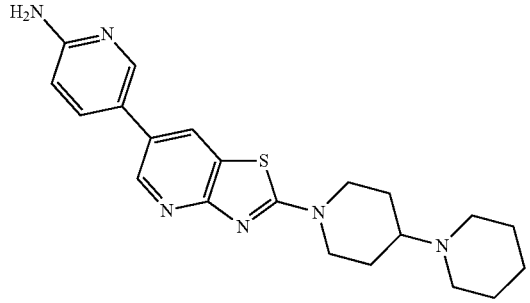 |
| 19 | 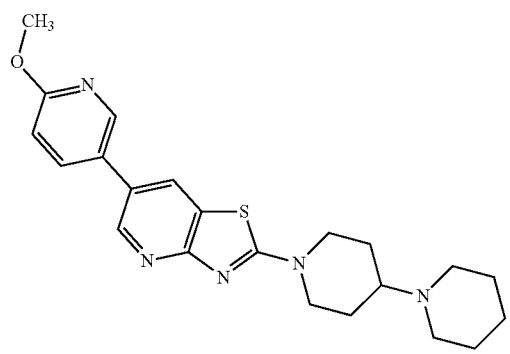 |
| 20 | 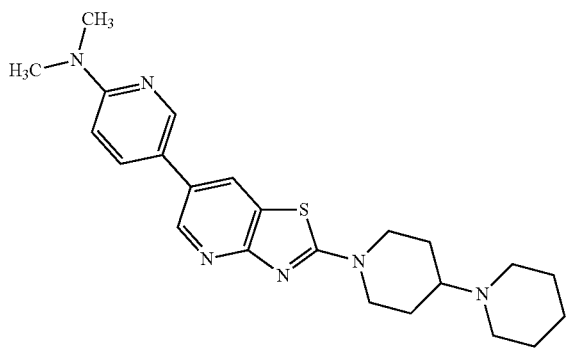 |
| 21 | 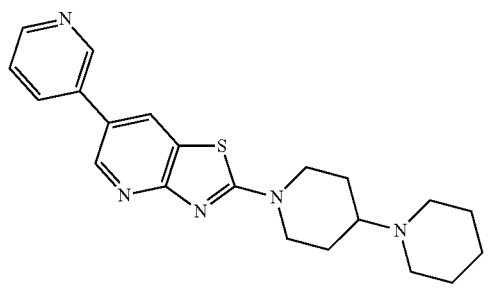 |
| 22 | 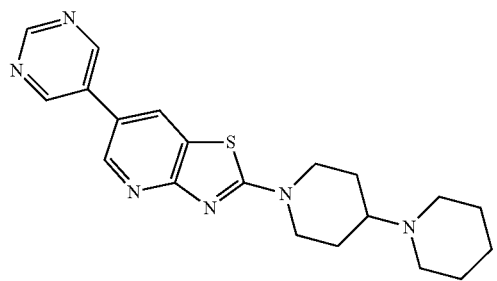 |

-continued
| Compound No. | Structure |
|---|---|
| 23 | 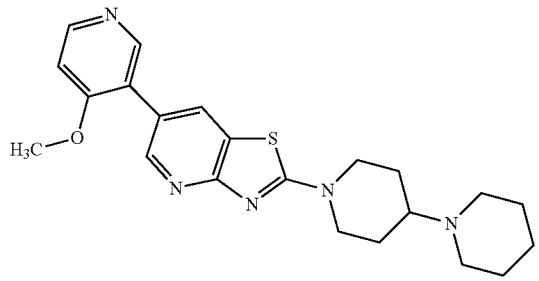 |
| 24 | 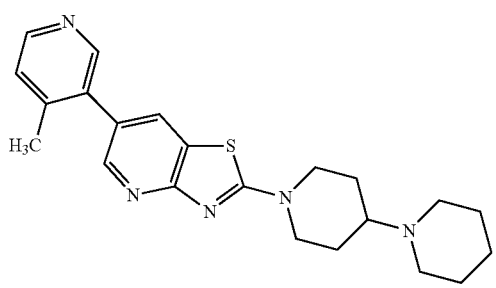 |
| 25 | 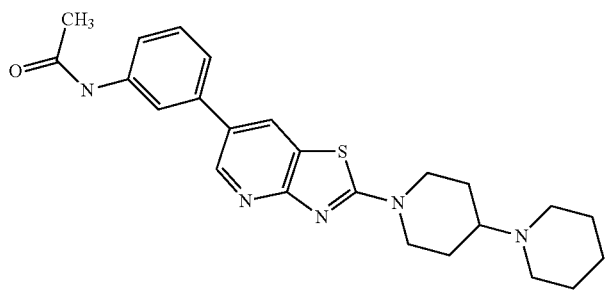 |
| 26 | 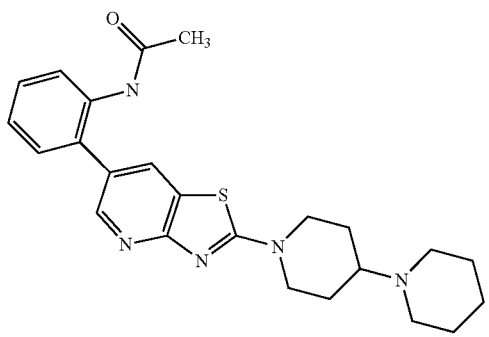 |
| 27 | 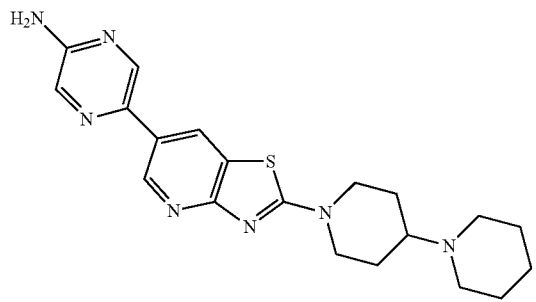 |

-continued
| Compound No. | Structure |
|---|---|
| 28 | 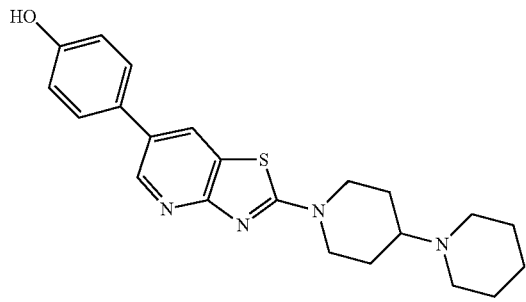 |
| 29 | 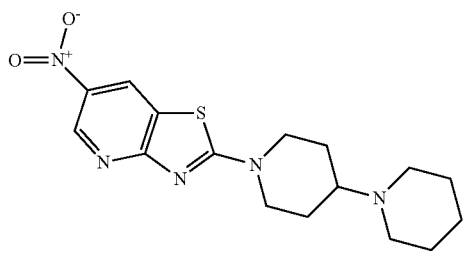 |
| 30 | 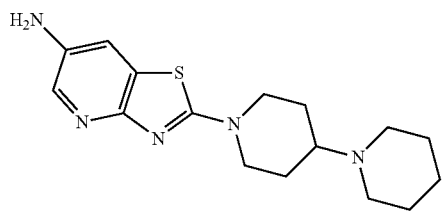 |
| 31 | 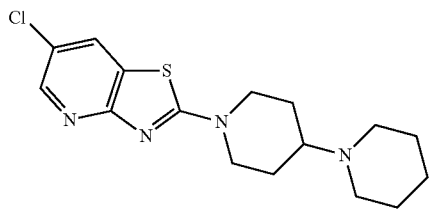 |
| 32 | 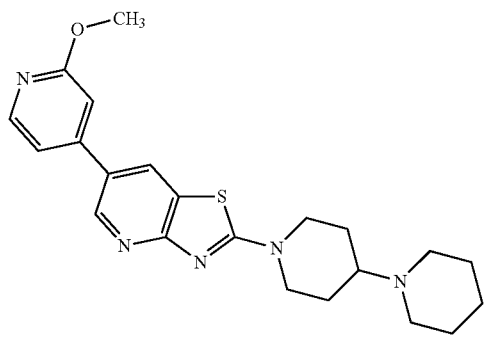 |

-continued
| Compound No. | Structure |
|---|---|
| 33 | 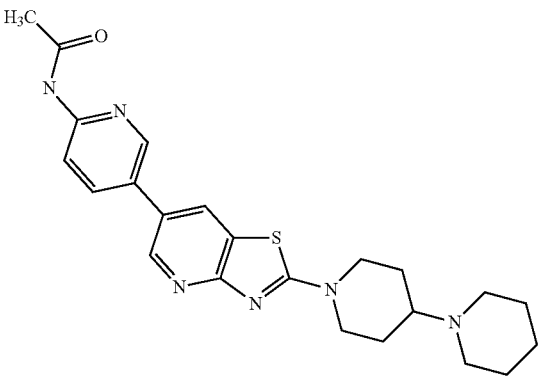 |
| 34 | 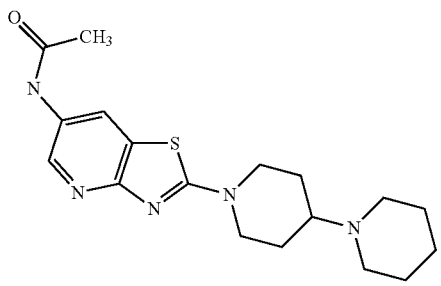 |
| 35 | 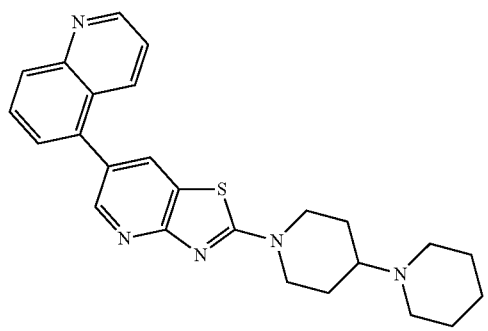 |
| 36 | 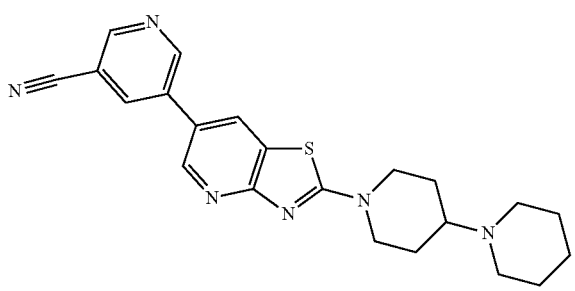 |
| 37 | 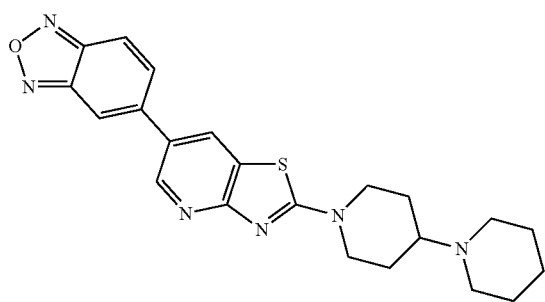 |

| Compound No. | Structure |
|---|---|
| 38 | 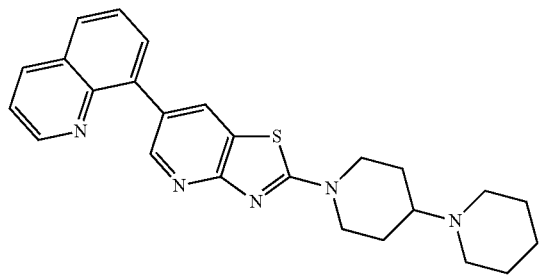 |
| 39 | 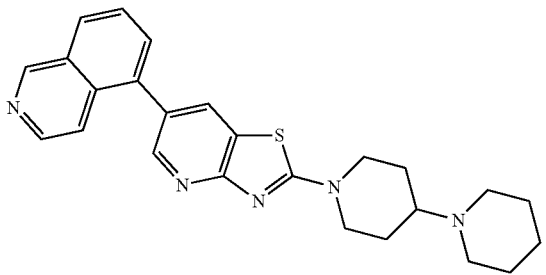 |
| 40 | 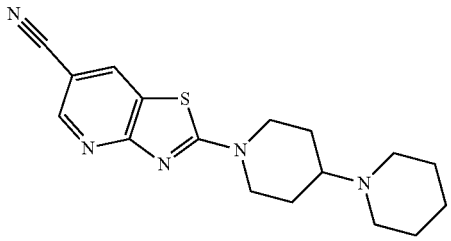 |
| 41 | 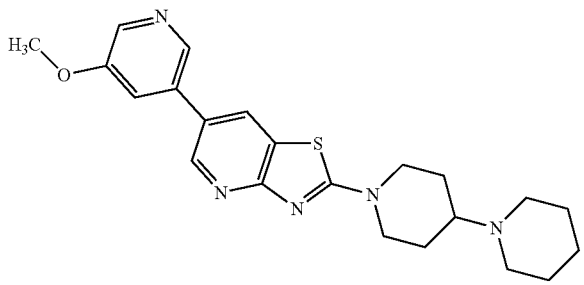 |
| 42 | 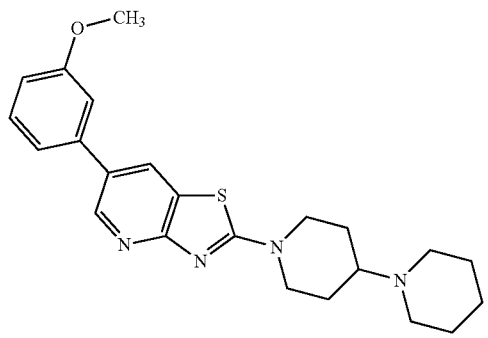 |

-continued
| Compound No. | Structure |
|---|---|
| 43 | 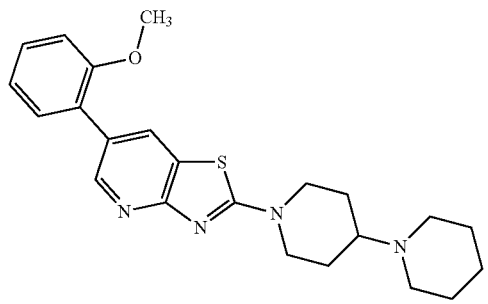 |
| 44 | 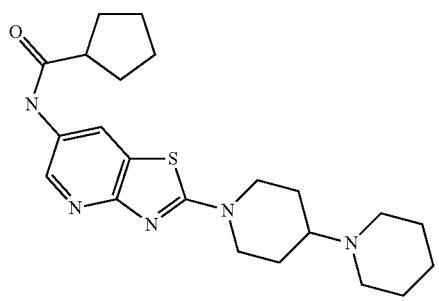 |
| 45 | 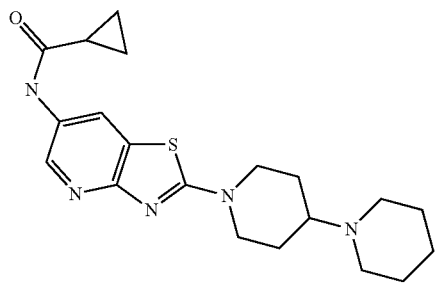 |
| 46 | 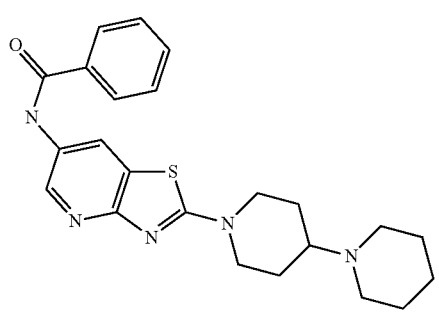 |
| 47 | 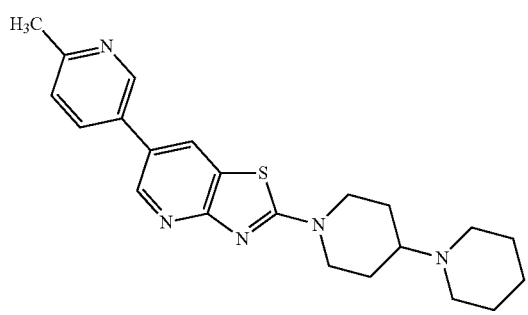 |

| Compound No. | Structure |
|---|---|
| 48 | 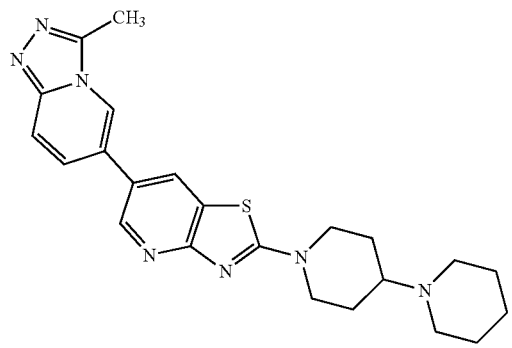 |
| 49 | 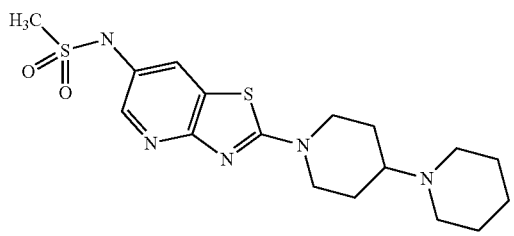 |
| 50 | 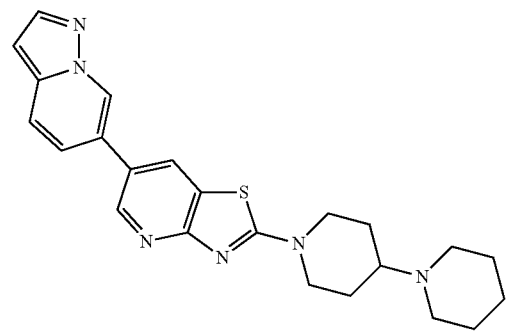 |
| 51 | 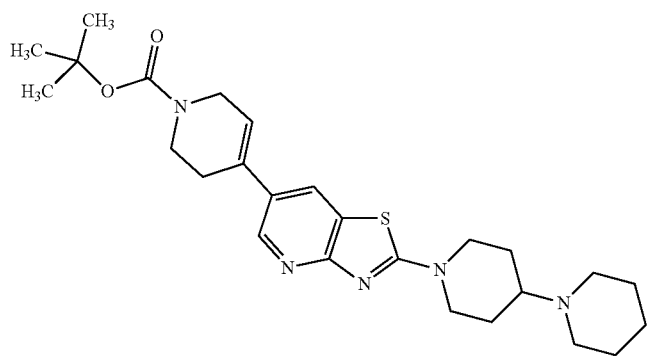 |
| 52 | 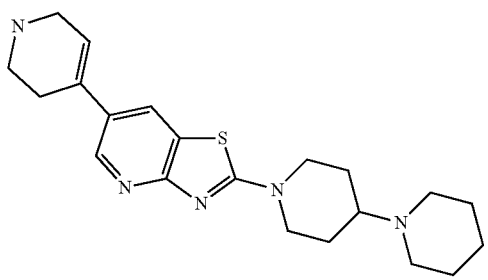 |

-continued
| Compound No. | Structure |
|---|---|
| 53 | 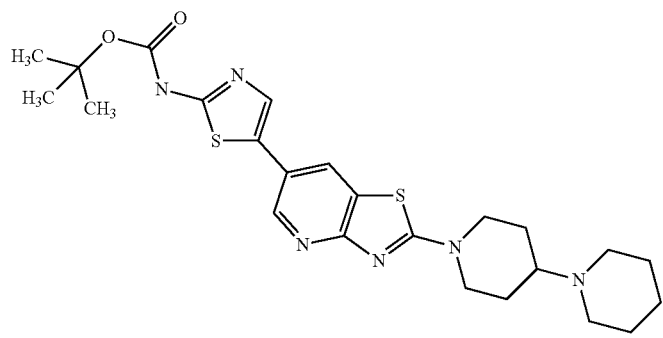 |
| 54 | 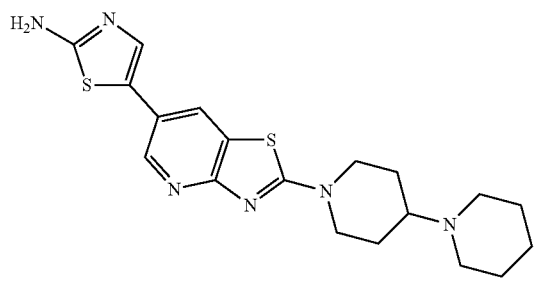 |
| 55 | 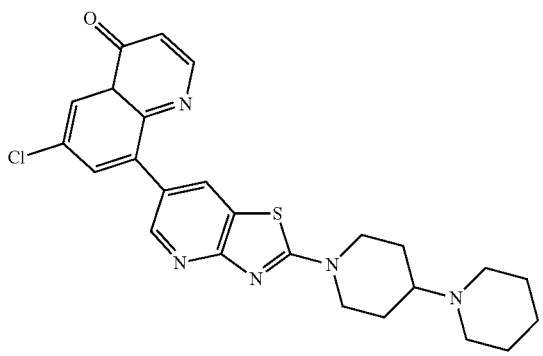 |
| 56 | 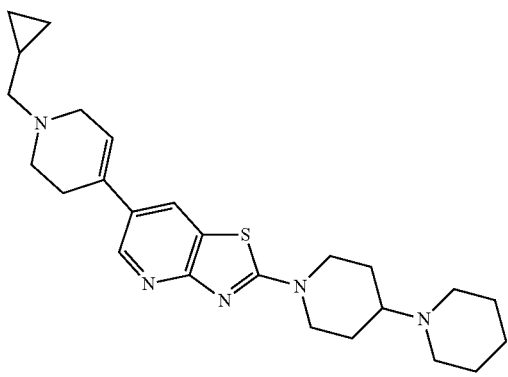 |
| 57 | 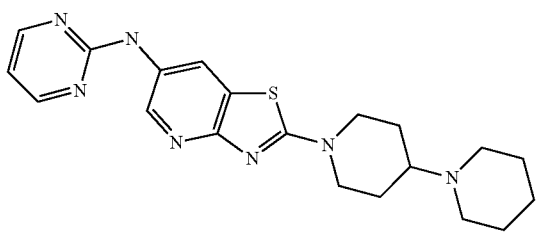 |

-continued

| Compound No. | Structure |
|---|---|
| 58 | 6-chloro-thiazolo[pyridine]-2-yl linked to 4-(piperidin-1-yl)piperidine |
| 59 | 3-acetylphenyl substituted thiazolopyridine linked to 4-(piperidin-1-yl)piperidine |
| 60 | 4-cyanophenyl substituted thiazolopyridine linked to 4-(piperidin-1-yl)piperidine |
| 61 | 6-fluoropyridin-3-yl substituted thiazolopyridine linked to 4-(piperidin-1-yl)piperidine |
| 62 | 6-aminopyridin-3-yl substituted thiazolopyridine linked to 4-(piperidin-1-yl)piperidine |
| 63 | 3,5-dimethylisoxazol-4-yl substituted thiazolopyridine linked to 4-(piperidin-1-yl)piperidine |
| 64 | 4-fluoro-3-cyanophenyl substituted thiazolopyridine linked to 4-(piperidin-1-yl)piperidine |
| 65 | 2-fluoropyridin-4-yl substituted thiazolopyridine linked to 4-(piperidin-1-yl)piperidine |

| Compound No. | Structure |
|---|---|
| 66 | 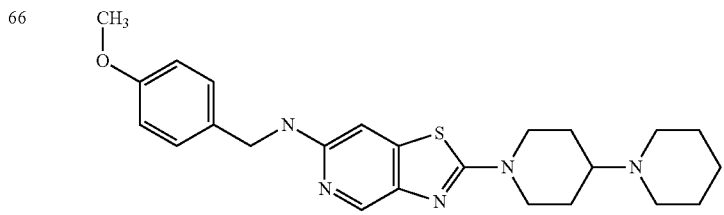 |
| 67 | 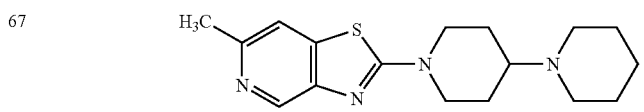 |
| 68 | 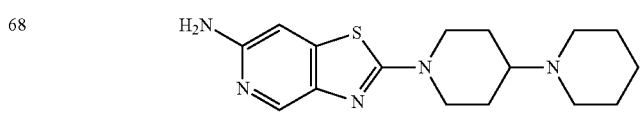 |
| 69 | 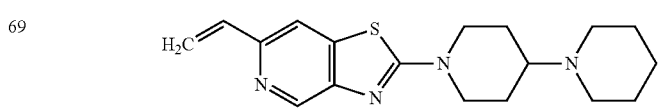 |
| 70 | 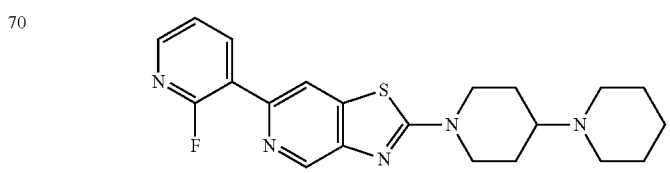 |
| 71 | 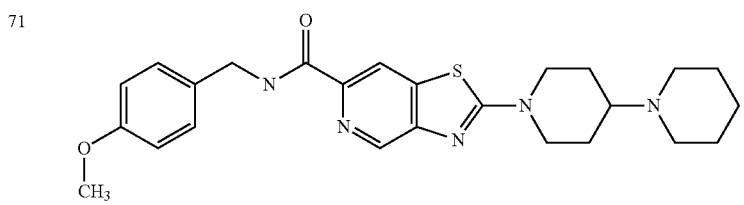 |
| 72 | 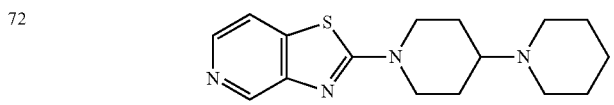 |
| 73 | 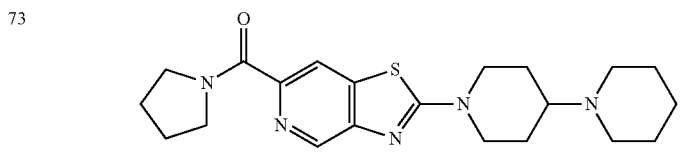 |
| 74 | 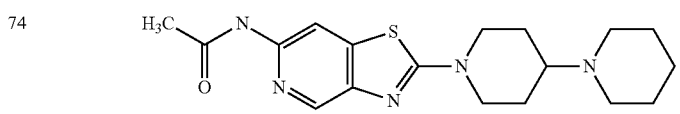 |
| 75 | 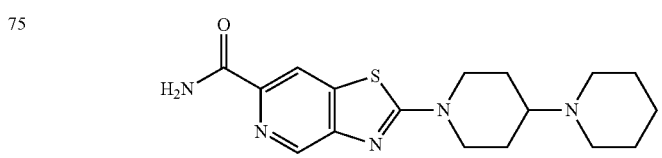 |

-continued
| Compound No. | Structure |
|---|---|
| 76 | 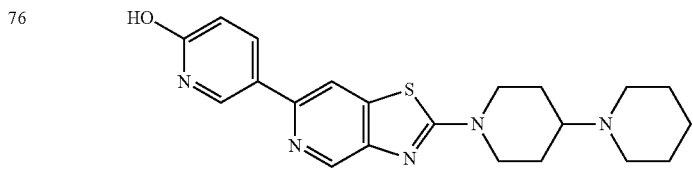 |
| 77 | 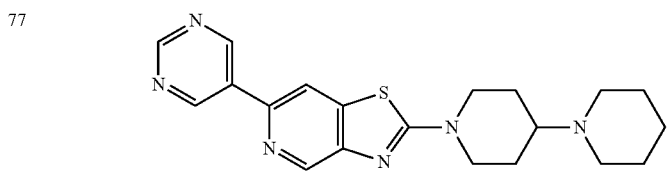 |
| 78 | 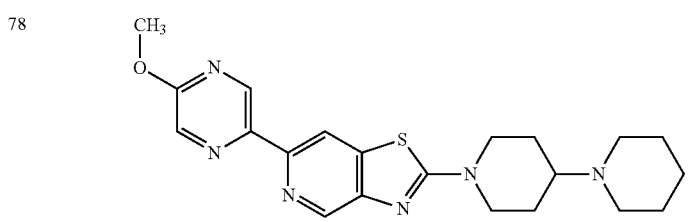 |
| 79 | 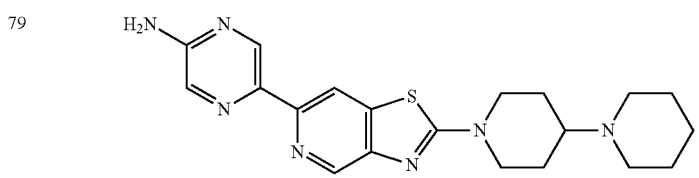 |
| 80 | 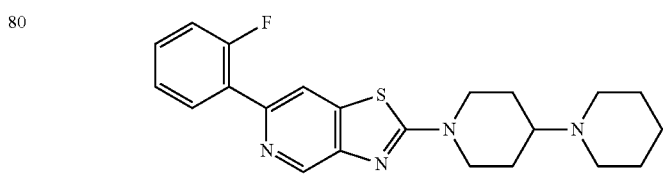 |
| 81 | 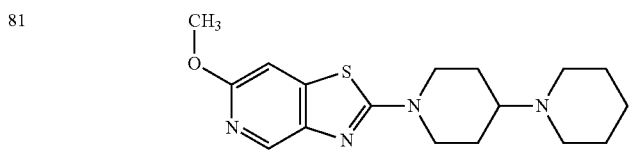 |
| 82 | 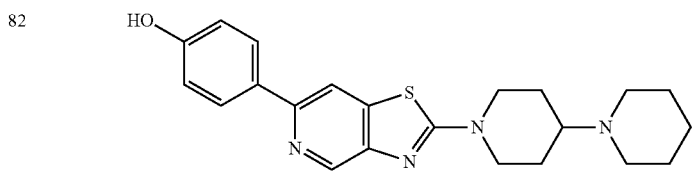 |
| 83 | 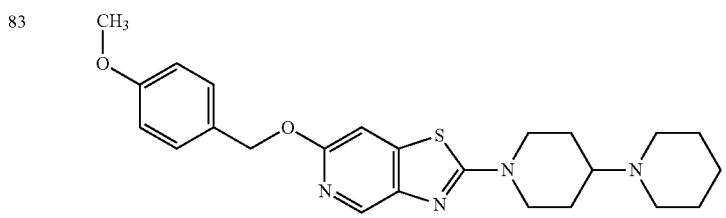 |

-continued
| Compound No. | Structure |
|---|---|
| 84 | 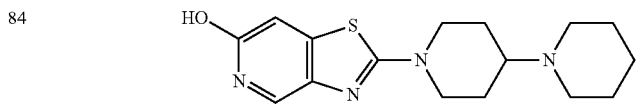 |
| 85 | 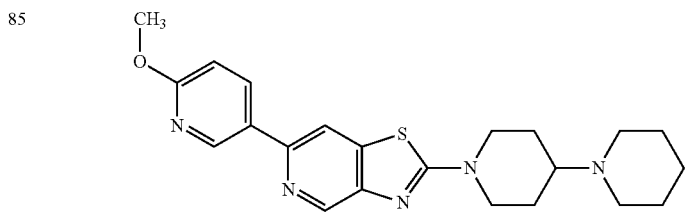 |
| 86 | 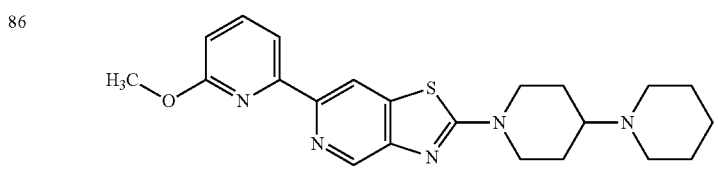 |
| 87 | 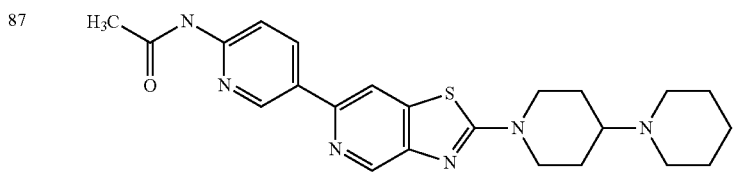 |
| 88 | 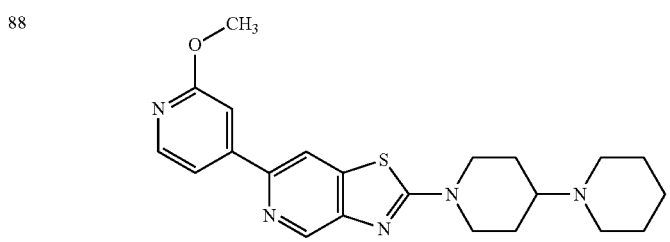 |
| 89 | 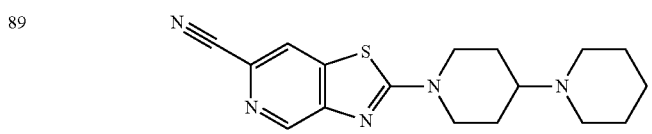 |
| 90 | 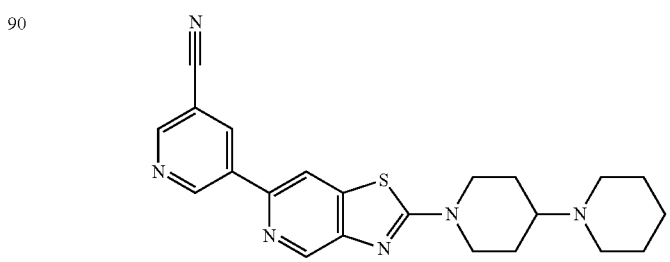 |
| 91 | 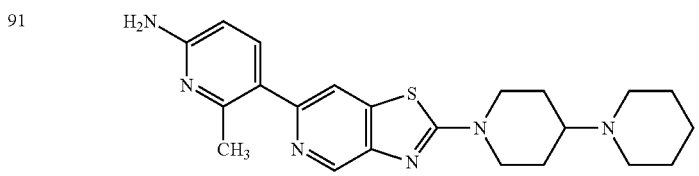 |

-continued

| Compound No. | Structure |
|---|---|
| 92 | (structure) |
| 93 | (structure) |
| 94 | (structure) |
| 95 | (structure) |
| 96 | (structure) |
| 97 | (structure) |
| 98 | (structure) |
| 99 | (structure) |

| Compound No. | Structure |
|---|---|
| 100 | 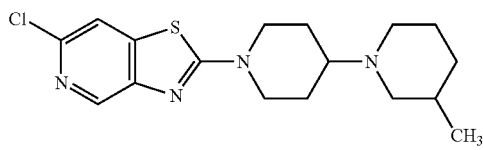 |
| 101 | 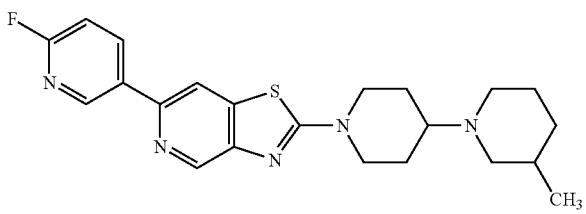 |
| 102 | 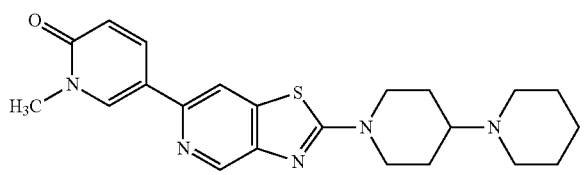 |
| 103 | 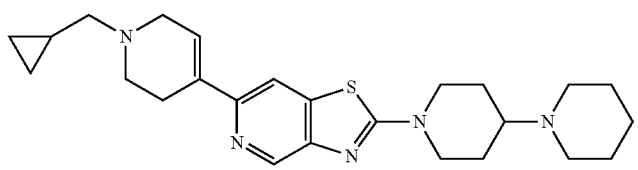 |
| 104 | 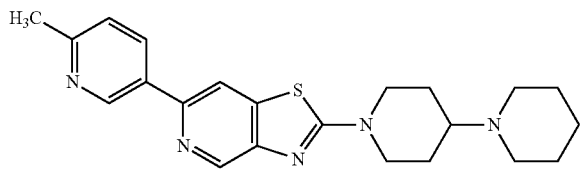 |
| 105 | 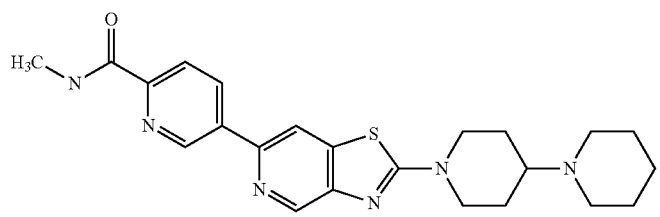 |
| 106 | 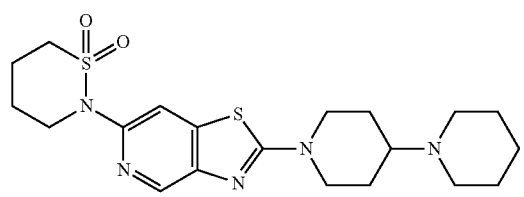 |
| 107 | 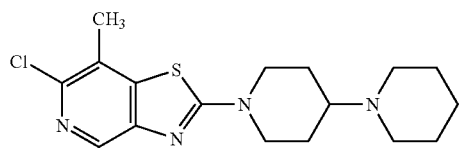 |

-continued

| Compound No. | Structure |
|---|---|
| 108 | 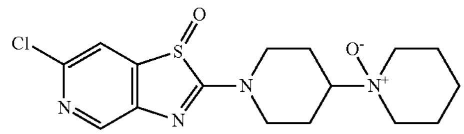 |
| 109 | 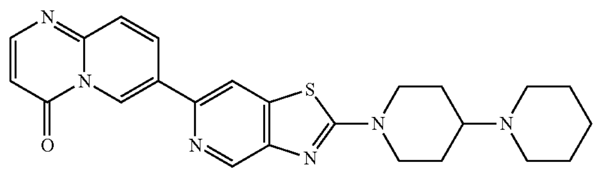 |
| 110 | 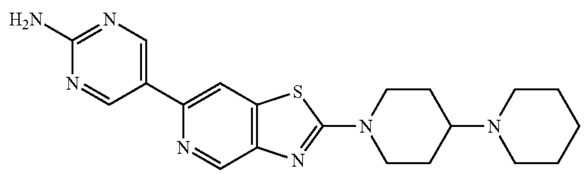 |
| 111 | 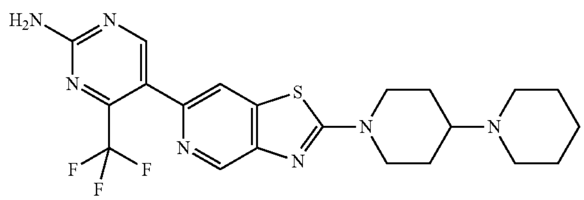 |
| 112 | 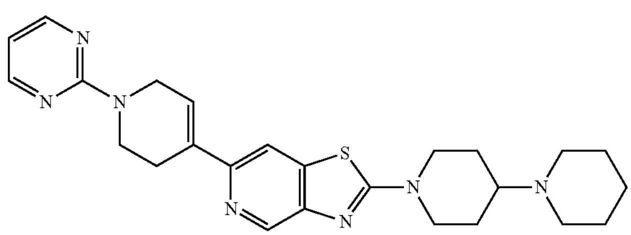 |
| 113 | 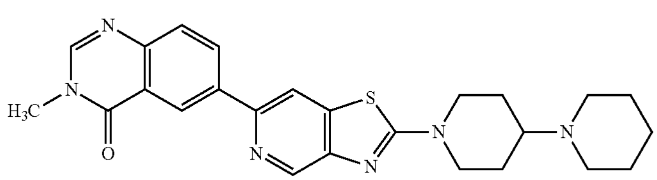 |
| 114 | 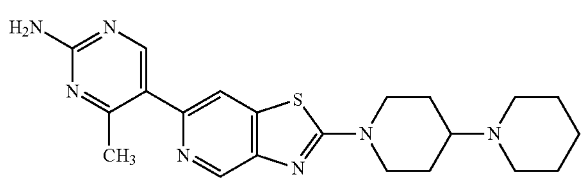 |
| 115 | 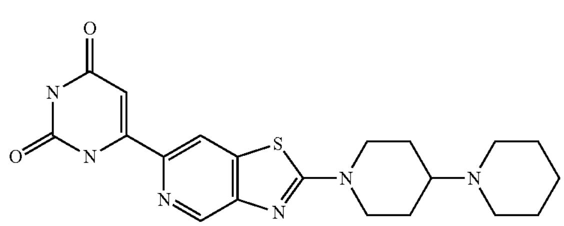 |

-continued
| Compound No. | Structure |
|---|---|
| 116 | 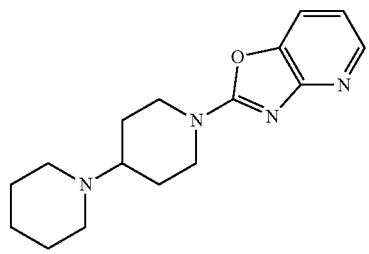 |
| 117 | 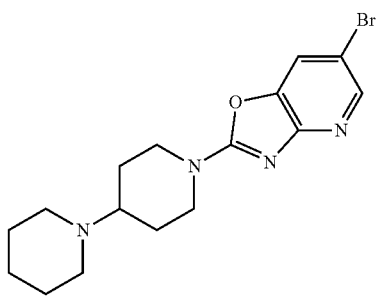 |
| 118 | 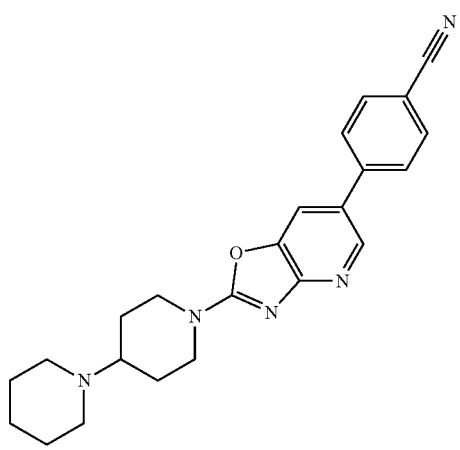 |
| 119 | 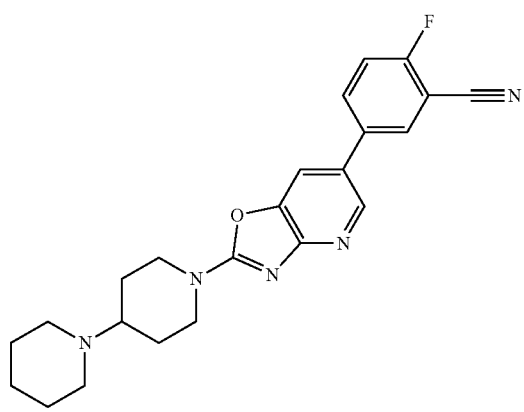 |

-continued
| Compound No. | Structure |
|---|---|
| 120 | 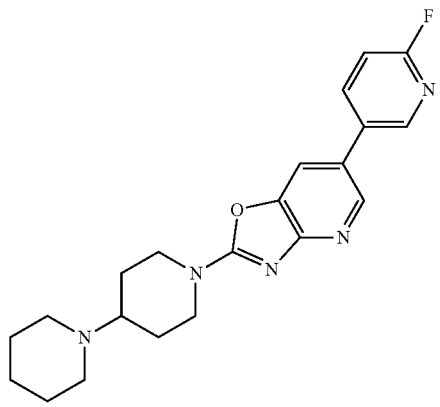 |
| 121 | 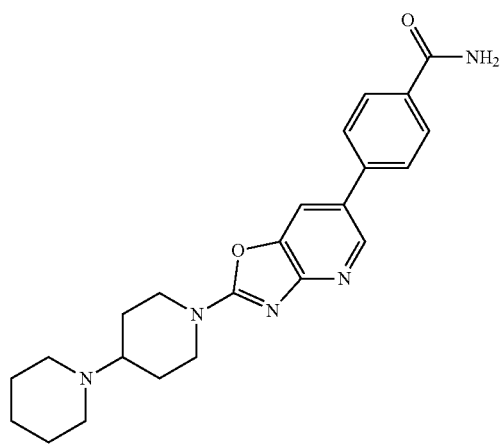 |
| 122 | 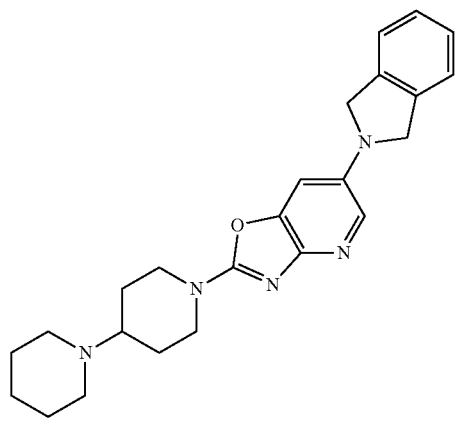 |

| Compound No. | Structure |
|---|---|
| 123 | 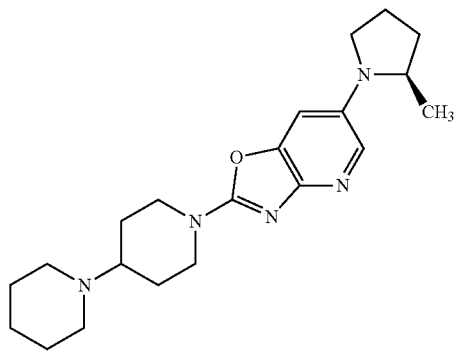 |
| 124 | 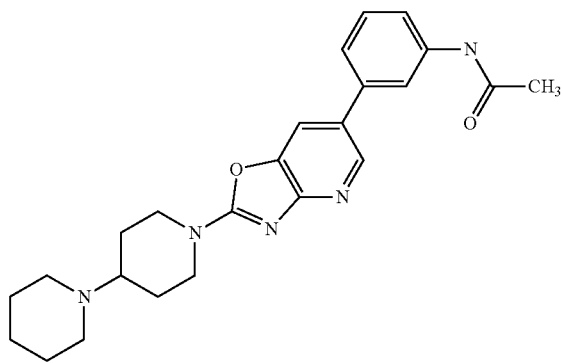 |
| 125 | 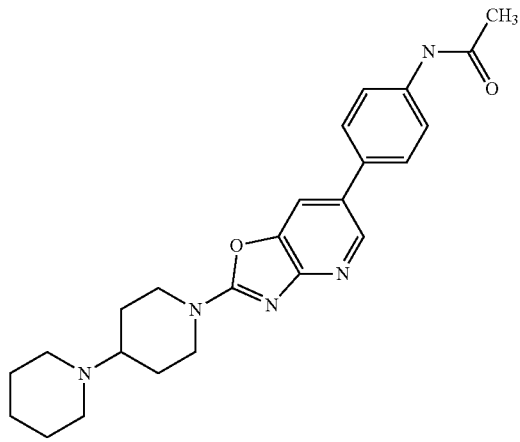 |
| 126 | 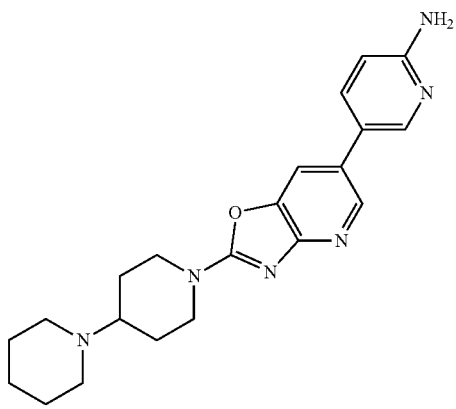 |

-continued
| Compound No. | Structure |
|---|---|
| 127 | 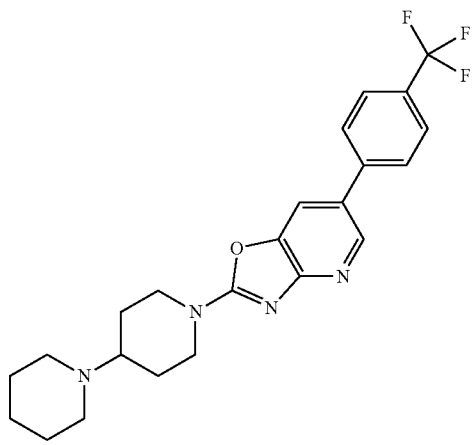 |
| 128 | 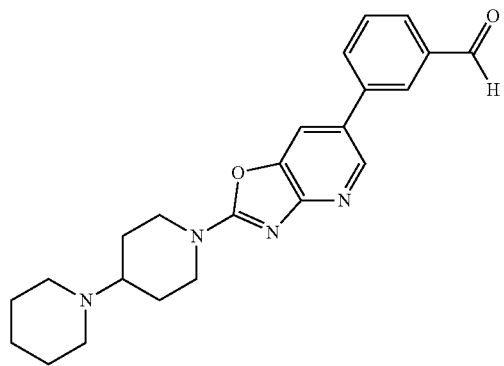 |
| 129 | 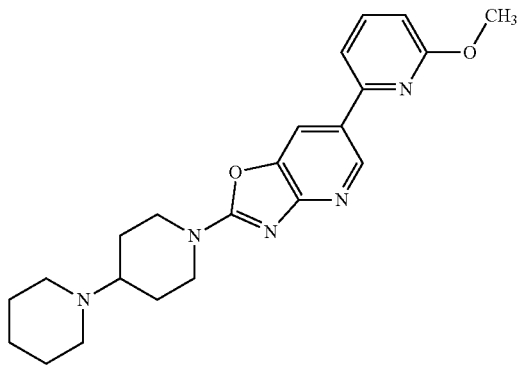 |
| 130 | 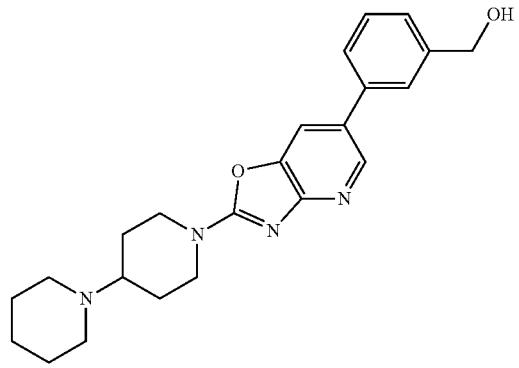 |

-continued
| Compound No. | Structure |
|---|---|
| 131 | 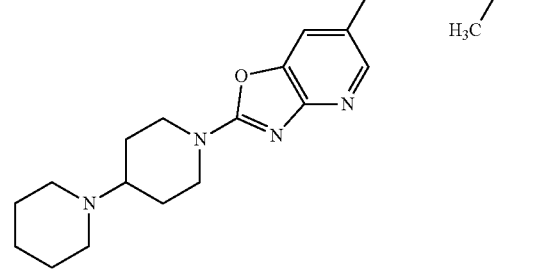 |
| 132 | 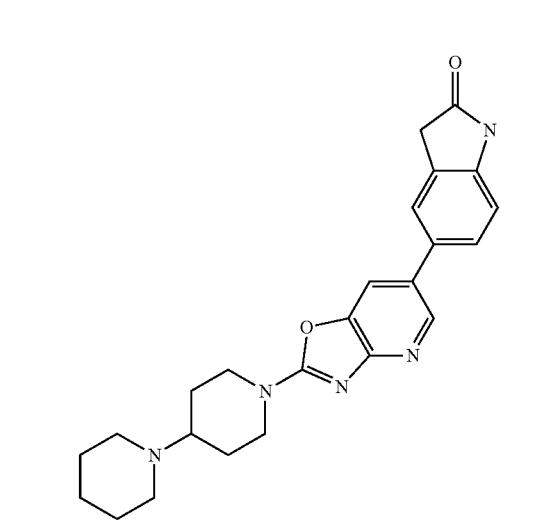 |
| 133 | 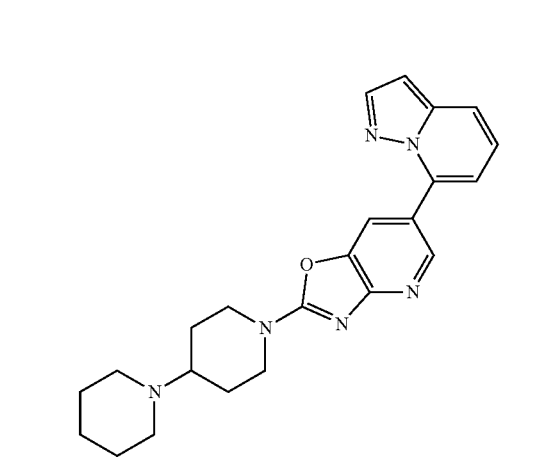 |

| Compound No. | Structure |
|---|---|
| 134 | 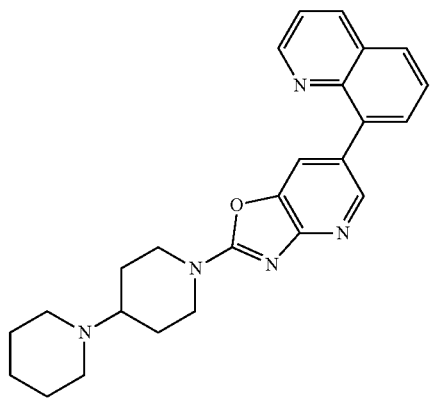 |
| 135 | 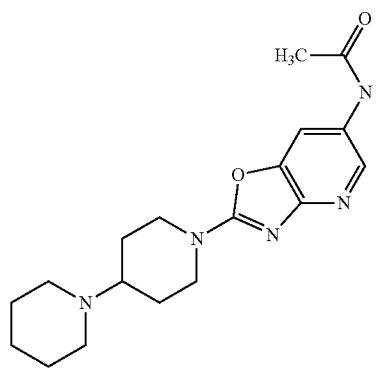 |
| 136 | 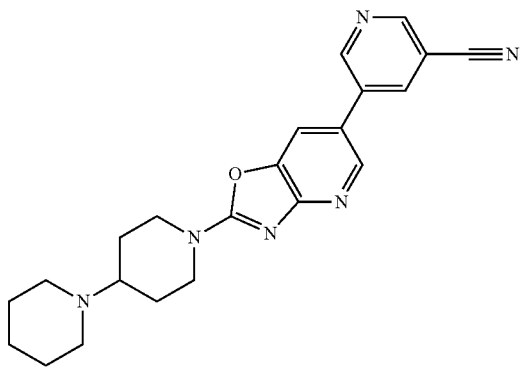 |
| 137 | 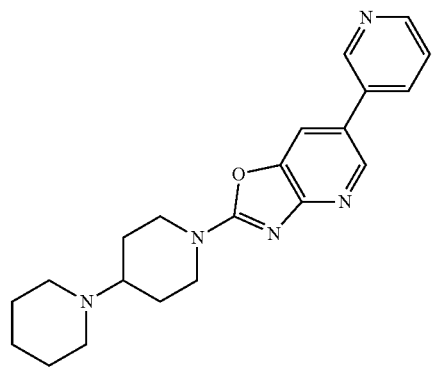 |

-continued
| Compound No. | Structure |
|---|---|
| 138 | 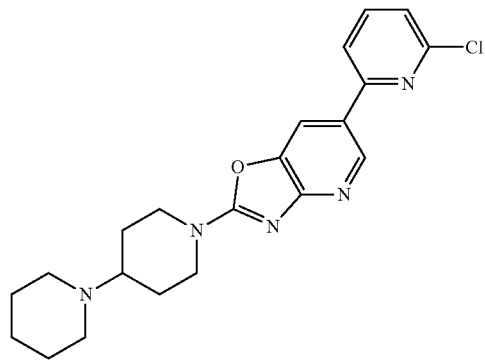 |
| 139 | 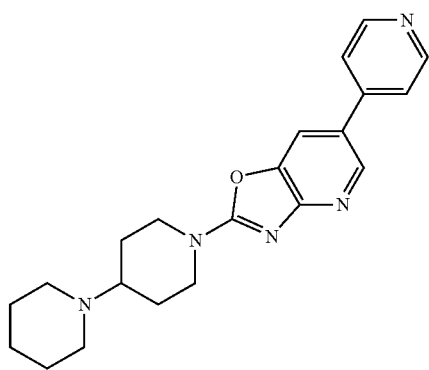 |
| 140 | 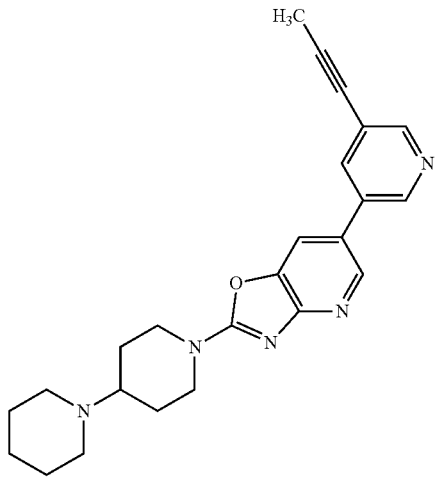 |

| Compound No. | Structure |
|---|---|
| 141 | 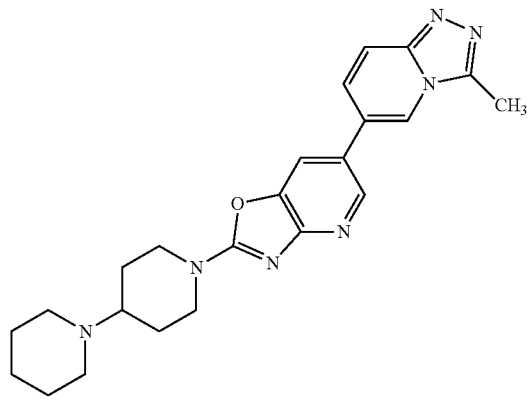 |
| 142 | 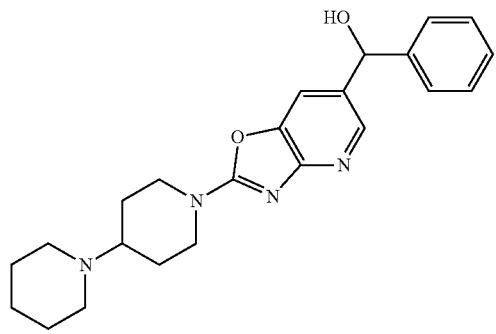 |
| 143 | 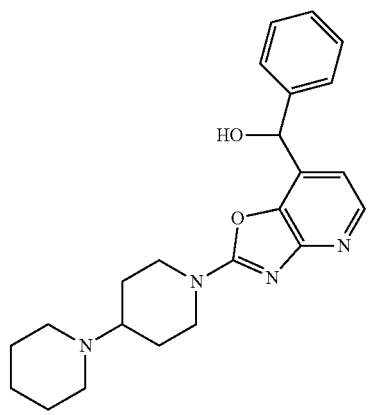 |
| 144 | 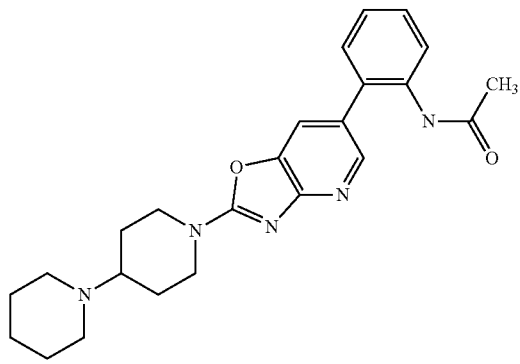 |

| Compound No. | Structure |
|---|---|
| 145 | 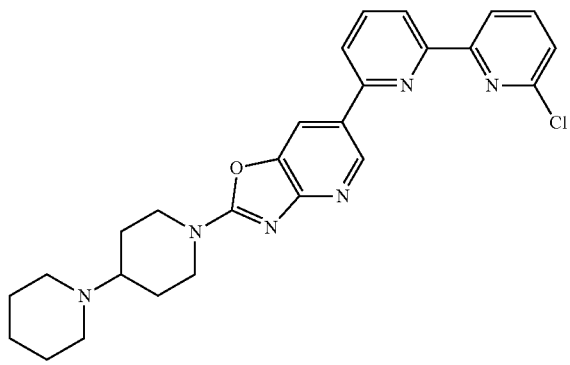 |
| 146 | 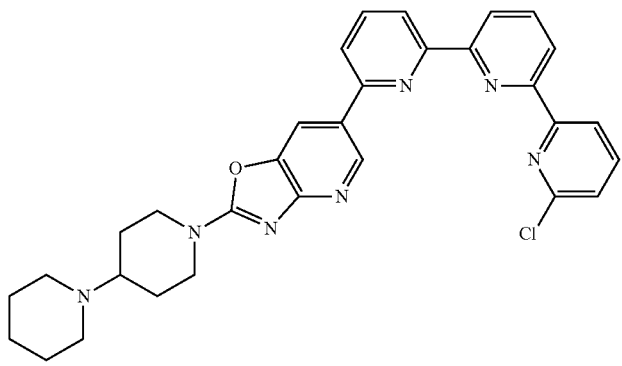 |
| 147 | 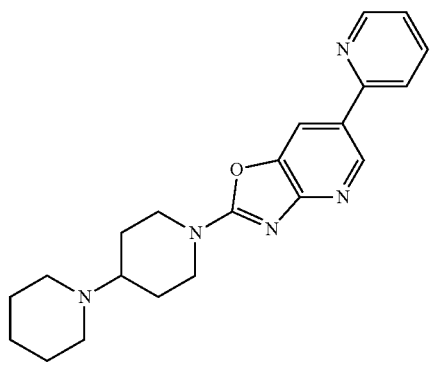 |
| 148 | 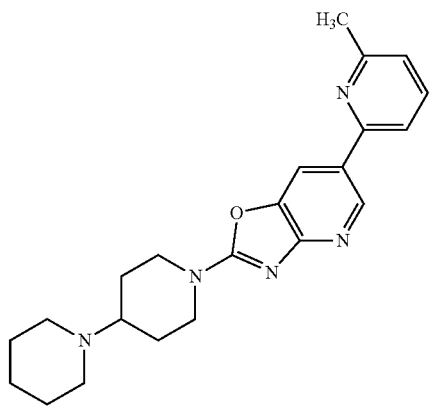 |

| Compound No. | Structure |
|---|---|
| 149 | 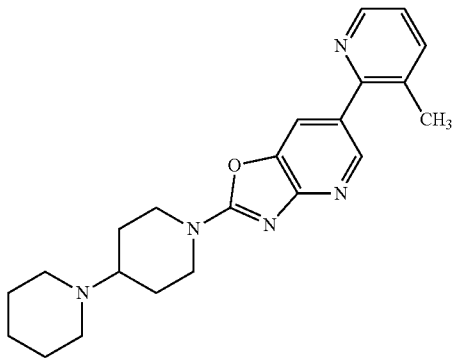 |
| 150 | 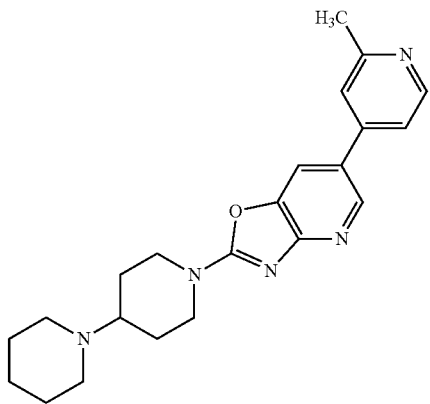 |
| 151 | 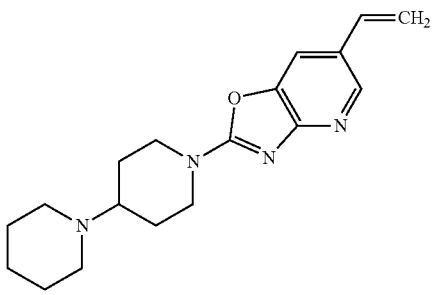 |
| 152 | 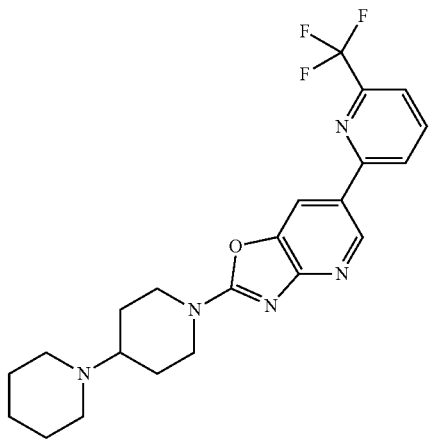 |

-continued
| Compound No. | Structure |
|---|---|
| 153 | 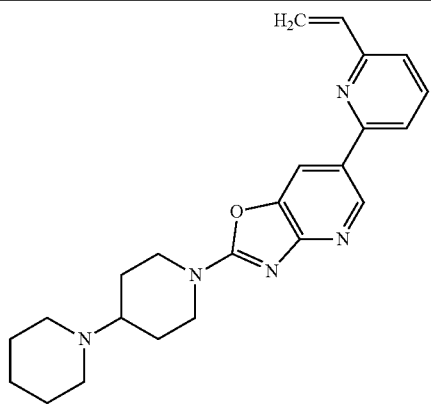 |
| 154 | 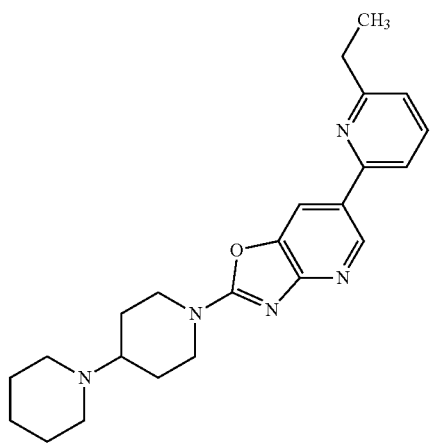 |
| 155 | 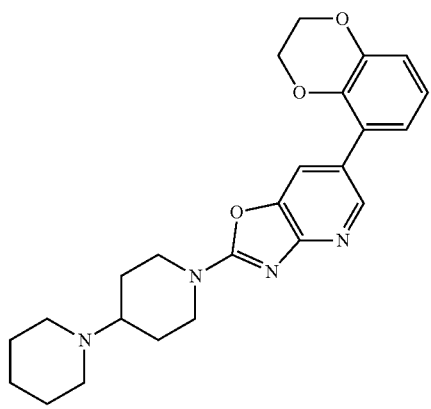 |

| Compound No. | Structure |
|---|---|
| 156 | 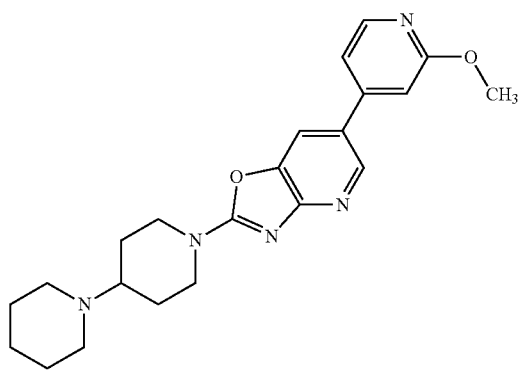 |
| 157 | 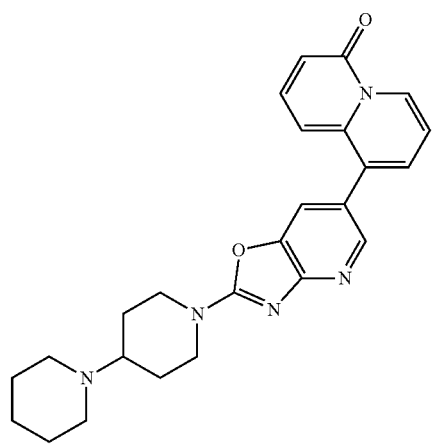 |
| 158 | 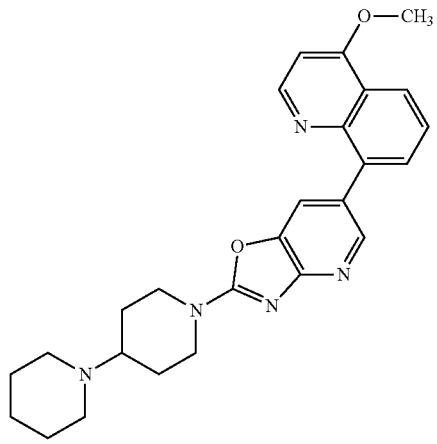 |

-continued
| Compound No. | Structure |
|---|---|
| 159 | 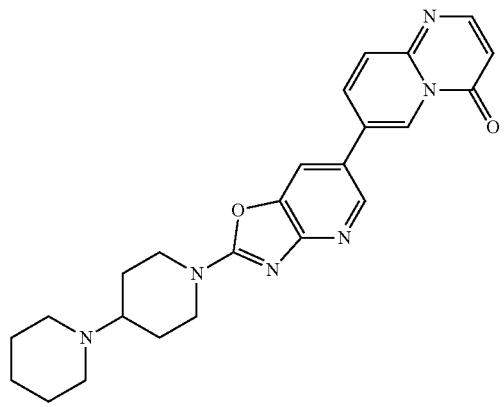 |
| 160 | 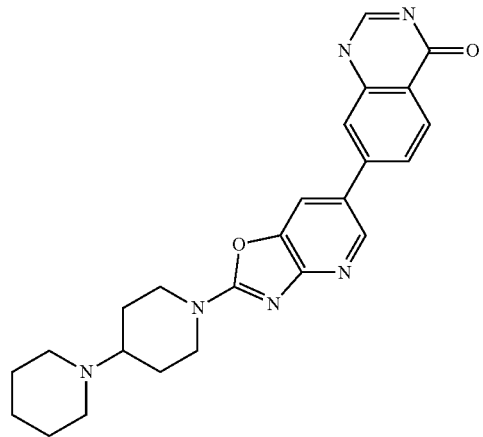 |
| 161 | 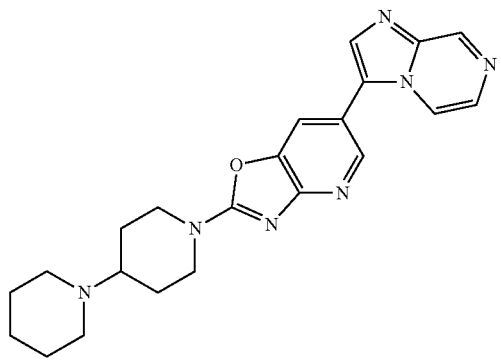 |
| 162 | 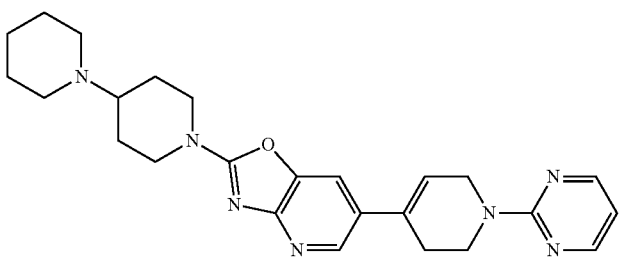 |

-continued
| Compound No. | Structure |
|---|---|
| 163 | 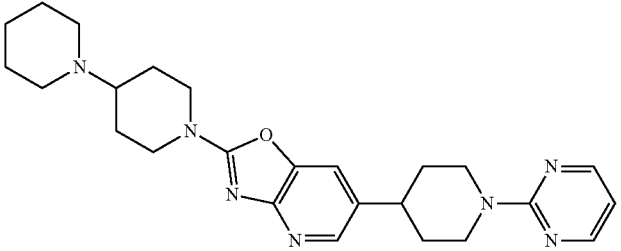 |
| 164 | 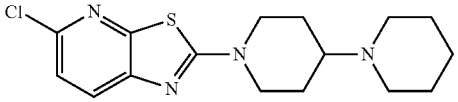 |
| 165 | 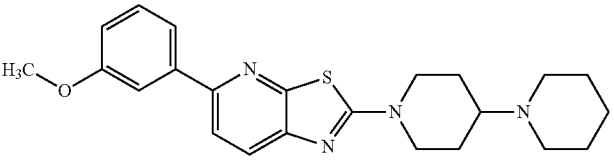 |
| 166 | 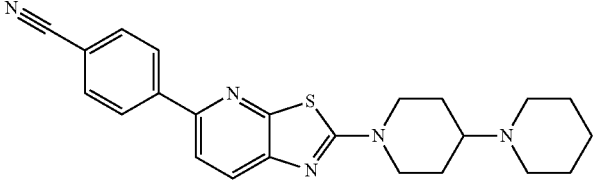 |
| 167 | 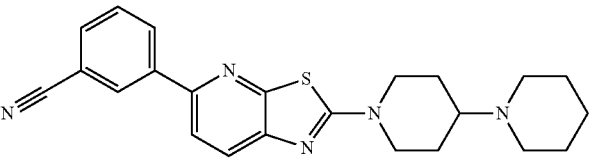 |
| 168 | 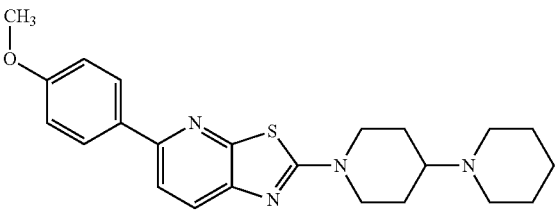 |
| 169 | 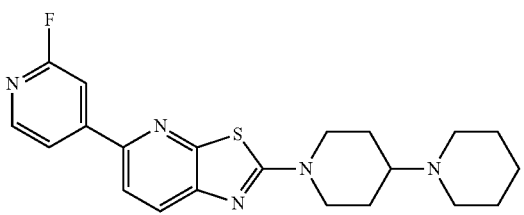 |

-continued

| Compound No. | Structure |
|---|---|
| 170 | 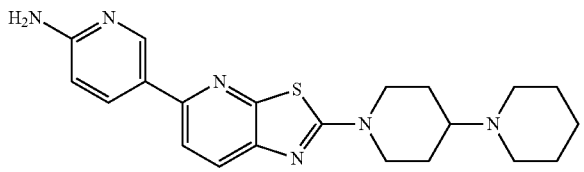 |
| 171 | 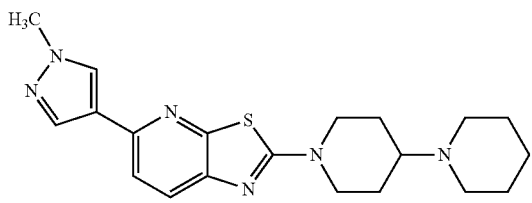 | and pharmaceutically acceptable salts, solvates, esters and prodrugs thereof.

Methods for Making the Compounds of Formula (I)

Methods useful for making the Compounds of Formula (I) are set forth in the Examples below and generalized in Schemes 1-3. Alternative synthetic pathways and analogous structures will be apparent to those skilled in the art or organic synthesis.

Scheme 1 shows a method useful for making the Compounds of Formula (I), wherein $X^5$ is —N—.

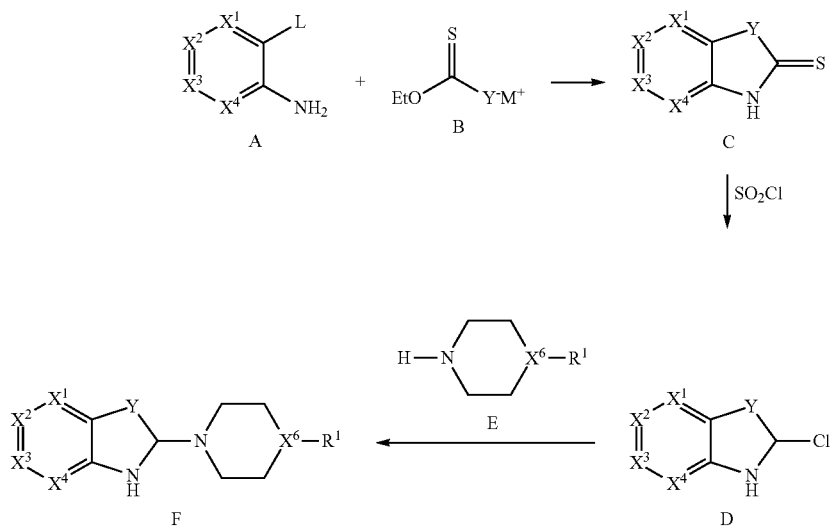

wherein L is Cl or Br; M is Na or K; and $X^1$-$X^4$, $X^6$, Y and $A^1$ are defined above for the Compounds of Formula (I).

A heteroaryl compound of formula A can be reacted with a salt of formula B to form bicyclic intermediates of formula C. A compound of formula C is then reacted with thionyl chloride to provide the chloro intermediates of formula D. Finally, a compound of formula D is reacted with an amino compound of formula E to provide the compounds of formula E, which correspond to the Compounds of Formula (I), wherein $X^5$ is N.

Scheme 2 shows a method useful for making the Compounds of Formula (I), wherein $X^5$ is —N—, one of $X^1$-$X^4$ is —C(Q)-, and W is a bond.

Scheme 2

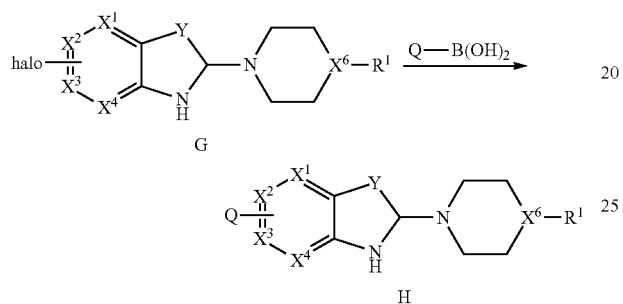

wherein $X^1$-$X^4$, $X^6$, Q, Y and $R^1$ are defined above for the Compounds of Formula (I)

A compound of formula G (which corresponds to the compounds of formula F wherein one of groups $X^1$-$X^4$ is —C(halo)-) can be coupled with a group Q via a Suzuki type coupling reaction with a boronic acid derivative of formula Q-B(OH)$_2$. The product (H) of this coupling reaction, corresponds to the Compounds of Formula (I), wherein $X^5$ is —N—, one of $X^1$-$X^4$ is —C(Q)-, and W is a bond.

Scheme 3 shows a method useful for making the Compounds of Formula (I), wherein $X^5$ is —N—, one of $X^1$-$X^4$ is —C(Q)-, Q is a nitrogen-containing heterocycloalkyl group joined by a ring N atom, and W is a bond.

Scheme 3

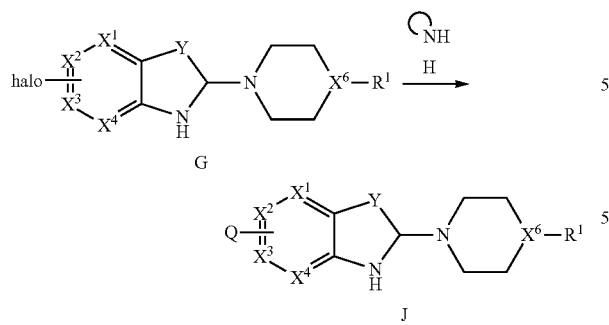

wherein Q is a nitrogen-containing heterocycloalkyl group joined by a ring N atom and $X^1$-$X^4$, $X^6$, Y and $R^1$ are defined above for the Compounds of Formula (I).

A compound of formula G can be coupled with a nitrogen-containing heterocycloalkyl moiety of formula H to provide the compounds of formula J, which correspond to the Compounds of Formula (I), wherein $X^5$ is —N—, one of $X^1$-$X^4$ is —C(Q)-, Q is a nitrogen-containing heterocycloalkyl group joined by a ring N atom, and W is a bond.

The starting materials and reagents depicted in Schemes 1-3 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of compounds of Formula (I) may require the need for the protection of certain functional groups (i.e., derivatization for the purpose of chemical compatibility with a particular reaction condition). Suitable protecting groups for the various functional groups of the compounds of formula I and methods for their installation and removal may be found in Greene et al., *Protective Groups in Organic Synthesis*, Wiley-Interscience, New York, (1999).

EXAMPLES

The following examples exemplify illustrative examples of compounds of the present invention and are not to be construed as limiting the scope of the disclosure. Alternative mechanistic pathways and analogous structures within the scope of the invention may be apparent to those skilled in the art.

General Methods

The starting materials and reagents used in preparing compounds described are either available from commercial suppliers such as Aldrich Chemical Co. (Wisconsin, USA) and Acros Organics Co. (New Jersey, USA) or were prepared using methods well-known to those skilled in the art of organic synthesis. All commercially purchased solvents and reagents were used as received. LCMS analysis was performed using an Applied Biosystems API-100 mass spectrometer equipped with a Shimadzu SCL-10A LC column: Altech platinum C18, 3 um, 33 mm×7 mm ID; gradient flow: 0 minutes, 10% CH$_3$CN; 5 minutes, 95% CH$_3$CN; 7 minutes, 95% CH$_3$CN; 7.5 minutes, 10% CH$_3$CN; 9 minutes, stop. Flash column chromatography was performed using Selecto Scientific flash silica gel, 32-63 mesh. Analytical and preparative TLC was performed using Analtech Silica gel GF plates. Chiral HPLC was performed using a Varian PrepStar system equipped with a Chiralpak OD column (Chiral Technologies).

Example 1

Preparation of Compound 1

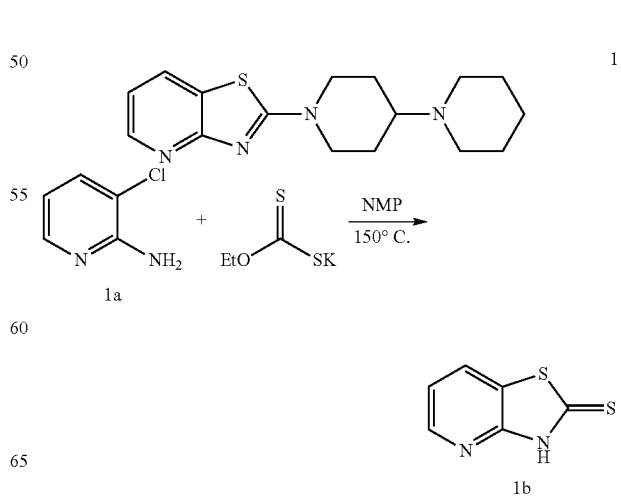

A solution of 2-amino-3-chloropyridine 1a (4.0 g, 31.1 mmol) and potassium ethylxanthate (7.48 g, 46.67 mmol, 1.5 equiv) in 30 mL N-methyl-2-pyrrolidinone was heated to 150° C. overnight. After the reaction mixture was cooled to room temperature, 5 mL acetic acid was added followed by 250 mL H₂O. The mixture was stirred for 10 min and filtered. The solid residue was triturated with 1:1 EtOH:H₂O and dried to yield 1b (3.43 g) as a brown powder.

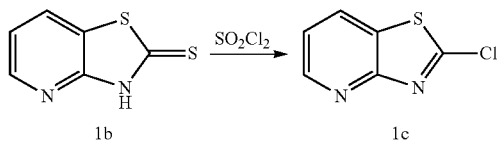

A slurry of 1b (250 mg, 1.49 mmol) in SO₂Cl₂ (1.2 mL, 14.9 mmol, 10 equiv) was stirred at room temperature overnight. The slurry was quenched by the addition of H₂O and extracted with EtOAc (2×15 mL). The combined organic layer was washed with 1 N NaOH, followed by brine, dried over Na₂SO₄, filtered, concentrated and dried to yield 1c (136 mg) as a brown powder.

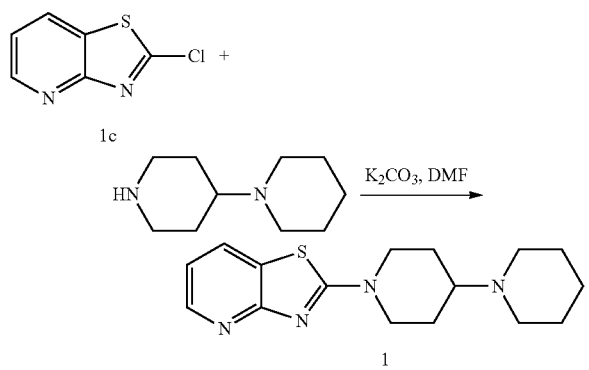

To a solution of 1c (166 mg, 0.97 mmol) in DMF (1 mL) was added K₂CO₃ (268 mg, 1.94 mmol, 2 equiv) and 4-piperidinopiperidine (206 mg, 1.2 mmol, 1.2 equiv). The reaction mixture was allowed to stir at room temperature overnight after which it was diluted with H₂O and extracted with EtOAc (2×10 mL). The combined organic layer was washed with brine, dried over Na₂SO₄, filtered and concentrated to yield after purification by flash chromatography (2% MeOH/CH₂Cl₂) 1 (129 mg) as a brown powder.

Example 2

Preparation of Compound 2

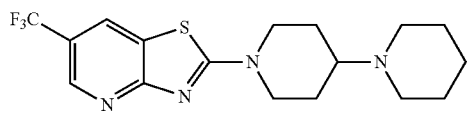

Compound 2 was prepared using the method described to make compound 1 but using 2-amino-3-chloro-5-trifluoromethylpyridine.

Example 3

Preparation of Compound 3

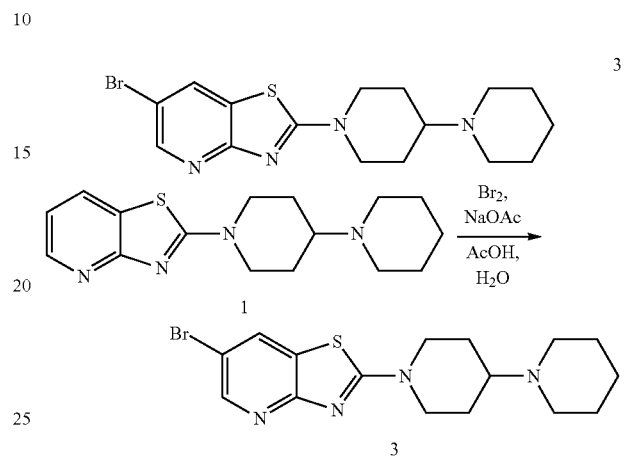

To a solution of 1 (129 mg, 0.427 mmol) in 2 mL of 50% aqueous acetic add was added NaOAc (420 mg, 512 mmol, 12 equiv) followed by dropwise addition of Br₂ (24 □L, 0.47 mmol, 1.1 equiv). The reaction mixture was stirred for 15 min after which 1 drop of Br₂ was added and stirred for 10 min. After MS showed no more staffing material, the reaction was cooled to 0° C. and basified to pH 12 using 34% eq. NaOH. The mixture was extracted with EtOAc (2×10 mL), washed with brine, dried over Na₂SO₄, filtered and concentrated to yield crude product which was purified by flash chromatography (2% to 4% MeOH/CH₂Cl₂) to yield 42 mg of 3.

Example 4

Preparation of Compound 4

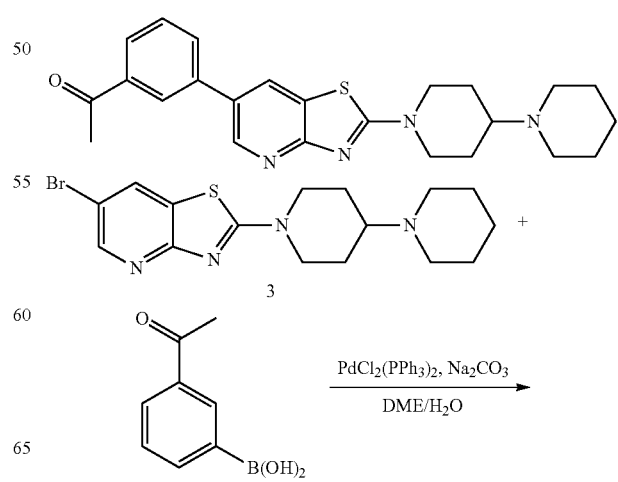

-continued

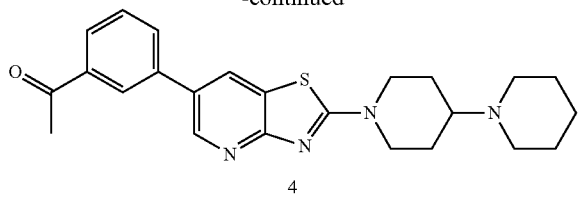

4

A mixture of 3 (40 mg, 0.105 mmol), 3-acetylphenyl boronic acid (31 mg, 0.19 mmol, 1.8 equiv), PdCl$_2$(PPh$_3$)$_2$ (8 mg, 0.01 mmol, 10 mol %) and Na$_2$CO$_3$ (33 mg, 0.315 mmol, 3 equiv) in 3.0 mL, of DME/H$_2$O (4:1) was heated to 100° C. overnight. After cooling, the reaction mixture was loaded onto a flash column and purified by eluting with 2% to 4% MeOH/CH$_2$Cl$_2$ to yield 10 mg of 4 as a yellow powder.

Example 5

Preparation of Compound 5

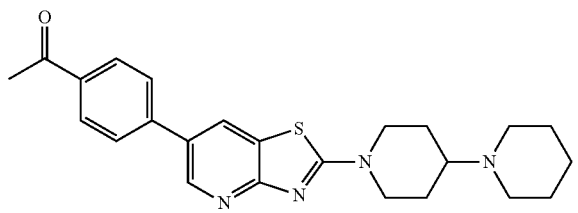

5

Compound 5 was prepared using the method described to make compound 4 but using 4-acetylphenyl boronic acid.

Example 6

Preparation of Compound 6

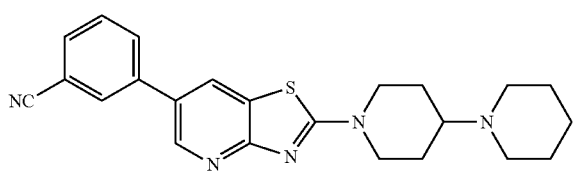

6

Compound 6 was prepared using the method described to make compound 4 but using 3-cyanophenyl boronic acid.

Example 7

Preparation of Compound 7

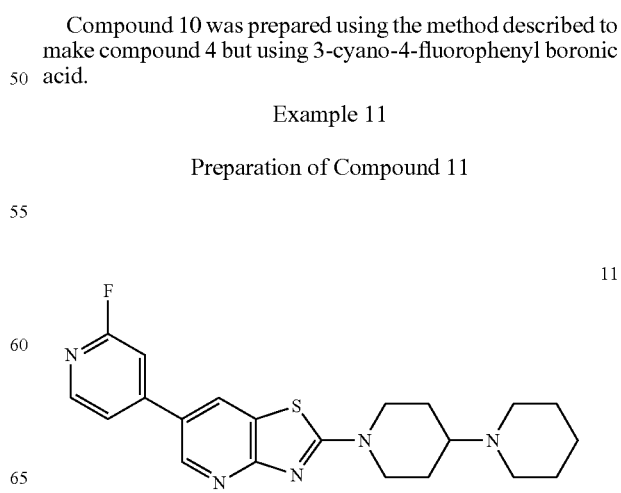

7

Compound 7 was prepared using the method described to make compound 4 but using 4-cyanophenyl boronic acid.

Example 8

Preparation of Compound 8

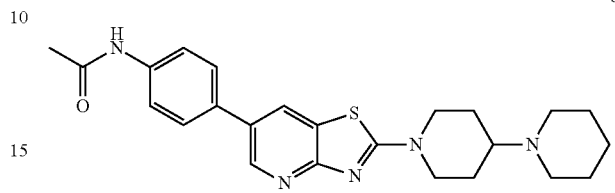

8

Compound 8 was prepared using the method described to make compound 4 but using 4-acetamidophenyl boronic acid.

Example 9

Preparation of Compound 9

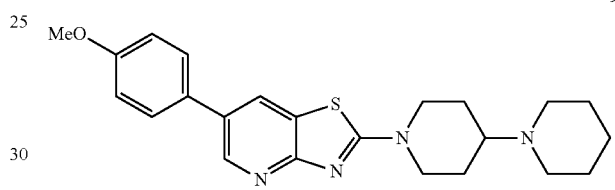

9

Compound 9 was prepared using the method described to make compound 4 but using 4-methoxyphenyl boronic acid.

Example 10

Preparation of Compound 10

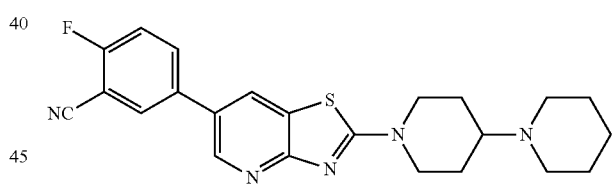

10

Compound 10 was prepared using the method described to make compound 4 but using 3-cyano-4-fluorophenyl boronic acid.

Example 11

Preparation of Compound 11

11

Compound 11 was prepared using the method described to make compound 4 but using 2-fluoropyridine-4-boronic acid.

Example 12

Preparation of Compound 12

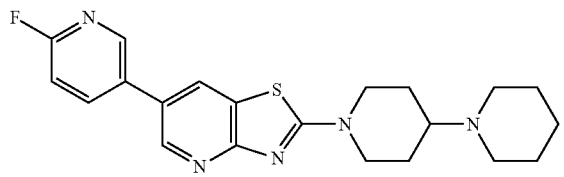

12

Compound 12 was prepared using the method described to make compound 4 but using 2-fluoropyridine-5-boronic acid.

Example 13

Preparation of Compound 13

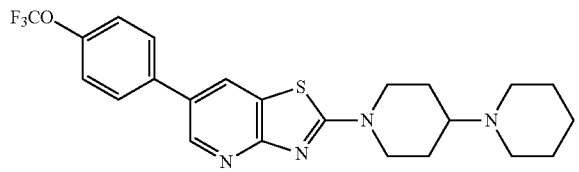

13

Compound 13 was prepared using the method described to make compound 4 but using 4-trifluoromethoxyphenyl boronic acid.

Example 14

Preparation of Compound 14

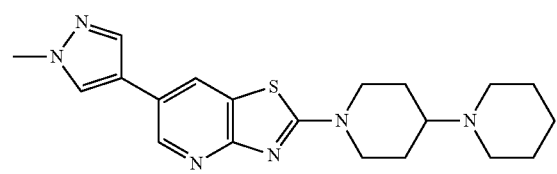

14

Compound 14 was prepared using the method described to make compound 4 but using 1-methylpyrazel-4-boronic acid.

Example 15

Preparation of Compound 15

15

Compound 15 was prepared using the method described to make compound 4 but using 2-fluoropyridine-3-boronic acid.

Example 16

Preparation of Compound 16

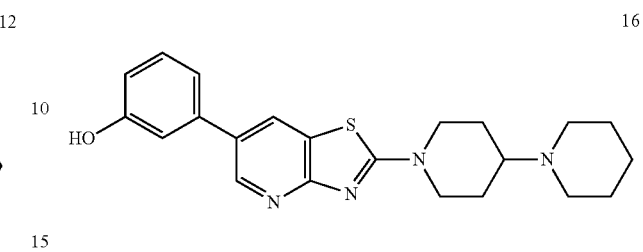

16

Compound 16 was prepared using the method described to make compound 4 but using 3-hydroxyphenyl boronic acid.

Example 17

Preparation of Compound 17

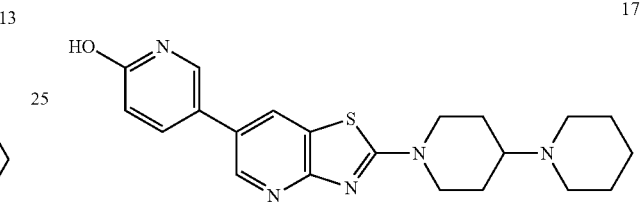

17

Compound 17 was prepared using the method described to make compound 4 but using 2-hydroxypyridine-5-boronic acid.

Example 18

Preparation of Compound 18

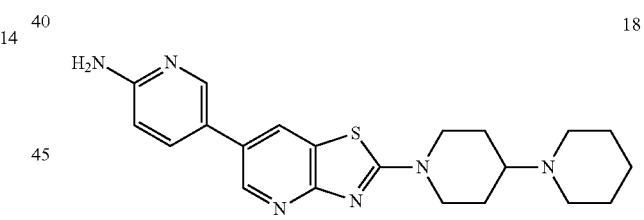

18

Compound 1 was prepared using the method described to make compound 4 but using 2-aminopyridine-5-boronic acid.

Example 19

Preparation of Compound 19

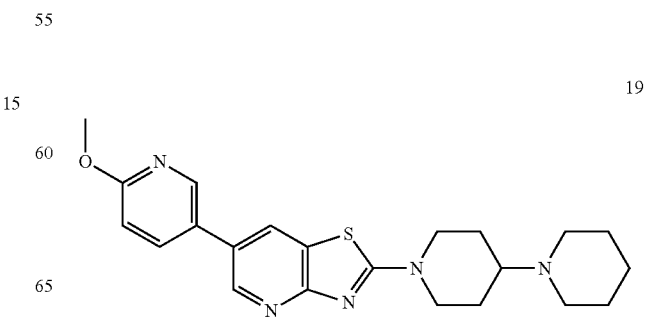

19

Compound 19 was prepared using the method described to make compound 4 but using 2-methoxypyridine-5-boronic acid.

Example 20

Preparation of Compound 20

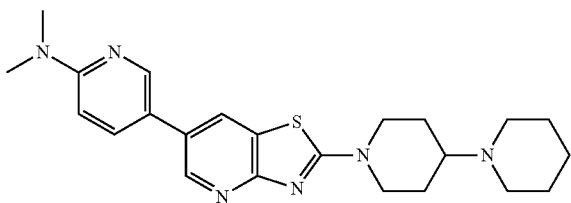

20

Compound 20 was prepared using the method described to make compound 4 but using 2-dimethylaminopyridine-5-boronic acid.

Example 21

Preparation of Compound 21

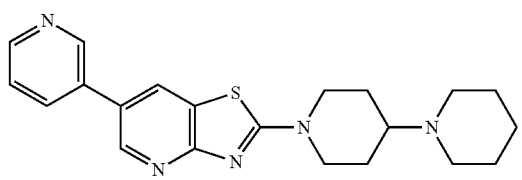

21

Compound 21 was prepared using the method described to make compound 4 but using pyridine-3-boronic acid.

Example 22

Preparation of Compound 22

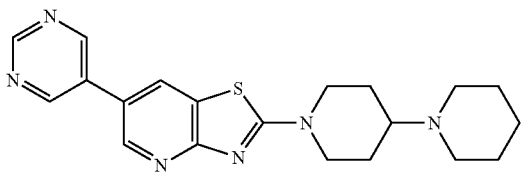

22

Compound 22 was prepared using the method described to make compound 4 but using pyrimidine-5-boronic acid.

Example 23

Preparation of Compound 23

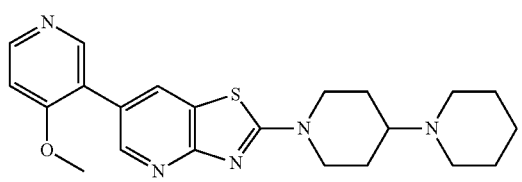

23

Compound 23 was prepared using the method described to make compound 4 but using 4-methoxypyridine-3-boronic acid.

Example 24

Preparation of Compound 24

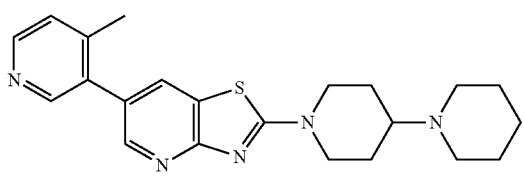

24

Compound 24 was prepared using the method described to make compound 4 but using 4-methylpyridine-3-boronic acid.

Example 25

Preparation of Compound 25

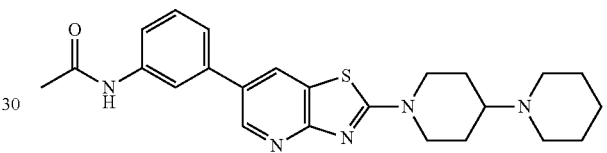

25

Compound 25 was prepared using the method described to make compound 4 but using 3-acetamidophenyl boronic acid.

Example 26

Preparation of Compound 26

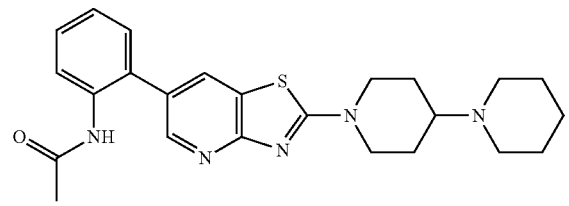

26

Compound 26 was prepared using the method described to make compound 4 but using 2-acetamidophenyl boronic acid.

Example 27

Preparation of Compound 27

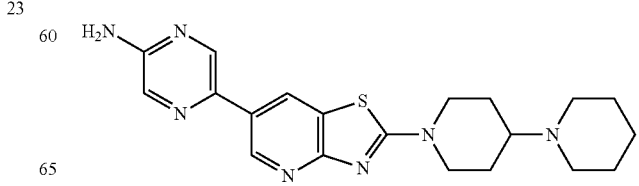

27

Compound 27 was prepared using the method described to make compound 4 but using 2-pyrazine-5-boronic acid.

Example 28

Preparation of Compound 28

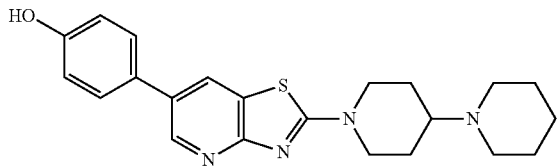

Compound 28 was prepared using the method described to make compound 4 but using 4-hydroxyphenyl boronic acid.

Example 29

Preparation of Compound 29

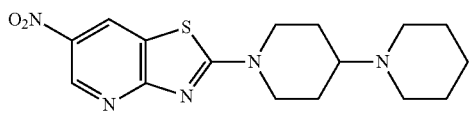

To a solution of 1 (0.51 g, 17 mmol) in AcOH (1.8 mL) was added HNO₃ (fuming, 0.9 mL). The reaction mixture was heated to 100° C. with stirring for 2 hours. After cooled to 0° C., the reaction mixture was neutralized with saturated NaHCO₃, and extracted with CH₂Cl₂ (3×50 mL). The combined organic layer was washed with brine, dried over Na₂SO₄, filtered and concentrated to yield after purification by flash chromatography (2 MeOH/CH₂Cl₂) 29 (0.16 g) as a yellow solid.

Example 30

Preparation of Compound 30

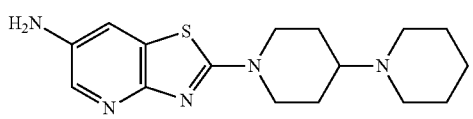

To a solution of 29 (0.15 g, 0.43 mmol) in AcOH (1 mL) was added Zn dust (0.27 g, 4.3 mmol). The reaction mixture was allowed to stir at room temperature overnight after which it was filtered from the solid. The filtrate was concentrated to yield after purification by flash chromatography (3% MeOH/CH₂Cl₂) 30 (0.10 g) as a brown solid.

Example 31

Preparation of Compound 31

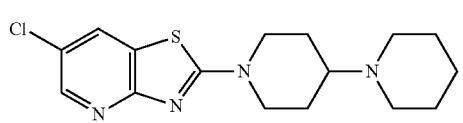

To a solution of 30 (80 mg, 0.25 mmol) in HCl (18%, 1.5 mL) at 0° C. was added a solution of NaNO₂ (26 mg, 0.38 mmol) in water (1 mL) and CuCl (38 mg). The reaction mixture was heated to 60° C. with stirring for 2 h. After cooled to room temperature, the reaction mixture was neutralized with saturated NaHCO₃, and extracted with CH₂Cl₂ (2×20 mL). The combined organic layer was washed with brine, dried over Na₂SO₄, filtered and concentrated to yield after purification by flash chromatography (2% MeOH/CH₂Cl₂) 31 (61 mg) as a beige solid.

Example 32

Preparation of Compound 32

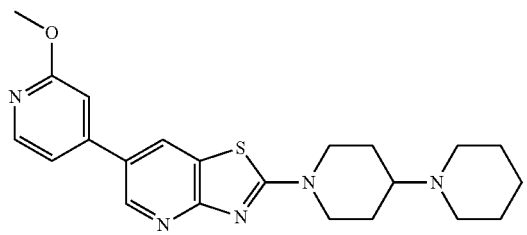

Compound 32 was prepared using the method described to make compound 4 but using 2-methoxypyridine-4-boronic acid.

Example 33

Preparation of Compound 33

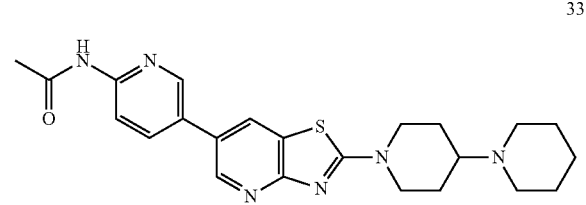

Compound 33 was prepared using the method described to make compound 4 but using 2-acetamidopyridine-5-boronic acid.

Example 34

Preparation of Compound 34

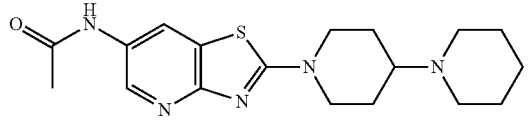

To a solution of 30 (16 mg, 0.05 mmol) and Et$_3$N (10 mg, 0.1 mmol, 2.0 equiv) in CH$_2$Cl$_2$ (0.5 mL) was added acetyl chloride (4 mg, 0.06 mmol, 1.2 equiv) at 0° C. After 1 h the reaction was quenched by the addition of sat. aq. NaHCO$_3$, extracted with CH$_2$Cl$_2$ (2×3 mL), dried over Na$_2$SO$_4$, filtered and concentrated. The crude reaction mixture was purified by preparative TLC (10% MeOH/CH$_2$Cl$_2$) to yield 4 mg of the desired compound 34.

Example 35

Preparation of Compound 35

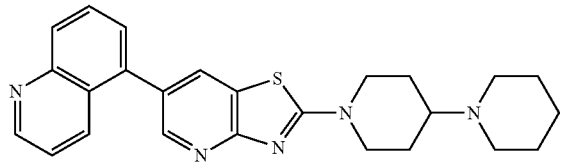

Compound 35 was prepared using the method described to make compound 4 but using 5-quinoline boronic acid.

Example 36

Preparation of Compound 36

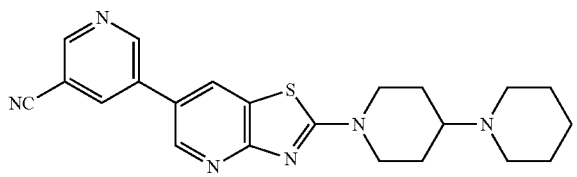

Compound 36 was prepared using the method described to make compound 4 but using 3-cyanopyridine-5-boronic acid.

Example 37

Preparation of Compound 37

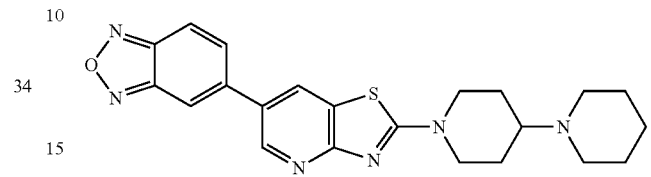

Compound 37 was prepared using the method described to make compound 4 but using 2,1,3-benzoxadiazole-5-boronic acid.

Example 38

Preparation of Compound 38

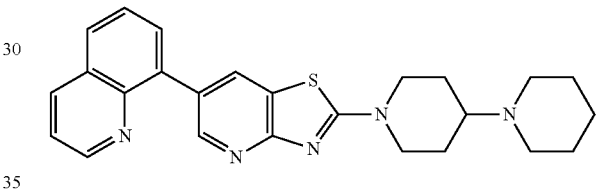

Compound 38 was prepared using the method described to make compound 4 but using 8-quinoline boronic acid.

Example 39

Preparation of Compound 39

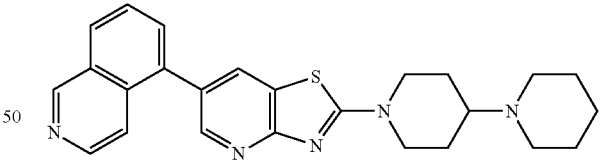

Compound 39 was prepared using the method described to make compound 4 but using 5-isoquinoline boronic acid.

Example 40

Preparation of Compound 40

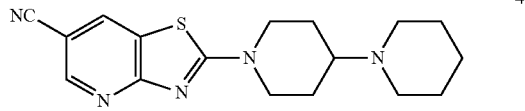

A mixture of 3 (100 mg, 0.26 mmol), Zn(CN)₂ (51 mg, 0.52 mmol, 2 equiv), Pd(OAc)₂ (12 mg, 0.05 mmol, 20 mol %), (±)-BINAP (32 mg, 0.05 mmol, 20 mol %) and KO'Bu (58 mg, 0.52 mmol, 12 equiv) in 3.0 mL of toluene was heated to 165° C. in a microwave for 40 min. After cooling, the reaction mixture was loaded onto a flash column and purified by eluting with 2% to 6% MeOH/CH₂Cl₂ to yield 45 mg of 40 as a off white powder.

Example 41

Preparation of Compound 41

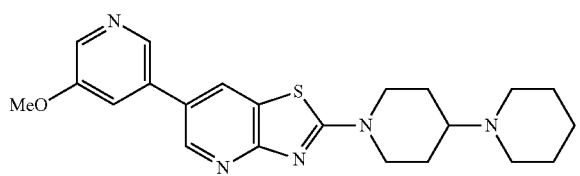

41

Compound 41 was prepared using the method described to make compound 4 but using 3-methoxypyridine-5-boronic acid.

Example 42

Preparation of Compound 42

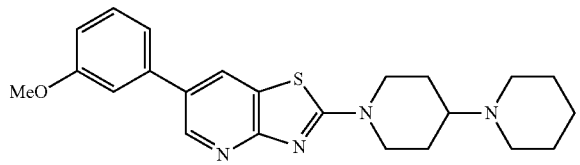

42

Compound 42 was prepared using the method described to make compound 4 but using 3-methoxyphenyl boronic acid.

Example 43

Preparation of Compound 43

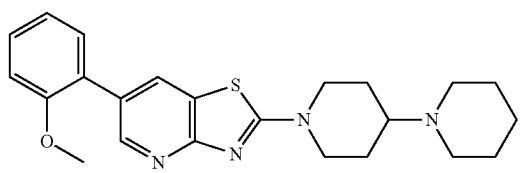

43

Compound 43 was prepared using the method described to make compound 4 but using 2-methoxyphenyl boronic acid.

Example 44

Preparation of Compound 44

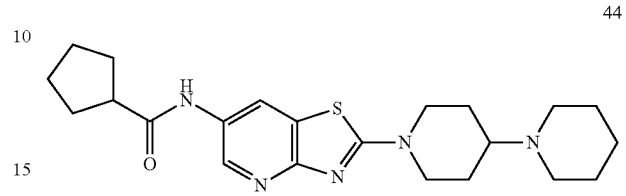

44

Compound 44 was prepared using the method described to make compound 34 but using cyclopentanecarbonyl chloride and compound 30.

Example 45

Preparation of Compound 45

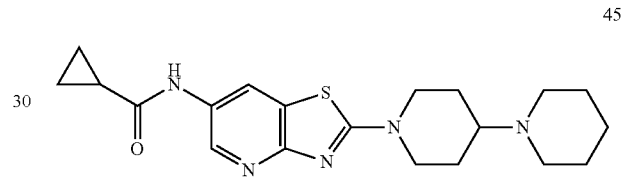

45

Compound 45 was prepared using the method described to make compound 34 but using cyclopropanecarbonyl chloride and compound 30.

Example 46

Preparation of Compound 46

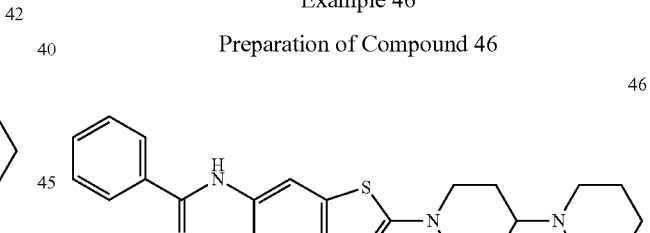

46

Compound 46 was prepared using the method described to make compound 34 but using benzoylchloride and compound 30.

Example 47

Preparation of Compound 47

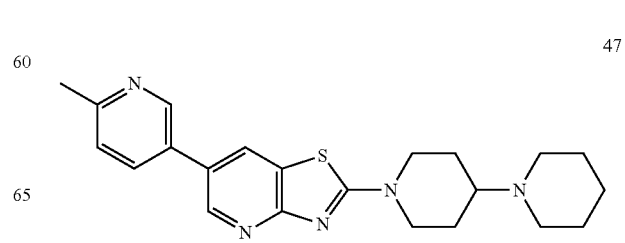

47

Compound 47 was prepared using the method described to make compound 4 but using 2-methylpyridine-5-boronic acid.

Example 48

Preparation of Compound 48

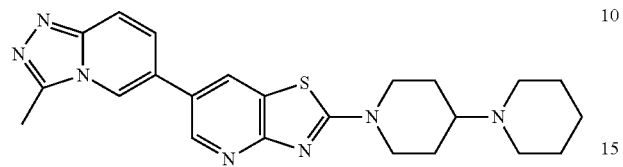
48

Compound 48 was prepared using the method described to make compound 4 but using 3-methyl-1,2,4-triazo[4,3-a]pyridine-4-boronic acid.

Example 49

Preparation of Compound 49

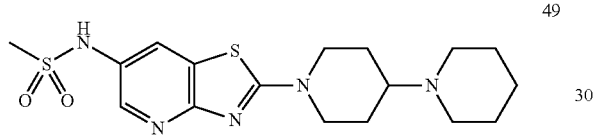
49

Compound 49 was prepared using the method described to make compound 34 but using methylsulfonylchloride and compound 30.

Example 50

Preparation of Compound 50

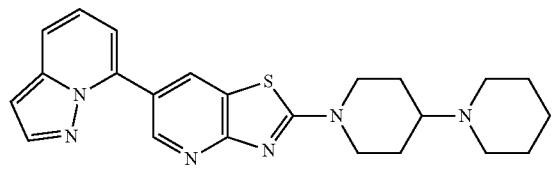
50

Compound 50 was prepared using the method described to make compound 4 but using pyrazolo[1,5-a]pyridine-6-boronic acid.

Example 51

Preparation of Compound 51

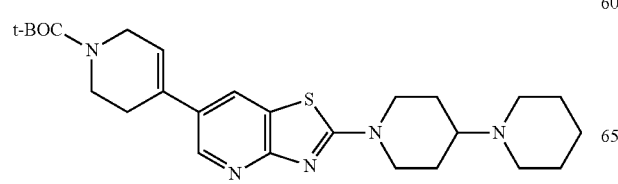
51

Compound 51 was prepared using the method described to make compound 4 but using N-Boc-1,2,3,6-tetrahydropyridine-4-boronic acid pinacol ester.

Example 52

Preparation of Compound 52

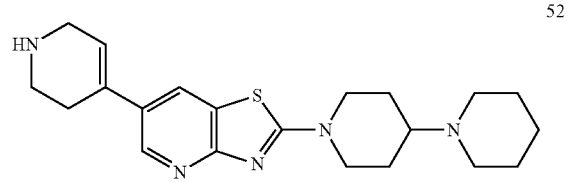
52

A solution of compound 51 (215 mg, 0.44 mmol) and trifluoroacetic acid (4.0 mL) in $CH_2Cl_2$ (10 mL) was refluxed for 1 h. After cooling to room temperature, the reaction mixture was neutralized with sat. aq. $NaHCO_3$ and extracted with EtOAc (3×15 mL). The combined organic extracts was washed with brine, dried over $Na_2SO_4$, filtered and concentrated to afford the desired product 52 (150 mg).

Example 53

Preparation of Compound 53

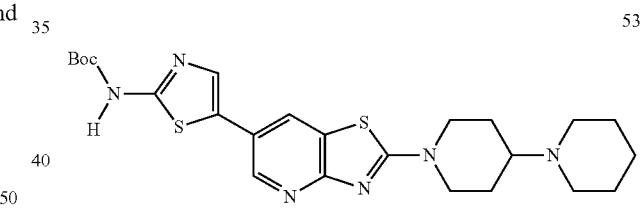
53

A mixture of 3 (100 mg, 0.26 mmol), N-Boc-2-aminothiazolotributyltin (218 mg, 0.45 mmol, 1.7 equiv), and $Pd(PPh_3)_4$ (52 mg, 0.045 mmol, 10 mol %) in 2.0 mL of DMF was heated to 140° C. in a microwave for 50 min. After cooling, the reaction mixture was loaded onto a flash column and purified by eluting with 1.5% $MeOH/CH_2Cl_2$ to yield 20 mg of 53 as a yellow solid.

Example 54

Preparation of Compound 54

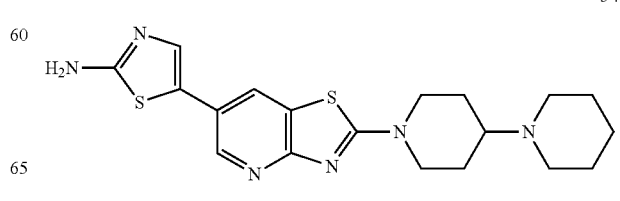
54

Compound 54 was prepared using the method described to make compound 52 but using 53.

Example 55

Preparation of Compound 55

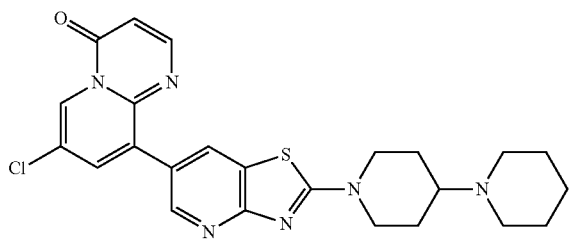

55

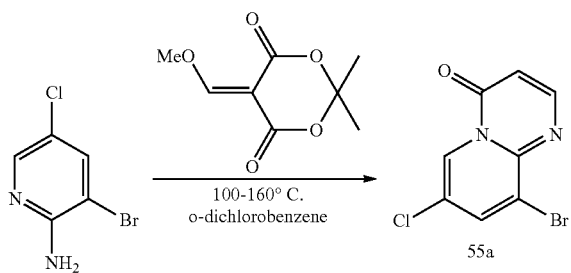

A mixture of 2-amino-3-bromo-5-chloropyridine (2.07 g, 10 mmol) and 5-(methoxymethylene)-2,2-dimethyl-1,3-dioxane-4,6-dione (1.86 g, 10 mmol) in 20 ml o-dichlorobenzene was heated to 100° C. for 1 h then 160° C. for 4 h. The reaction mixture was cooled to room temperature and then loaded on to a 220 g silica gel column. The column was eluted with 0-40% EtOAc/Hexanes to yield product 55a (1.84 g, 70%).

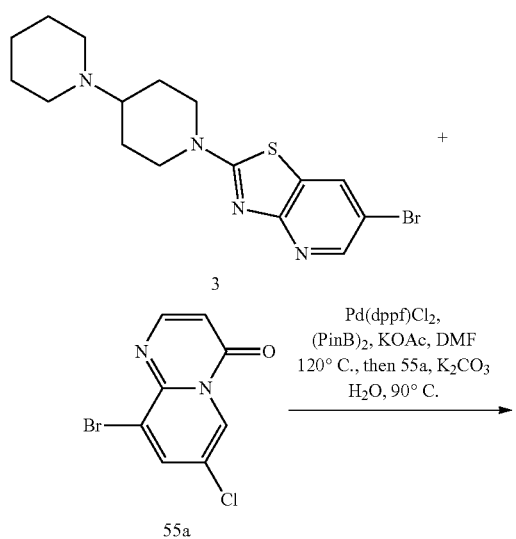

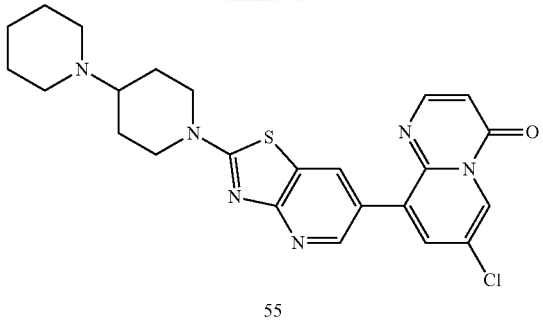

55

A mixture of Compound 3 (100 mg, 0.26 mmol), bis(pinacolato)diboron (66 mg), and KOAc (74 mg), Pd(dppf)Cl$_2$ (21 mg) in DMF (3 ml) was heated to 90° C. for 2 h. The reaction was cooled to room temperature. 55a (200 mg), K$_2$CO$_3$ (74 mg), and water (1 ml) was added. The mixture was again heated to 90° C. overnight. The reaction was cooled to room temperature and diluted with 1 N aq. NaOH solution. The mixture was extracted with EtOAc, dried over Na$_2$SO$_4$ and concentrated. The residue was purified by HPLC (Gilson) to give 55 (70 mg).

Example 56

Preparation of Compound 56

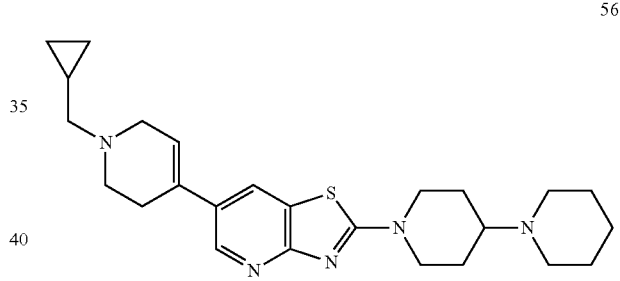

56

To a solution of compound 52 (20 mg, 0.052 mmol) and K$_2$CO$_3$ (14 mg, 0.104 mmol, 2.0 equiv) in CH$_3$CN (3.0 mL) was added bromomethylcyclopropane (7 mg, 0.052 mmol, 1.0 equiv) dropwise. The reaction was stirred at room temperature overnight. After the reaction was complete, the mixture was diluted with H$_2$O (5 mL) and extracted with CH$_2$Cl$_2$ (2×10 mL). The combined organic extracts was washed with brine, dried over Na$_2$SO$_4$, filtered and concentrated to afford the crude product which was purified by flash chromatography (5% to 10% MeOH/CH$_2$Cl$_2$) to yield compound 56.

Example 57

Preparation of Compound 57

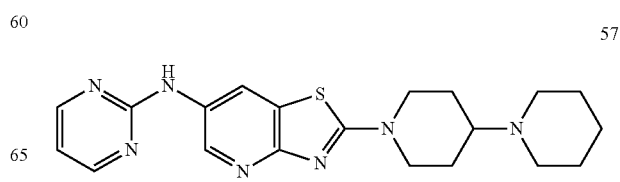

57

A mixture of 30 (100 mg, 0.32 mmol), 2-bromopyrimidine (100 mg, 0.64 mmol, 2 equiv) in 2.0 mL of DMF was heated to 140° C. in a microwave for 55 min. After cooling, the reaction mixture was loaded onto a flash column and purified by eluting with 2.5% MeOH/CH₂Cl₂ to yield 18 mg of 57 as a yellow solid.

Example 58

Preparation of Compound 58

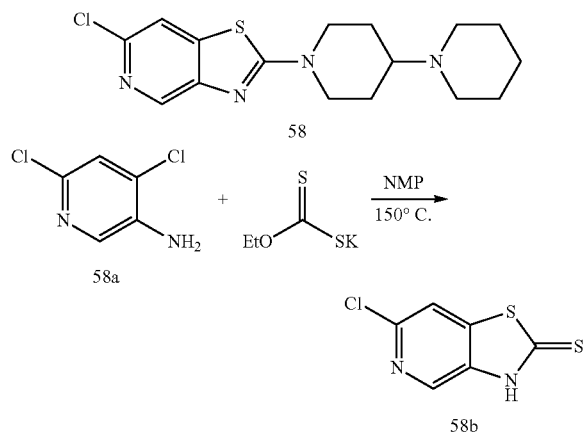

Compound 58b was prepared using the method described to make compound 1b but using 5-amino-2,4-dichloropyridine.

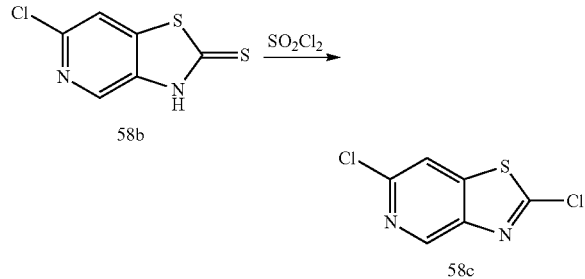

Compound 58c was prepared using the method described to make compound 1c.

Compound 58 was prepared using the method described to make compound 1

Example 59

Preparation of Compound 59

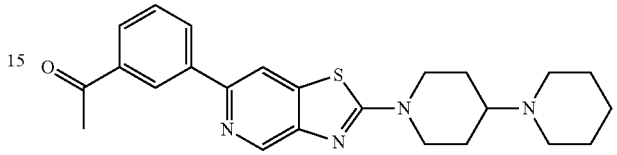

A mixture of 58 (100 mg, 0.3 mmol), 3-acetylphenyl boronic acid (87 mg, 0.53 mmol, 1.8 equiv), Pd(PPh₃)₄ (35 mg, 0.03 mmol, 10 mol %) and Na₂CO₃ (94 mg, 0.89 mmol, 3 equiv) in 3.0 mL of DME/H₂O (4:1) was heated to 140° C. in a microwave for 40 min. After cooling, the reaction mixture was loaded onto a flash column and purified by eluting with 2% to 6% MeOH/CH₂Cl₂ to yield 79 mg of 59 as a yellow powder.

Example 60

Preparation of Compound 60

Compound 60 was prepared using the method described to make compound 59 but using 4-cyanophenyl boronic acid.

Example 61

Preparation of Compound 61

Compound 61 was prepared using the method described to make compound 59 but using 2-fluoro-5-pyridine boronic acid.

Example 62

Preparation of Compound 62

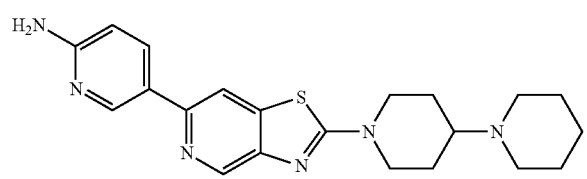

62

Compound 62 was prepared using the method described to make compound 59 but using 2-aminopyridine-5 boronic acid pinacol ester.

Example 63

Preparation of Compound 63

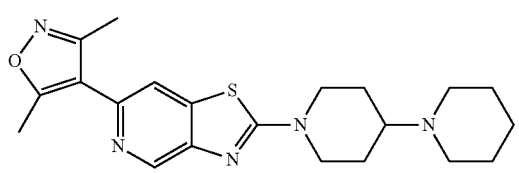

63

Compound 63 was prepared using the method described to make compound 59 but using 3,5-dimethylisoxazole-4-boronic acid.

Example 64

Preparation of Compound 64

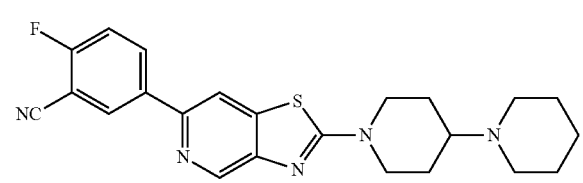

64

Compound 64 was prepared using the method described to make compound 59 but using 3-cyano-4-fluorophenyl boronic acid.

Example 65

Preparation of Compound 65

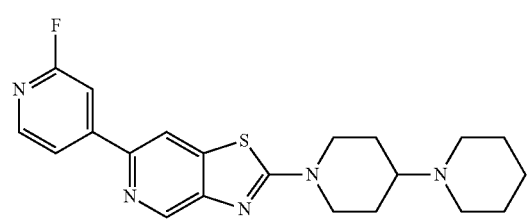

65

Compound 65 was prepared using the method described to make compound 59 but using 2-fluoropyridine-4-boronic acid.

Example 66

Preparation of Compound 66

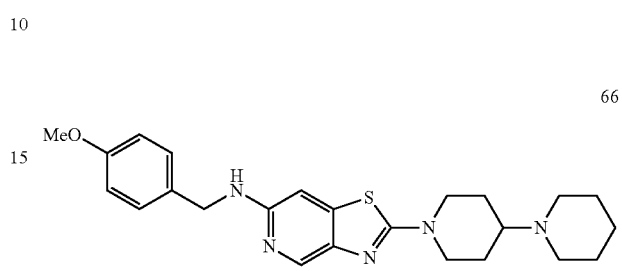

66

A mixture of 58 (100 mg, 0.3 mmol), 4-methoxybenzyl amine (47 µL, 0.36 mmol, 1.2 equiv), Pd(OAc)$_2$ (3 mg, 0.012 mmol, 4 mot %), (±)-BINAP (8 mg, 0.012 mmol, 4 mol %) and NaO$^t$Bu (40 mg, 0.42 mmol, 1.4 equiv) in 3.0 mL of toluene was heated to 150° C. in a microwave for 40 min. After cooling, the reaction mixture was loaded onto a flash column and purified by eluting with 2% to 6% MeOH/CH$_2$Cl$_2$ to yield 58 mg of 66 as a yellow powder.

Example 67

Preparation of Compound 67

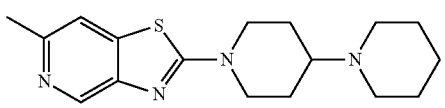

67

Compound 67 was prepared using the method described to make compound 59 but using trimethylboroxine.

Example 68

Preparation of Compound 68

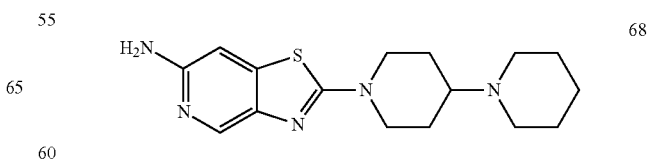

68

To a solution of 66 (50 mg, 0.114 mmol) in CH$_2$Cl$_2$ (3.0 mL) was added trifluoroacetic acid (1 mL) and triflic acid (60 mL, 0.46 and, 4.0 equiv). The reaction was stirred at room temperature for 1 h after which the reaction mixture was neutralized with sat. aq. NaHCO$_3$, extracted with CH$_2$Cl$_2$ (3×10 mL), dried over Na$_2$SO$_4$, filtered and concentrated. The crude reaction mixture was purified by flash chromatography (2% to 8% MeOH/CH$_2$Cl$_2$) to yield 20 mg of 68.

Example 69

Preparation of Compound 69

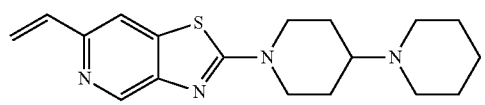

Compound 69 was prepared using the method described to make compound 59 but using vinyl boronic acid pinacol ester.

Example 70

Preparation of Compound 70

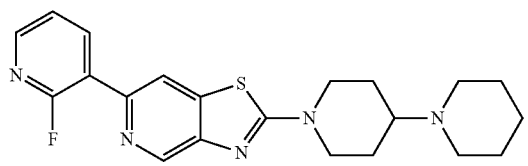

Compound 70 was prepared using the method described to make compound 59 but using 2-fluoropyridine-3-boronic acid.

Example 71

Preparation of Compound 71

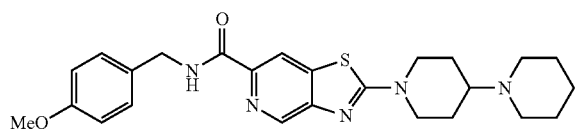

To a mixture of 58 (100 mg, 0.3 mmol), 4-methoxybenzyl amine (156 µL, 1.2 mmol, 4.0 equiv), Pd(OAc)$_2$ (14 mg, 0.06 mmol, 20 mol %), imidazole (11 mg, 0.15 mmol, 0.5 equiv) and Mo(CO)$_6$ (79 mg, 0.3 mmol, 1.0 equiv) in 3.0 mL of THF in a sealed microwave vial was added DBU (135 µL, 0.9 mmol, 3.0 equiv) dropwise. The reaction vessel was heated to 170° C. for 60 min. After cooling, the reaction mixture was loaded onto a flash column and purified by eluting with 2% to 6% MeOH/CH$_2$Cl$_2$ to yield 19 mg of 71.

Example 72

Preparation of Compound 72

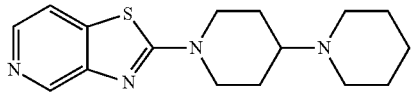

Compound 72 was obtained as a byproduct from the above carbamoylation reaction.

Example 73

Preparation of Compound 73

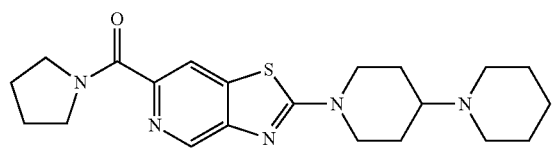

Compound 73 was prepared using the method described to make compound 71 but using pyrrolidine.

Example 74

Preparation of Compound 74

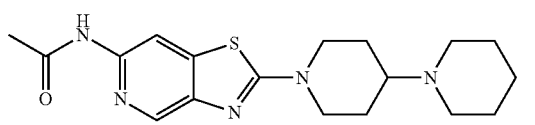

To a solution of 68 (125 mg, 0.39 mmol) and Et$_3$N (109 µL, 0.78 mmol, 2.0 equiv) in CH$_2$Cl$_2$ (5 mL) was added acetyl chloride (28 µL, 0.39 mmol, 1.0 equiv) at 0° C. After 1 h the reaction was quenched by the addition of sat. aq. NaHCO$_3$, extracted with CH$_2$Cl$_2$ (2×5 mL), dried over Na$_2$SO$_4$, filtered and concentrated. The crude reaction mixture was purified by preparative TLC (10% MeOH/CH$_2$Cl$_2$) to yield 13 mg of the desired compound 74.

Example 75

Preparation of Compound 75

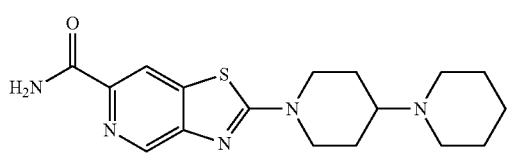

Compound 75 was prepared using the method described to make compound 68.

Example 76

Preparation of Compound 76

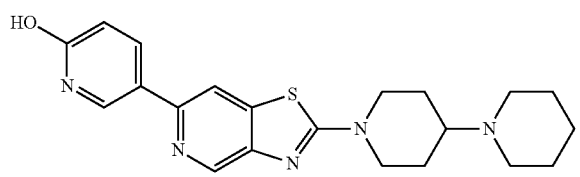
76

Compound 76 was prepared using the method described to make compound 59 but using 2-hydroxypyridine-5-boronic acid pinacol ester.

Example 77

Preparation of Compound 77

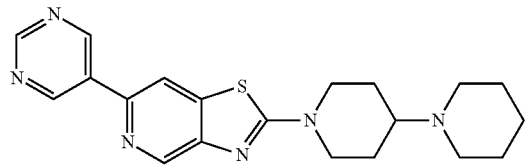
77

Compound 77 was prepared using the method described to make compound 59 but using pyrimidine-5-boronic acid.

Example 78

Preparation of Compound 78

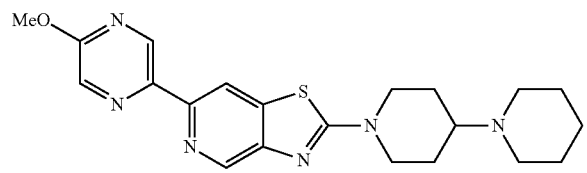
78

Compound 78 was prepared using the method described to make compound 59 but using 5-methoxypyrazine-2-boronic acid pinacol ester.

Example 79

Preparation of Compound 79

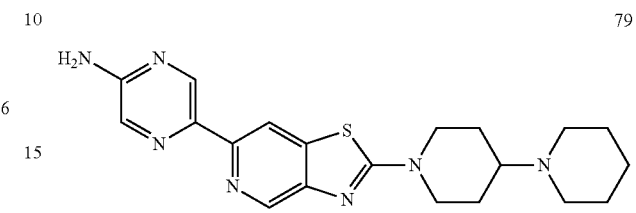
79

Compound 79 was prepared using the method described to make compound 59 but using 5-aminopyrazine-2-boronic acid pinacol ester.

Example 80

Preparation of Compound 80

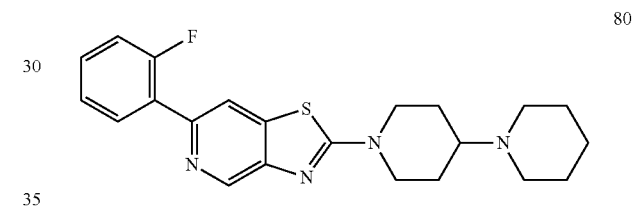
80

Compound 80 was prepared using the method described to make compound 59 but using 2-fluorobenzene boronic acid.

Example 81

Preparation of Compound 81

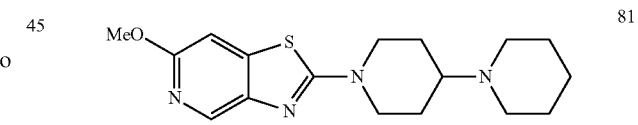
81

Compound 81 was prepared using the method described to make compound 66 but using methanol.

Example 82

Preparation of Compound 82

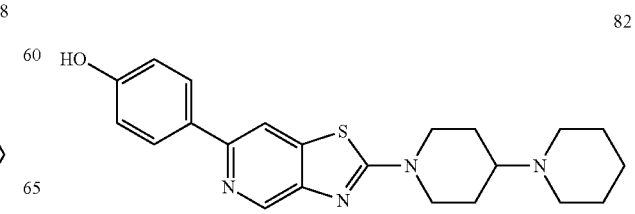
82

Compound 82 was prepared using the method described to make compound 59 but using 4-hydroxyphenyl boronic acid.

Example 83

Preparation of Compound 83

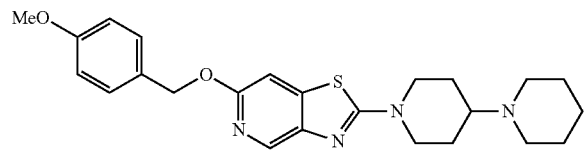

83

Compound 83 was prepared using the method described to make compound 66 but using 4-methoxybenzyl alcohol.

Example 84

Preparation of Compound 84

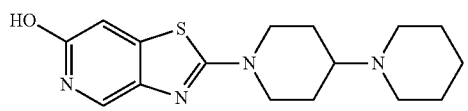

84

Compound 84 was prepared using the method described to make compound 68.

Example 85

Preparation of Compound 85

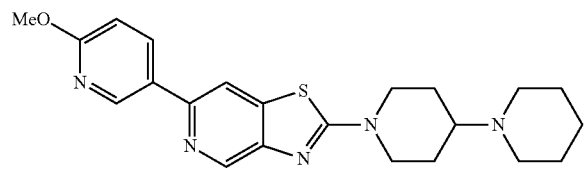

85

Compound 85 was prepared using the method described to make compound 59 but using 6-methoxypyridine-3-boronic acid.

Example 86

Preparation of Compound 86

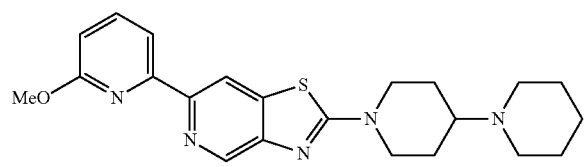

86

Compound 86 was prepared using the method described to make compound 59 but using 6-methoxypyridine-2-boronic acid pinacol ester.

Example 87

Preparation of Compound 87

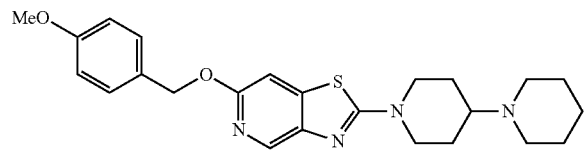

87

Compound 87 was prepared using the method described to make compound 59 but using 2-acetamidopyridine-5-boronic acid pinacol ester.

Example 88

Preparation of Compound 88

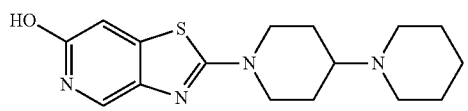

88

Compound 88 was prepared using the method described to make compound 59 but using 2-methoxypyridine-4-boronic acid.

Example 89

Preparation of Compound 89

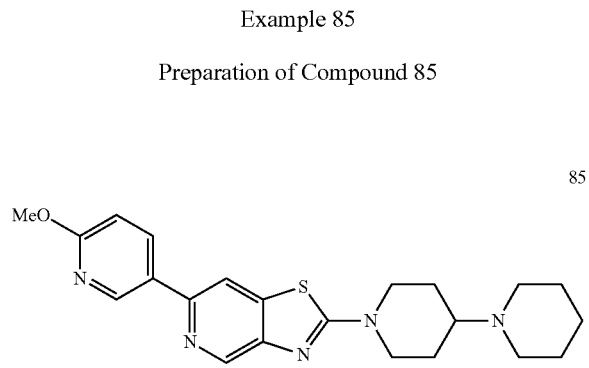

89

Compound 89 was prepared using the method described to make compound 66 but using $Zn(CN)_2$.

Example 90

Preparation of Compound 90

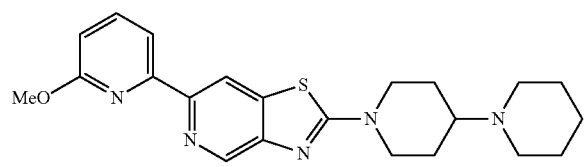

90

Compound 90 was prepared using the method described to make compound 59 but using 3-cyano-5-pyridine boronic acid pinacol ester.

Example 91

Preparation of Compound 91

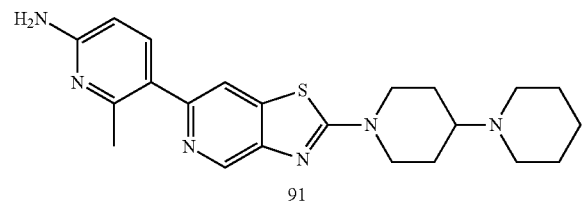
91

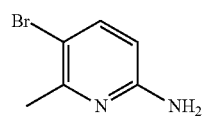
91a

+

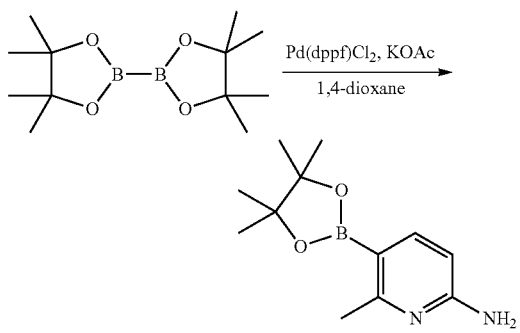

To a dry flask was added 6-amino-3-bromo-2-methylpyridine 91a (1.0 g, 5.35 mmol), potassium acetate (1.58 g, 16.05 mmol, 3.0 equiv), bis(pinacolato)diboron (1.49 g, 5.88 mmol, 1.1 equiv) and 1,4-dioxane (25 mL). Nitrogen was bubbled through the solution for 10 minutes, at which time dichloro[1,1-bis(diphenylphosphino)ferrocene]palladium (H) dichloromethane adduct (218 mg, 0.27 mmol, 0.05 equiv) was added. The reaction mixture was refluxed at 115° C. overnight under nitrogen. After cooling to room temperature, EtOAc (30 mL) was added and the resulting slurry was sonicated and filtered. Additional EtOAc (20 mL) was used to wash the solids. The combined organic extracts was concentrated and purified by flash chromatography (30%-50% EtOAc/hexanes) to yield 91b as a pale black solid (420 mg).

Compound 91 was prepared using the method described to make compound 59 but using compound 91b.

Example 92

Preparation of Compound 92

92

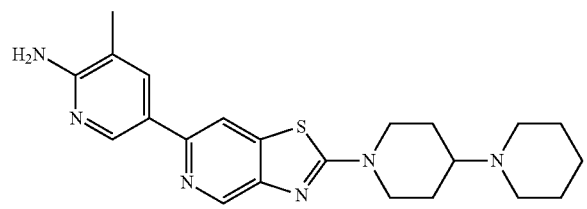

The boronic acid pinacol ester was prepared using the method described to make compound 91b but using 2-amino-5-bromo-3-methylpyridine. Compound 92 was prepared using the method described to make compound 59.

Example 93

Preparation of Compound 93

93

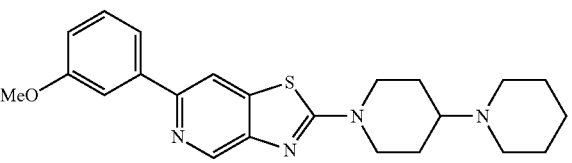

Compound 93 was prepared using the method described to make compound 59 but using 3-methoxybenzene boronic acid.

Example 94

Preparation of Compound 94

94

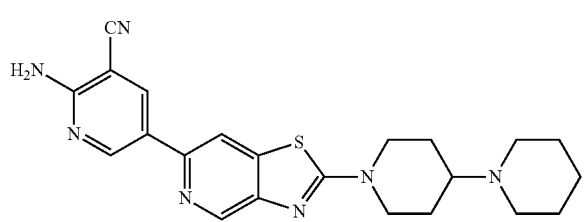

The boronic acid pinacol ester was prepared using the method described to make compound 91b but using 2-amino-5-bromo-3-cyanopyridine. Compound 94 was prepared using the method described to make compound 59.

Example 95

Preparation of Compound 95

95

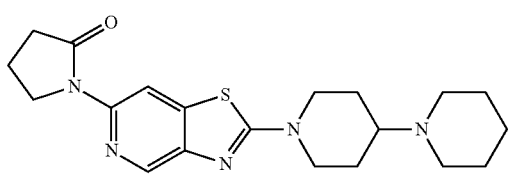

Compound 95 was prepared using the method described to make compound 66 but using 2-pyrrolidinone.

Example 96

Preparation of Compound 96

96

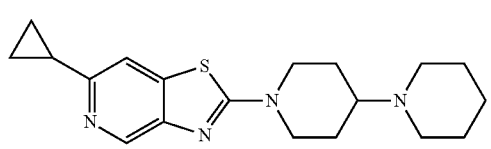

Compound 96 was prepared using the method described to make compound 59 but using cyclopropyl boronic acid.

Example 97

Preparation of Compound 97

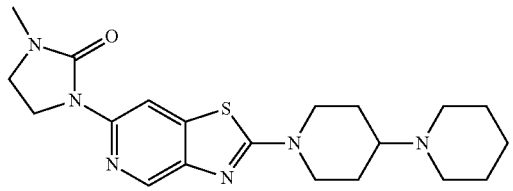
97

Compound 97 was prepared using the method described to make compound 66 but using 1-methyl-2-imidazolidinone.

Example 98

Preparation of Compound 98

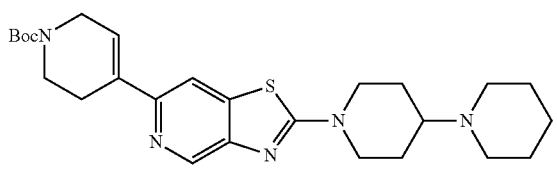
98

Compound 98 was prepared using the method described to make compound 59 but using N-Boc-1,2,3,6-tetrahydropyridine-4-boronic acid pinacol ester.

Example 99

Preparation of Compound 99

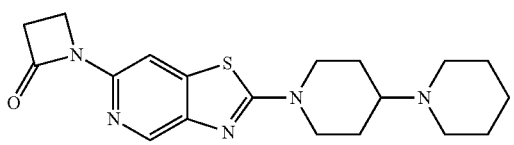
99

Compound 97 was prepared using the method described to make compound 66 but using 2-azetidinone.

Example 100

Preparation of Compound 100

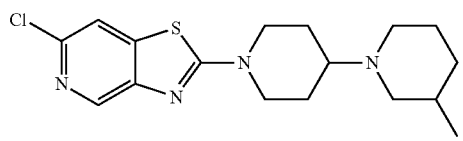
100

Compound 100 was prepared using the method described to make compound 1 but using 4-(3-methylpiperidin-1-yl)piperidine.

Example 101

Preparation of Compound 101

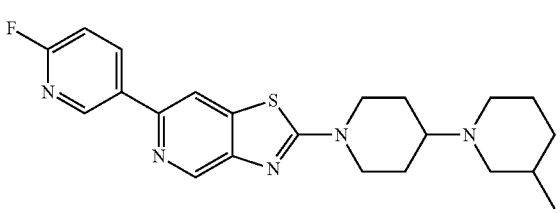
101

Compound 101 was prepared using the method described to make compound 59 but using 2-fluoro-5-pyridine boronic acid.

Example 102

Preparation of Compound 102

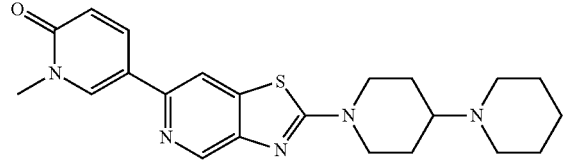
102

The boronic acid pinacol ester was prepared using the method described to make compound 91b but using 5-bromo-1-methylpyridin-2(1H)-one. Compound 102 was prepared using the method described to make compound 59.

Example 103

Preparation of Compound 103

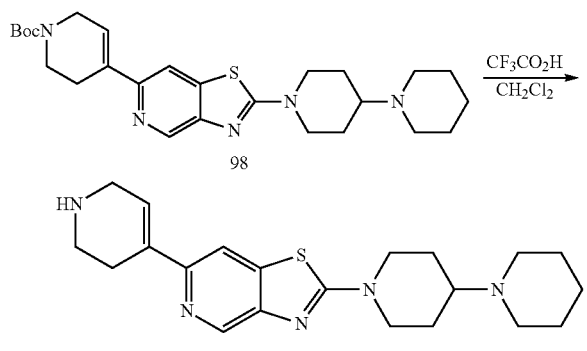

A solution of compound 98 (215 mg, 0.44 mmol) and trifluoroacetic acid (4.0 mL) in CH$_2$Cl$_2$ (10 mL) was refluxed for 1 h. After cooling to room temperature, the reaction mixture was neutralized with sat. aq. NaHCO₃ and extracted with EtOAc (3×15 mL). The combined organic extracts was washed with brine, dried over Na₂SO₄, filtered and concentrated to afford the desired product 103a (150 mg).

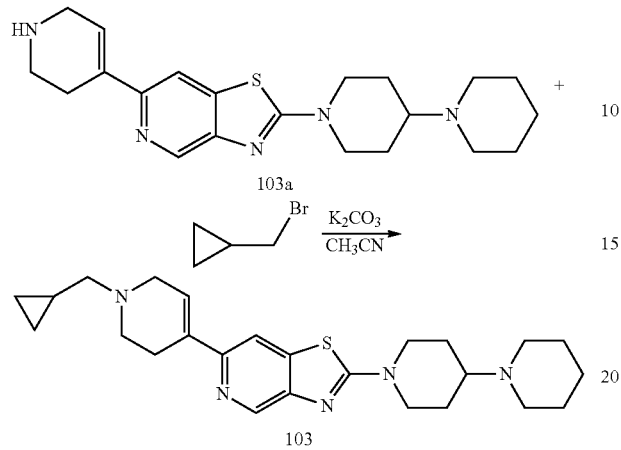

To a solution of compound 103a (20 mg, 0.052 mmol) and K₂CO₃ (14 mg, 0.104 mmol, 2.0 equiv) in CH₃CN (3.0 mL) was added bromomethylcyclopropane (7 mg, 0.052 mmol, 1.0 equiv) dropwise. The reaction was stirred at room temperature overnight. After the reaction was complete, the mixture was diluted with H₂O (5 mL) and extracted with CH₂Cl₂ (2×10 mL). The combined organic extracts was washed with brine, dried over Na₂SO₄, filtered and concentrated to afford the crude product which was purified by flash chromatography (5% to 10% MeOH/CH₂Cl₂) to yield compound 103.

Example 104

Preparation of Compound 104

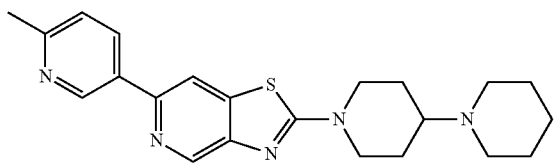

Compound 104 was prepared using the method described to make compound 59 but using 2-picoline-5-boronic acid pinacol ester.

Example 105

Preparation of Compound 105

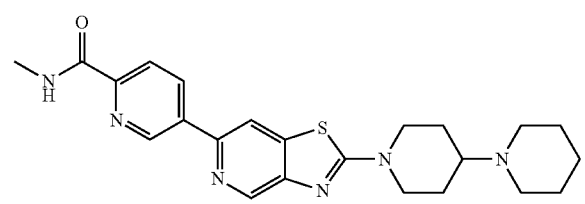

Compound 105 was prepared using the method described to make compound 59 but using 2-(N-methylamidocarboxy)-5-pyridine boronic acid pinacol ester.

Example 105

Preparation of Compound 106

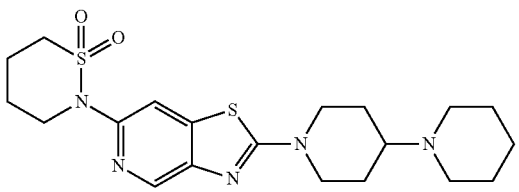

Compound 106 was prepared using the method described to make compound 66 but using 1,4-butanesultam.

Example 107

Preparation of Compound 107

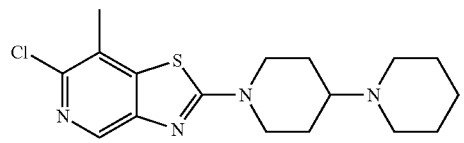

To a solution of compound 58 (100 mg, 0.3 mmol) in THF (2.0 mL), cooled to −78° C. was added lithium diisopropylamide (2.0 M solution in heptane/THF/ethylbenzene, 0.15 mL, 0.3 mmol, 1.0 equiv) dropwise. After 15 minutes of stirring was added methyl iodide (19 μL, 0.3 mmol, 1.0 equiv) dropwise. The reaction was allowed to stir for an additional 15 minutes before which it was quenched with H₂O (2.0 mL). The reaction mixture was extracted with EtOAc (2×5 mL), washed with brine, dried over Na₂SO₄, filtered and concentrated to yield compound 107 (35 mg) after purification by flash chromatography (2% to 6% MeOH/CH₂Cl₂).

Example 108

Preparation of Compound 108

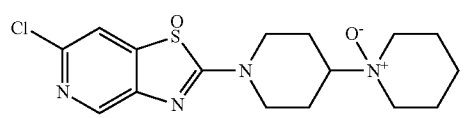

A solution of compound 58 (100 mg, 0.3 mmol) and m-CPBA (403 mg, 1.8 mmol, 6.0 equiv) in CHCl₃ (5 mL) was stirred at room temperature overnight. The crude mixture was

Example 109

Preparation of Compound 109

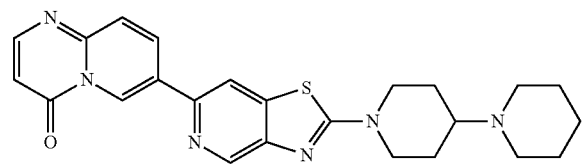
109

The bromo compound was prepared using the method described to make compound 55a but using 2-amino-5-bromopyridine. The boronic acid pinacol ester was prepared using the method described to make compound 91b but using 7-bromo-4H-pyrido[1,2-a]pyrimidin-4-one. Compound 109 was prepared using the method described to make compound 59.

Example 110

Preparation of Compound 110

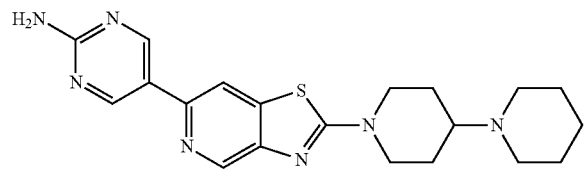
110

Compound 110 was prepared using the method described to make compound 59 but using 2-aminopyrimidine-5-boronic acid pinacol ester.

Example 111

Preparation of Compound 111

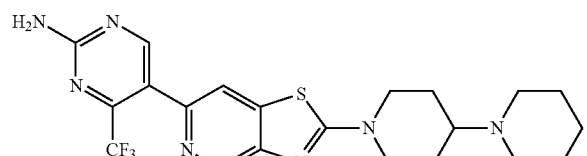
111

The boronic acid pinacol ester was prepared using the method described to make compound 91b but using 2-amino-5-bromo-4-trifluoromethylpyrimidine. Compound III was prepared using the method described to make compound 59.

Example 112

Preparation of Compound 112

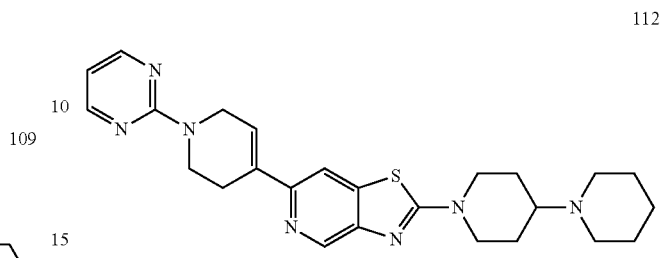
112

Compound 112 was prepared using the method described to make compound 73 but using 2-bromopyrimidine.

Example 113

Preparation of Compound 113

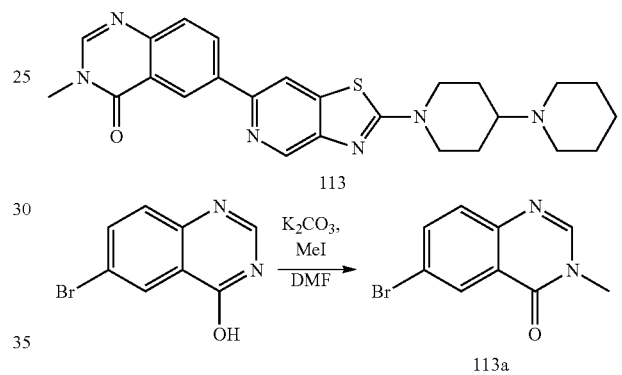
113
113a

To 6-bromoquinazolin-4-ol (1.0 g, 4.44 mmol) in 5 mL DMF was added $K_2CO_3$ (0.74 g, 5.33 mmol, 1.2 equiv) followed by MeI (0.28 mL, 4.44 mmol, 1.0 equiv). The reaction was allowed to stir at room temperature overnight. The reaction mixture was diluted with $H_2O$ (10 mL) and extracted with $Et_2O$ (2×15 mL). The combined organic extracts was washed with brine, dried over $Na_2SO_4$, filtered and concentrated. The crude was purified by flash chromatography (10% to 60% EtOAc/hexanes) to yield 414 mg of the desired product 113a.

The boronic acid pinacol ester was prepared using the method described to make compound 91b. Compound 113 was prepared using the method described to make compound 59.

Example 114

Preparation of Compound 114

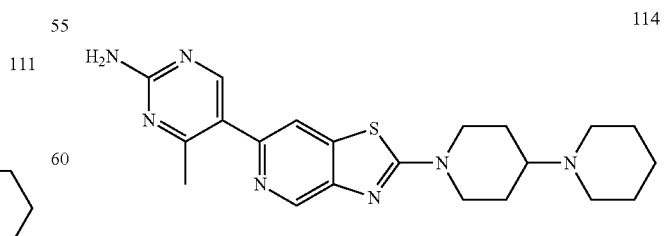
114

The boronic acid pinacol ester was prepared using the method described to make compound 91b but using 2-amino-5-bromo-4-methylpyrimidine. Compound 114 was prepared using the method described to make compound 59.

Example 115

Preparation of Compound 115

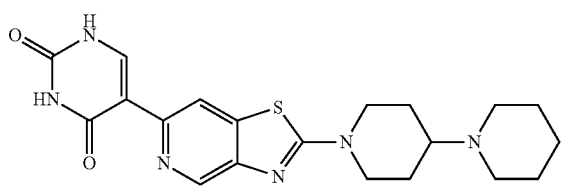

Compound 115 was prepared using the method described to make compound 59 but using 2,4-dioxo-1,2,3,4-tetrahydro-5-pyrimidinyl boronic acid.

Example 116

Preparation of Compound 116

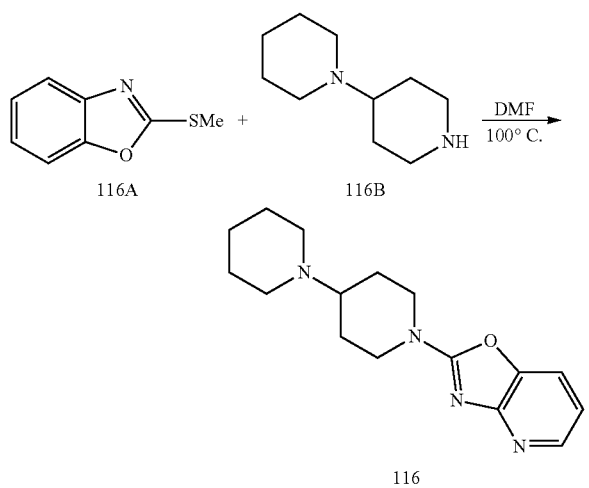

A solution of 116A (8g, 47.6 mmol) and 116B (5 g, 30 mmol) in DMF was heated at 100° C. for overnight. The reaction mixture was concentrated under vacuum and purified by column chromatography to give 116 as syrup (9 g, 99%).

Example 117

Preparation of Compound 117

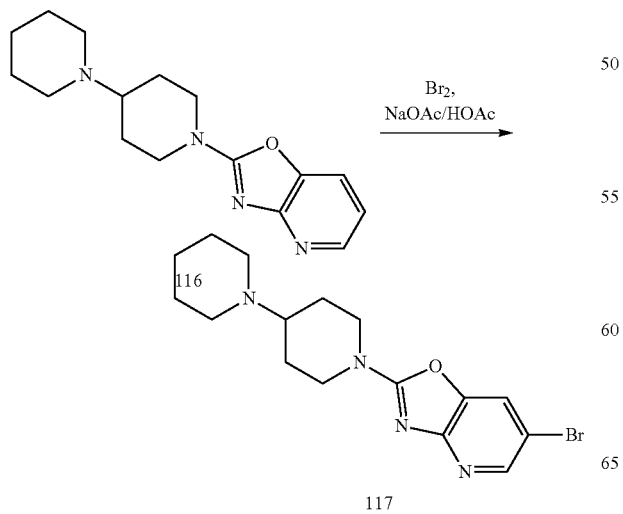

Compound 116 (2.4 g, 7.9 mmol) and NaOAc (5.1 g, 63 mmol) were taken in 50% aq. AcOH (50 ml), then $Br_2$ was added dropwise. The mixture was stirred at room temperature for 1 h and cooled to 0° C. To this mixture was added 12 N aq. NaOH solution until the pH reach 12. The mixture was extracted with EtOAc, dried over $Na_2SO_4$ and concentrated. The residue was purified by column chromatography to give 117 (2.4 g, 79%) as a brown solid.

Example 118

Preparation of Compound 118

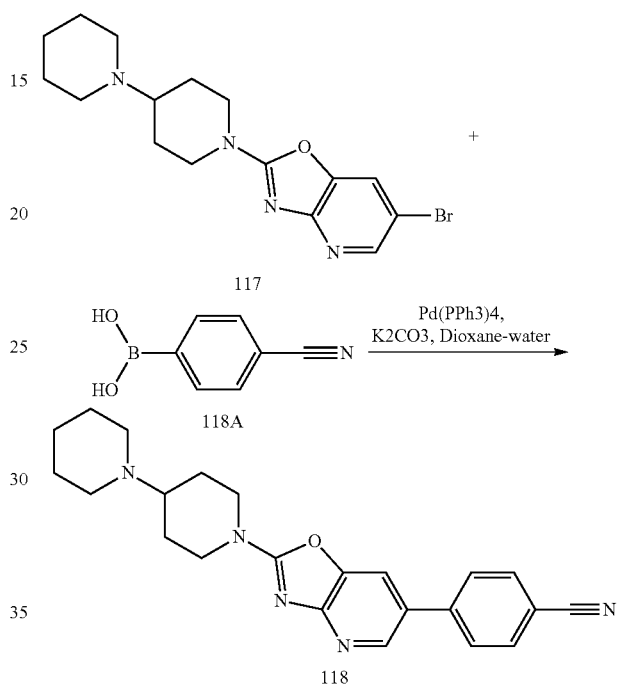

A mixture of Compound 117 (140 mg, 0.368 mmol), 118A (97 mg, 0.66 mmol), $Pd(PPh_3)_4$ (20 mg, 0.018 mmol), and $Na_2CO_3$ in Dioxane-water (4 ml/1 ml) was microwaved at 120° C. for 1 h. The reaction was cooled to room temperature and diluted with 1 N aq. NaOH solution. The mixture was extracted with EtOAc, dried over $Na_2SO_4$ and concentrated. The residue was purified by column chromatography and HPLC (Gilson) to give 118 (130 mg, 90%).

Example 119

Preparation of Compound 119

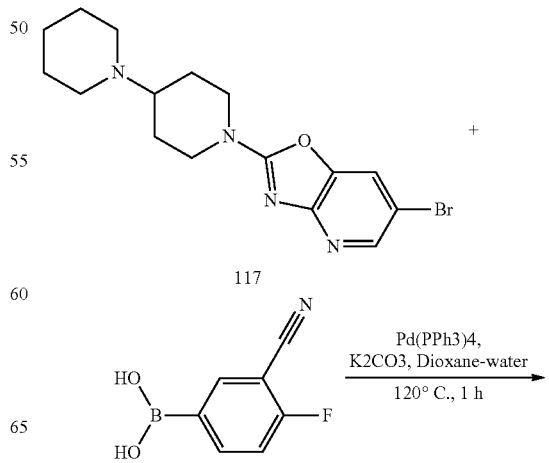

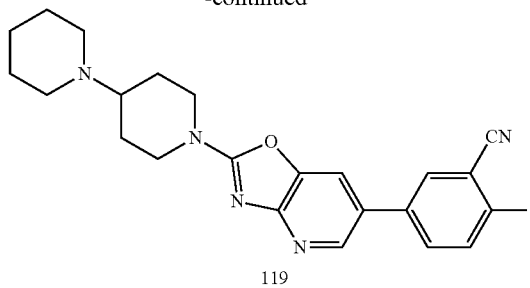

119

Compound 119 was prepared using the method described to make compound 118.

Example 120

Preparation of Compound 120

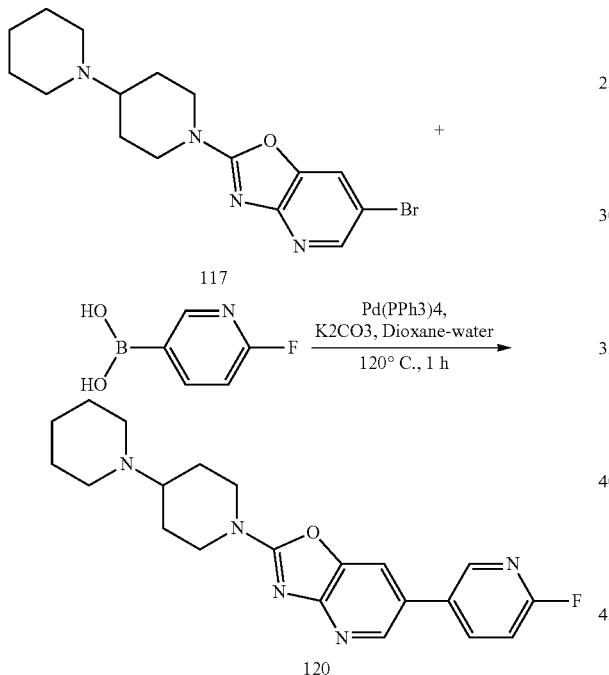

Compound 120 was prepared using the method described to make compound 118.

Example 121

Preparation of Compound 121

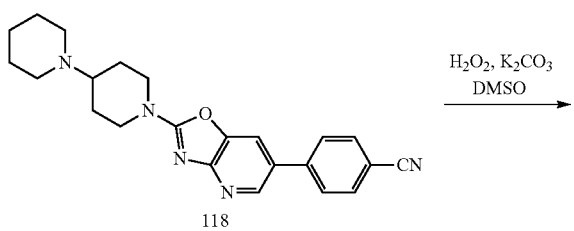

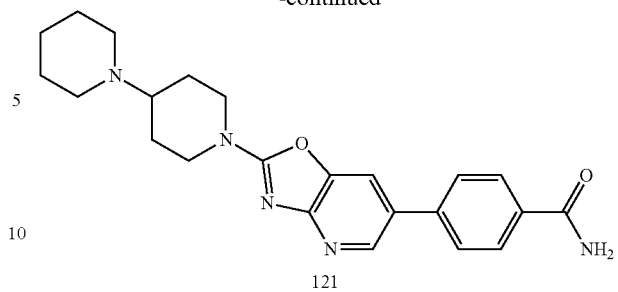

121

To a stirred solution of Compound 118 (50 mg, 0.13 mmol) in DMSO (1 ml) at 0° C. was added 30% $H_2O_2$ (0.2 ml) and then $K_2CO_3$ (100 mg). The reaction was brought to room temperature and stirred for 1 h before aq. NaOH solution was added. The mixture was extracted with EtOAc, dried over $Na_2SO_4$ and concentrated. The residue was purified by column chromatography and HPLC (Gilson) to give 121 (40 mg).

Example 122

Preparation of Compound 122

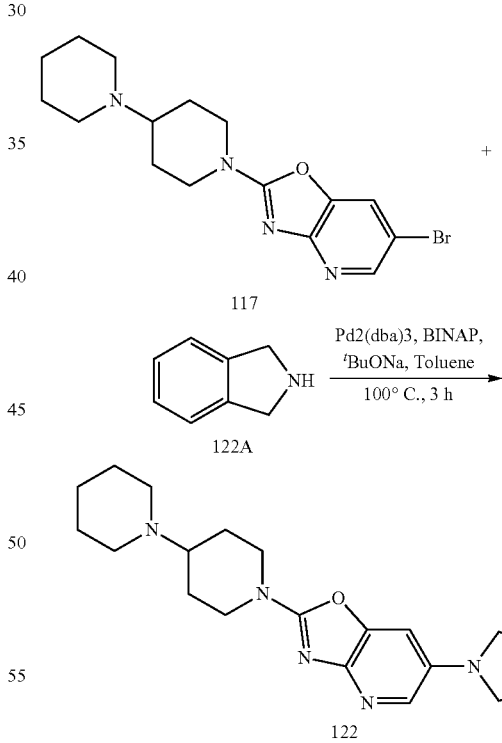

In a flask containing compound 117 (80 mg, 0.25 mmol) and 122A (64 mg, 0.32 mmol) was added anhydrous toluene (5 ml), followed by $^t$BuONa (36 mg, 0.375 mmol), $Pd_2(dba)_3$ (5 mg, 0.005 mmol) and BINAP (10 mg, 0.015 mmol). The mixture was evacuated and purged with $N_2$ and then heated to 100° C. under $N_2$ for 5 h. The reaction was cooled to room temperature, diluted with EtOAc, washed with 1N NaOH aq. solution and brine. The organic layer was dried and concentrated. The residue was purified by column chromatography and HPLC (Gilson) to give 122 (84 mg).
Example 123
Preparation of Compound 123
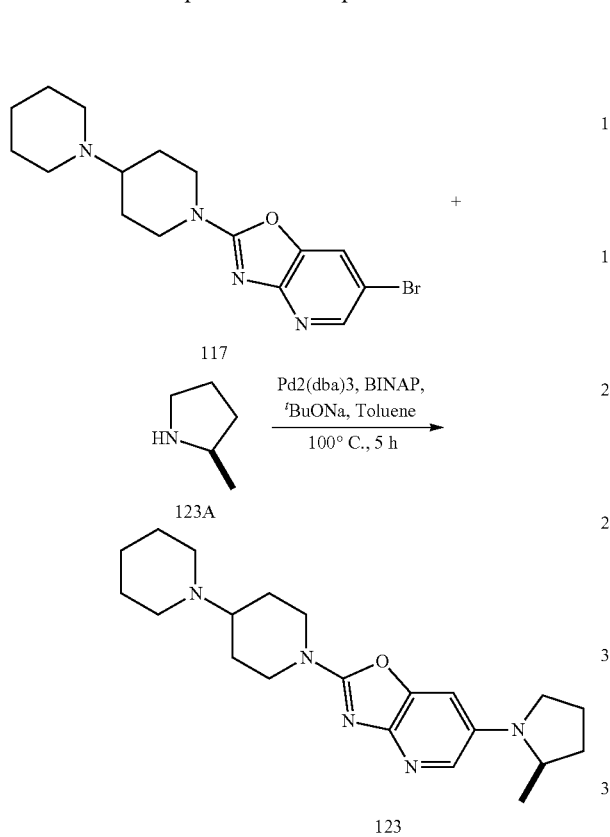
Compound 123 was prepared using the method described to make compound 122.
Example 124
Preparation of Compound 124
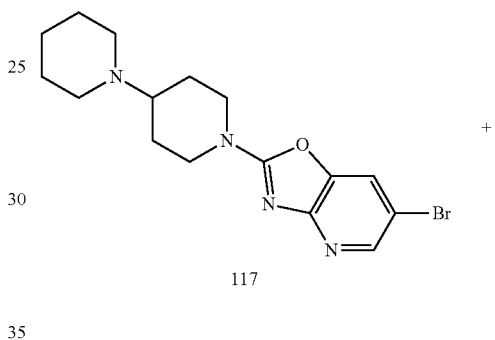
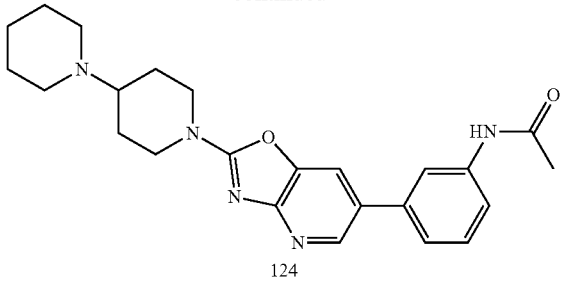
Compound 124 was prepared using the method described to make compound 118.
Example 125
Preparation of Compound 125
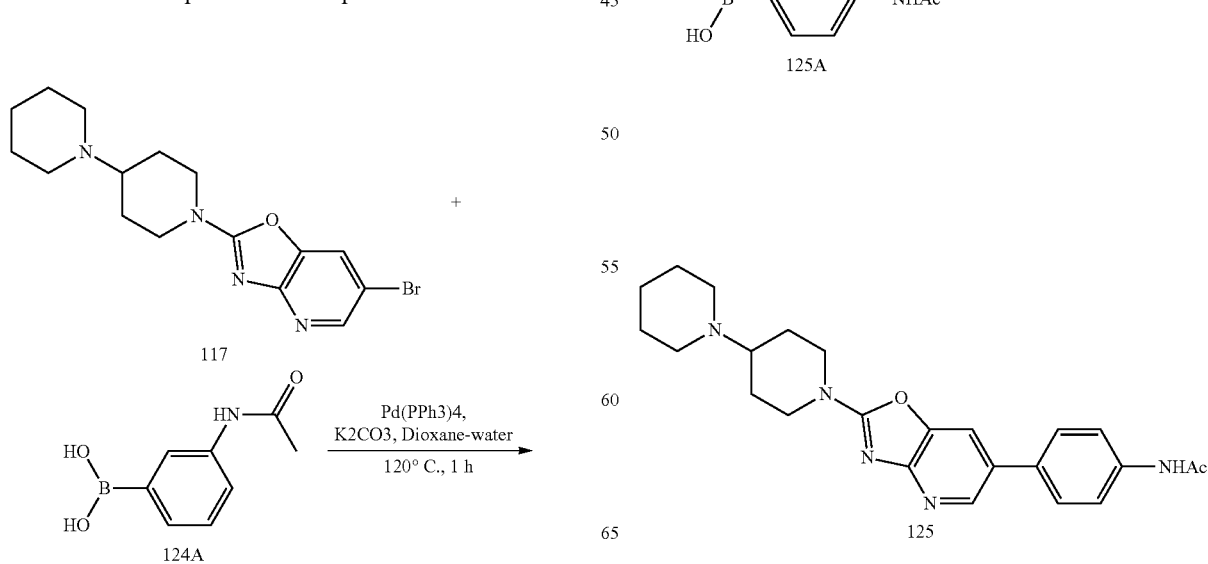

Compound 125 was prepared using the method described to make compound 118.
Example 126
Preparation of Compound 126
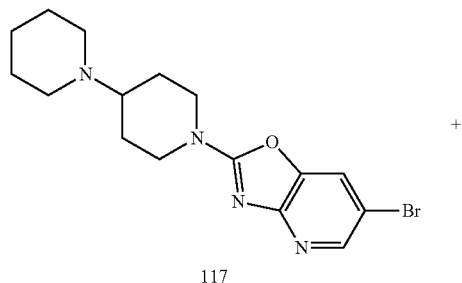
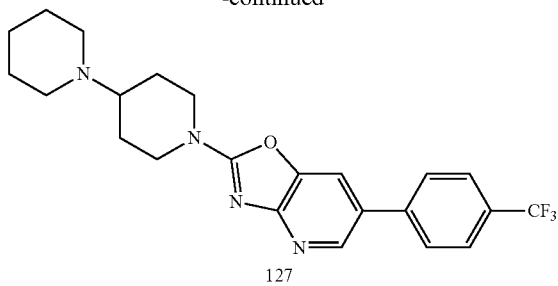
Compound 127 was prepared using the method described to make compound 118.
Example 128
Preparation of Compounds 128 & 130
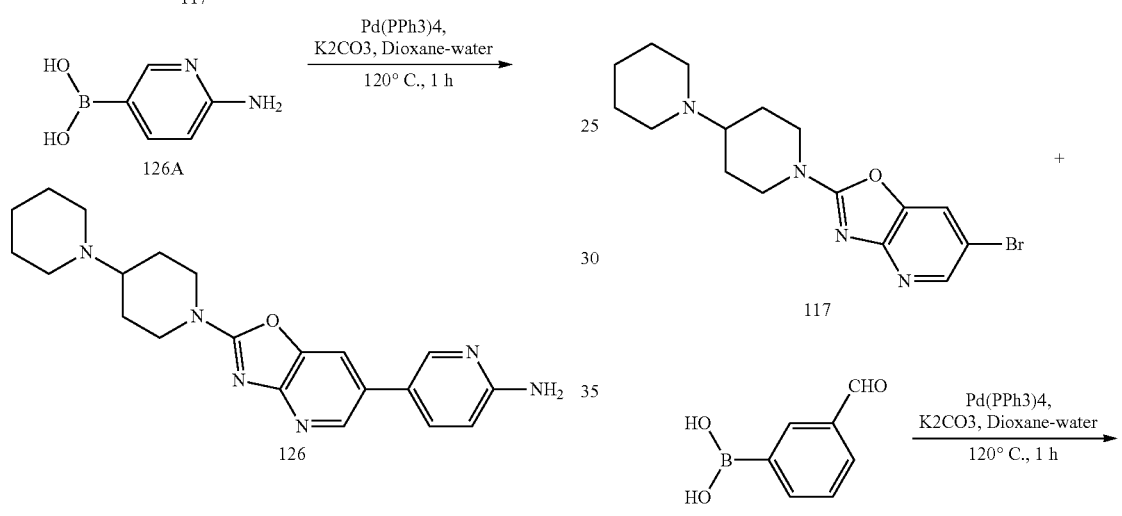
Compound 126 was prepared using the method described to make compound 118.
Example 127
Preparation of Compound 127
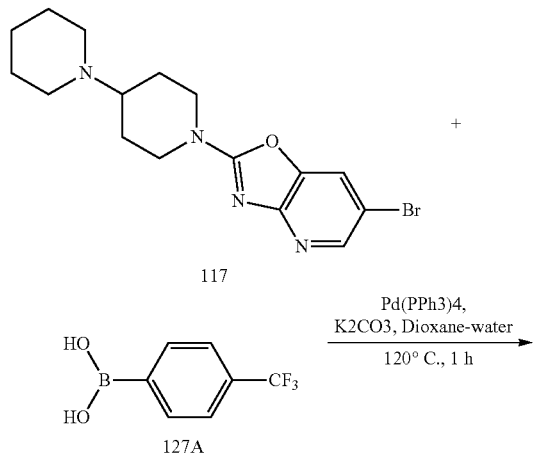
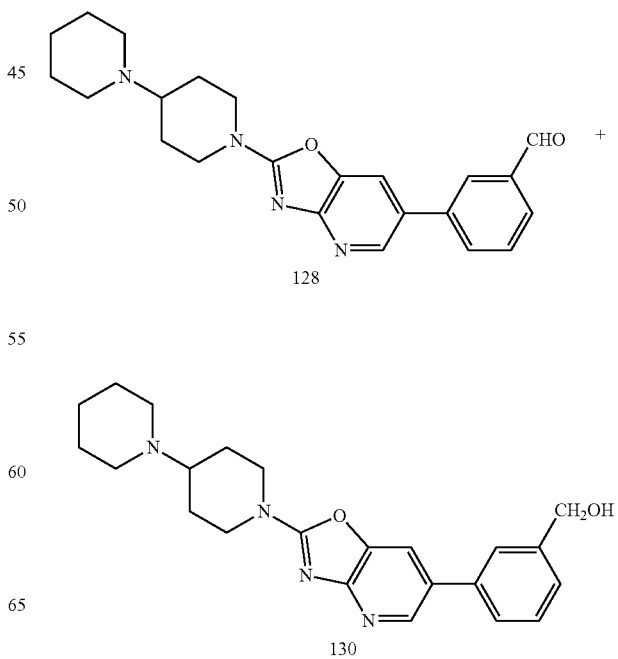

Compound 128 was prepared using the method described to make compound 118. Compound 130 was isolated as a side product.

Example 129

Preparation of Compound 129

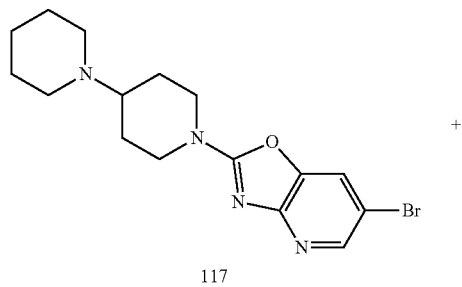

117

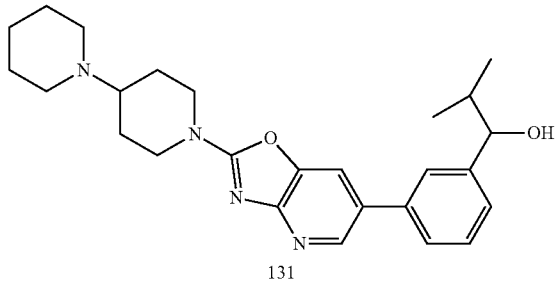

129A

129

Compound 129 was prepared using the method described to make compound 118.

Example 130

Preparation of Compound 131

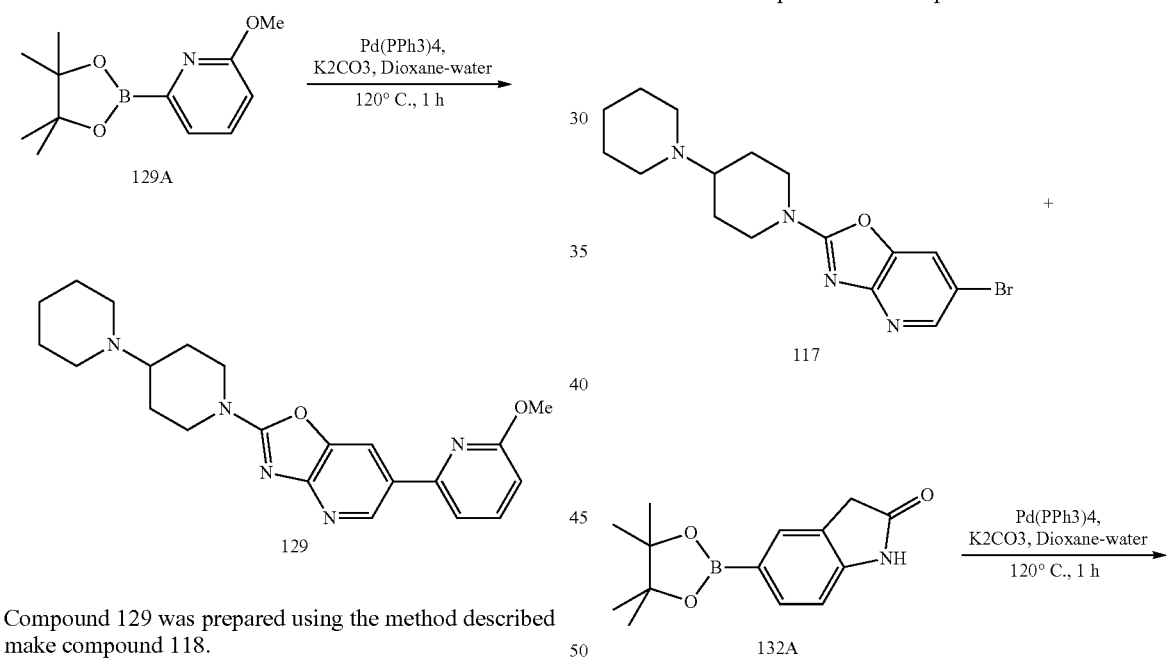

131

A solution of compound 128 (26 mg) in THF was added isopropyl magnesium chloride (1 ml, 2.0 M in THF) at −78° C. and the reaction was stirred from −78° C. to rt Overnight. Reaction was quenched by aq. KOH, extracted with EtOAc, dried and concentrated. The residue was purified by column chromatography and HPLC (Gilson) to give 131 (20 mg).

Example 131

Preparation of Compound 132

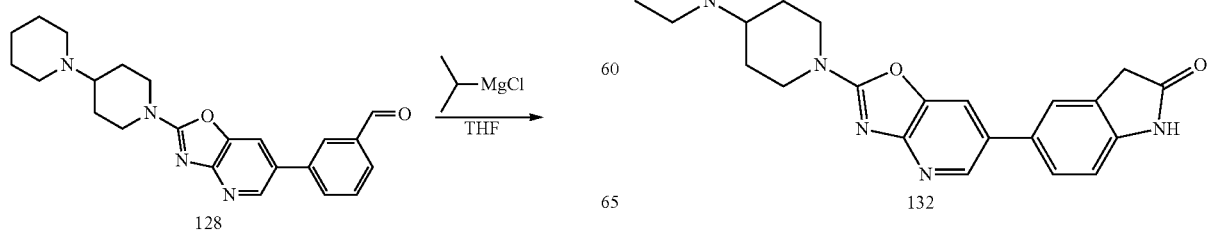

132

Compound 132 was prepared using the method described to make compound 118.

Example 132

Preparation of Compound 133

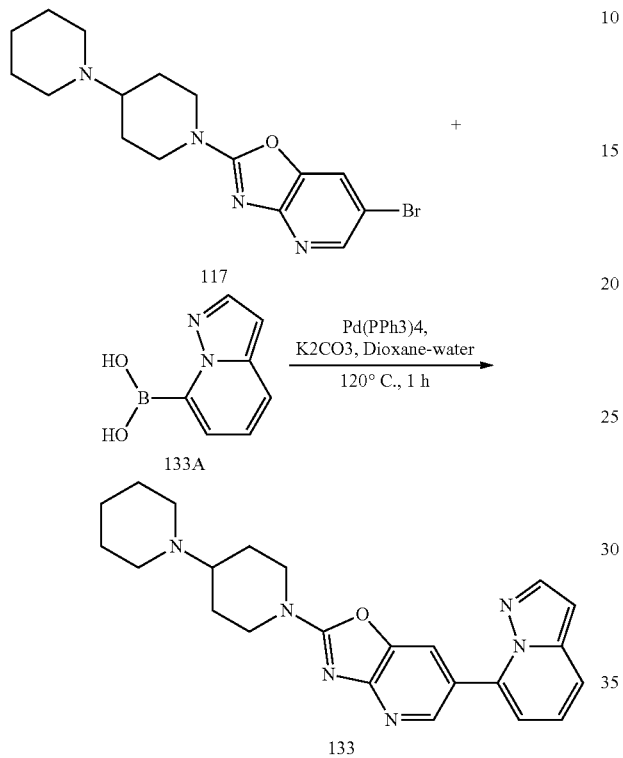

Compound 133 was prepared using the method described to make compound 118.

Example 133

Preparation of Compound 134

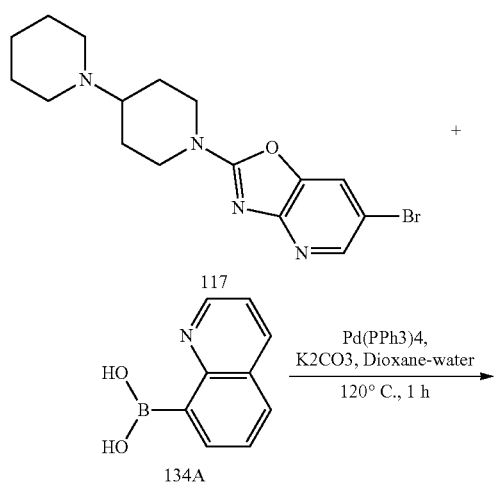

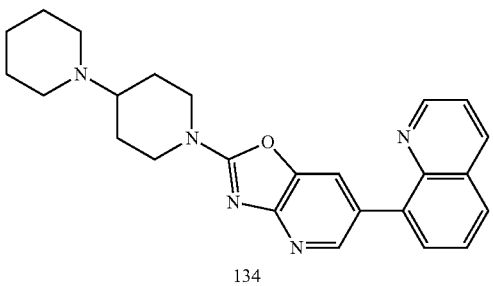

Compound 134 was prepared using the method described to make compound 118.

Example 134

Preparation of Compound 135

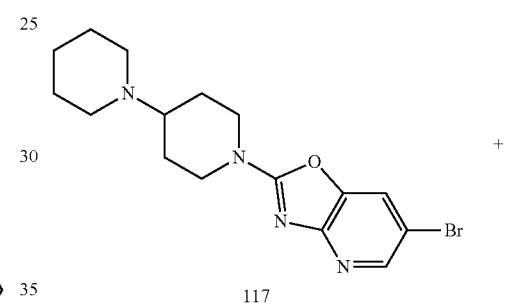

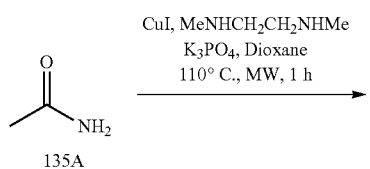

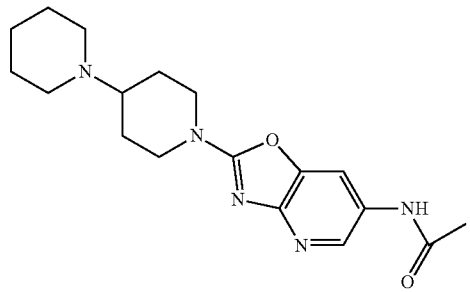

A mixture of compound 117 (50 mg, 0.13 mmol), 135A (23 mg, 0.39 mmol), CuI (5 mg, 0.026 mmol), K₃PO₄, (83 mg, 0.39 mmol) and dimethylethylenediamine (0.006 ml, 0.052 mmol) in dioxane (3 ml) was flushed with N₂, capped and microwaved at 110° C. for 1 h. Reaction was quenched by aq.

135

KOH, extracted with EtOAc, dried and concentrated. The residue was purified by column chromatography and HPLC (Gilson) to give 135 (20 mg).

Example 135

Preparation of Compound 136

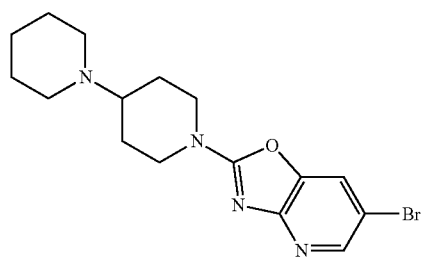

117

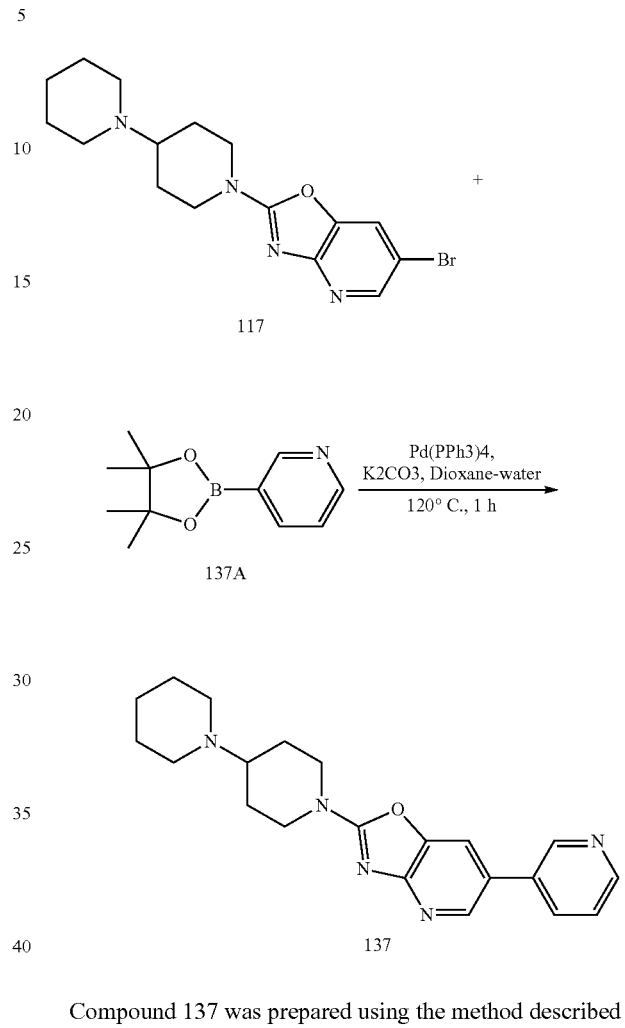

Compound 136 was prepared using the method described to make compound 118.

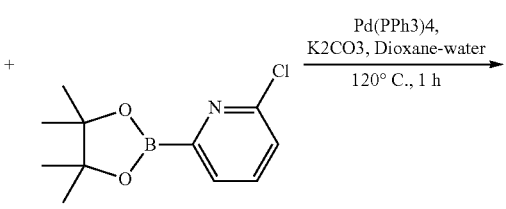

136

Example 136

Preparation of Compound 137

Compound 137 was prepared using the method described to make compound 118.

Example 137

Preparation of Compounds 138, 145 & 146

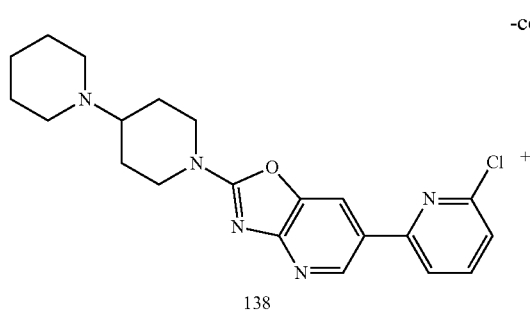
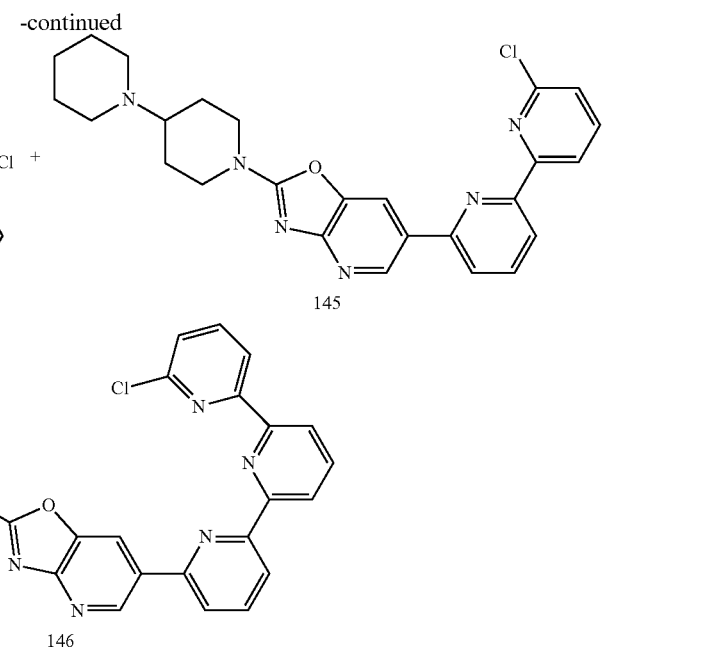
Compound 138 was prepared using the method described to make compound 118. Compound 145 and 146 were isolated as side products.
Example 138
Preparation of Compound 139
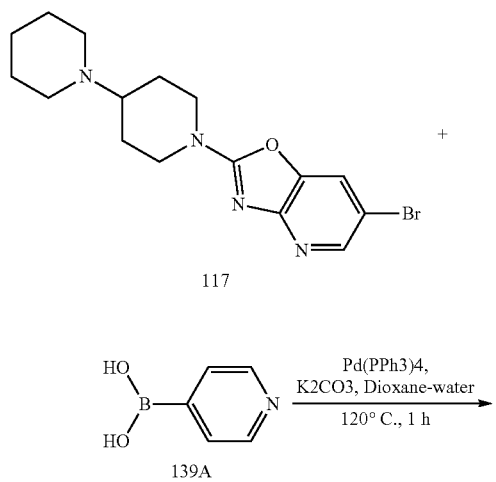
Compound 139 was prepared using the method described to make compound 118.
Example 139
Preparation of Compound 140
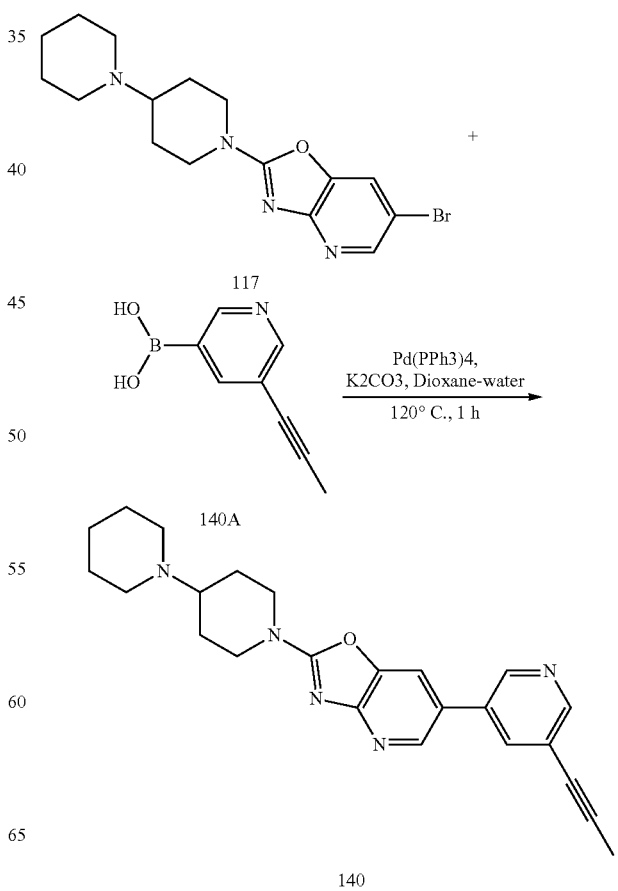

Compound 140 was prepared using the method described to make compound 118.

Example 140

Preparation of Compound 141

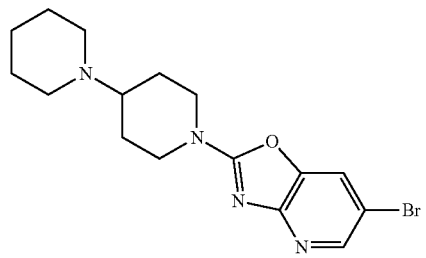

117

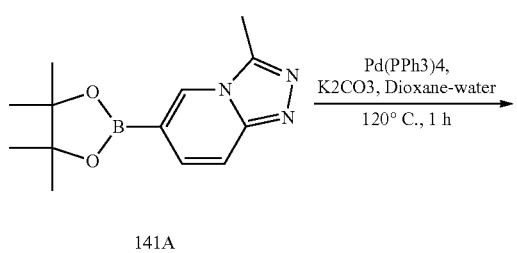

141A

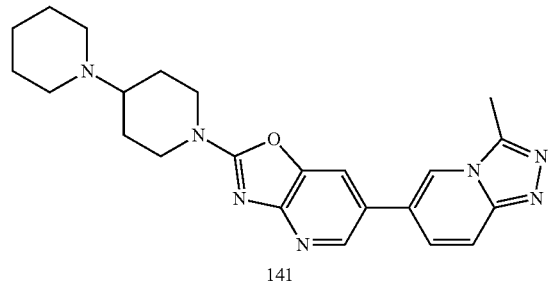

141

Compound 141 was prepared using the method described to make compound 118.

Example 141

Preparation of Compounds 142 & 143

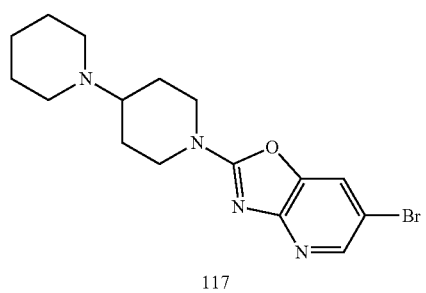

117

-continued

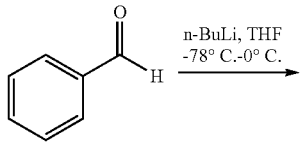

142A

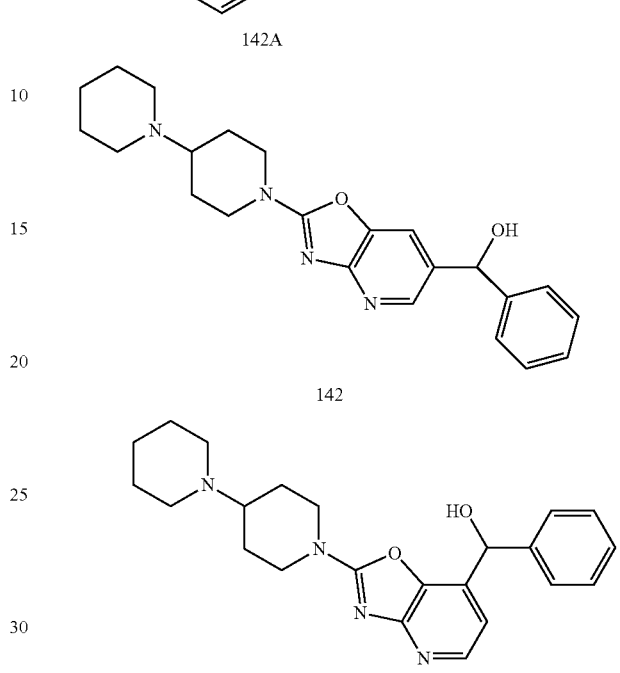

142

143

A solution of 117 (50 mg) in THF at −78° C. was added n-BuLi (0.4 ml, 2.5 M in hexane) and stirred for 1 h. The reaction was brought up to 0° C. in 4 h and quenched by water. It was extracted thoroughly with EtOAc, dried and concentrated. The residue was purified by column chromatography and HPLC (Gilson) to give 142 (5 mg) and 143 (4 mg).

Example 142

Preparation of Compound 144

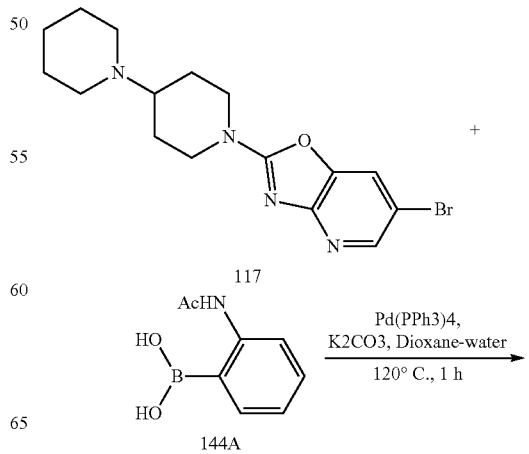

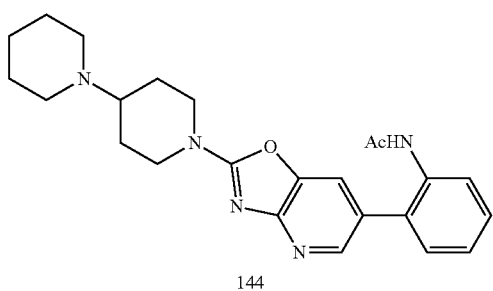

144

Compound 144 was prepared using the method described to make compound 118.

Example 143

Preparation of Compound 147

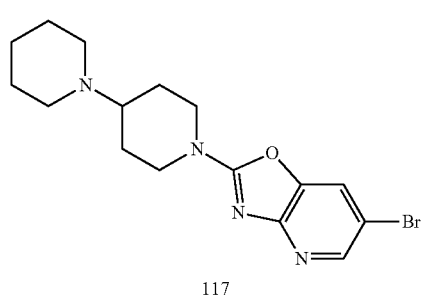

117

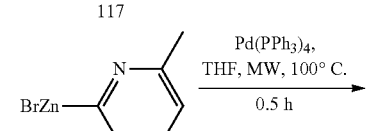

147A

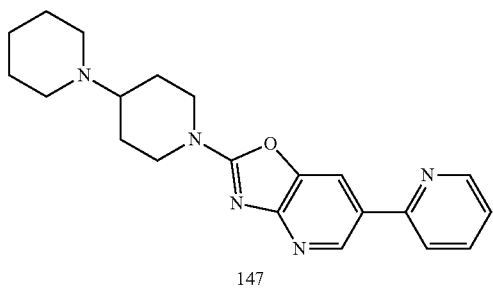

147

A mixture of compound 117 (80 mg, 0.22 mmol) and Pd(PPh₃)₄ (25 mg, 0.022 mmol) in THF was added compound 147A (1 ml, 0.5 M in THF). The mixture was microwaved at 100° C. for 0.5 h. The reaction was cooled to room temperature and diluted with 1 N aq. NaOH solution. The mixture was extracted with EtOAc, dried over Na₂SO₄ and concentrated. The residue was purified by column chromatography and HPLC (Gilson) to give 147 (79 mg).

Example 144

Preparation of Compound 148

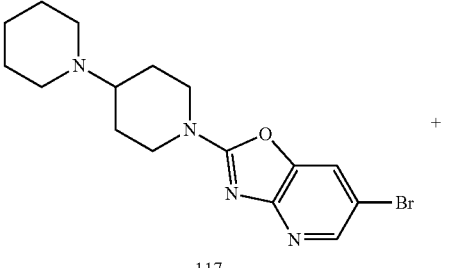

117

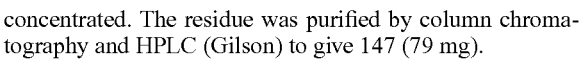

148A

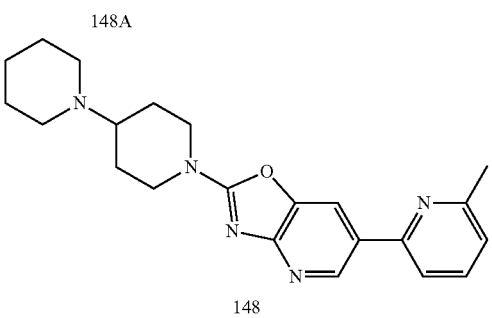

148

Compound 148 was prepared using the method described to make compound 147.

Example 145

Preparation of Compound 149

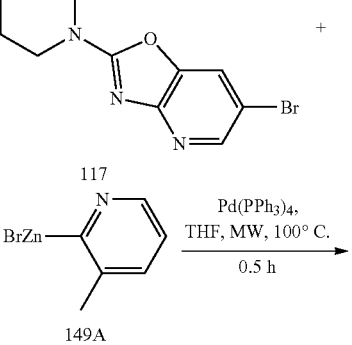

117

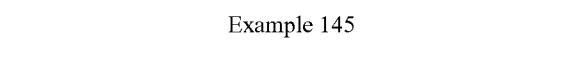

149A

-continued
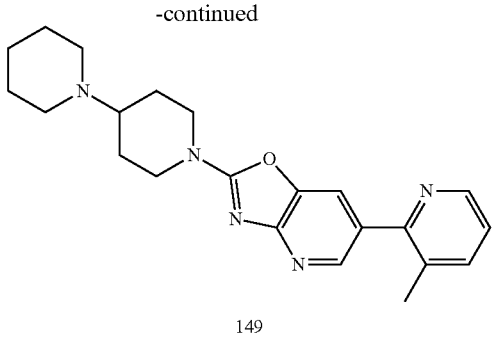
149
Compound 149 was prepared using the method described to make compound 147.
Example 146
Preparation of Compound 150
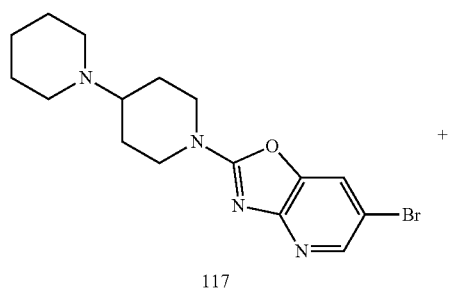
117
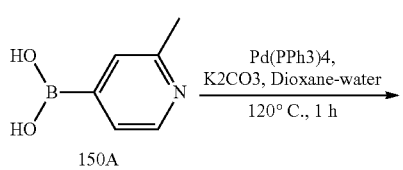
150A
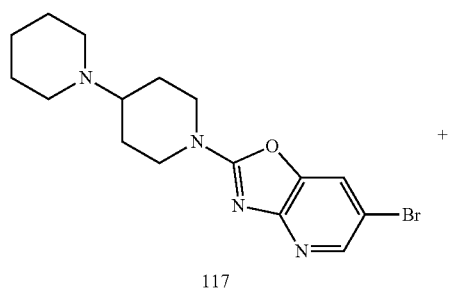
150
Compound 150 was prepared using the method described to make compound 118.
Example 147
Preparation of Compound 151
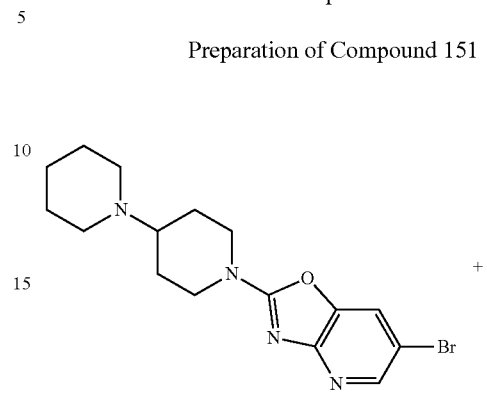
117
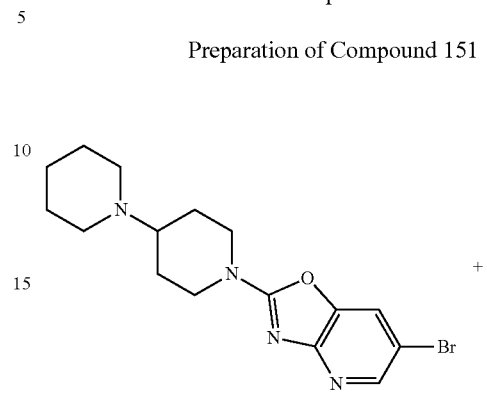
151
Compound 151 was prepared using the method described to make compound 118.
Example 148
Preparation of Compound 152
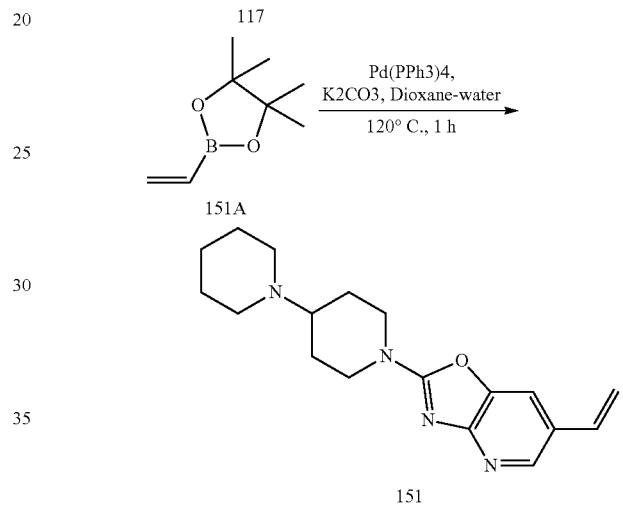

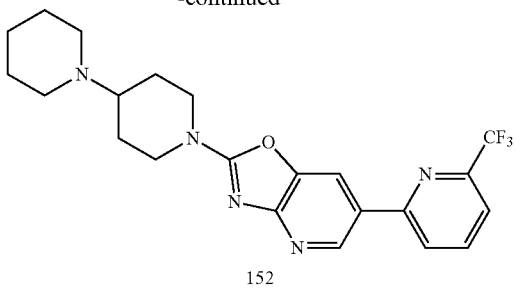

152

Compound 152 was prepared using the method described to make compound 118.

Example 149

Preparation of Compound 153

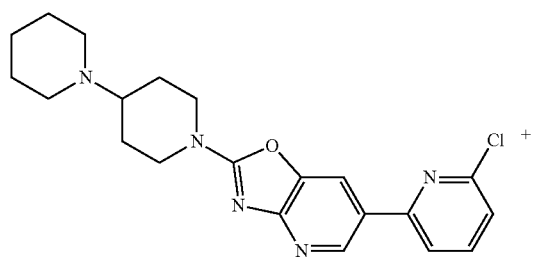

Compound 153 was prepared using the method described to make compound 118.

Example 150

Preparation of Compound 154

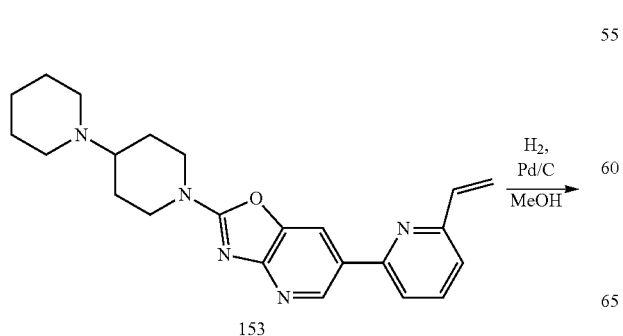

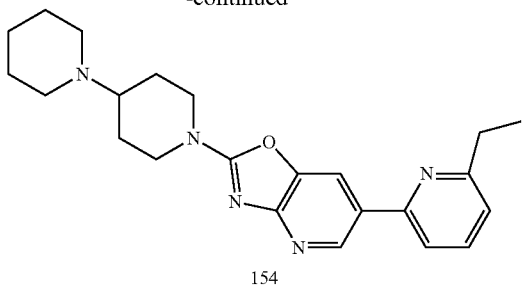

154

A solution of compound 153 (60 mg) in methanol (10 ml) was added Pd/C (30 mg) and the system was exchanged with $H_2$ twice. The reaction was stirred under $H_2$ for 2 h and the Mass showed the disappearance of the starting material. The reaction was filtered off and concentrated. The residue was purified by column chromatography and HPLC (Gilson) to give 154 (50 mg).

Example 151

Preparation of Compound 155

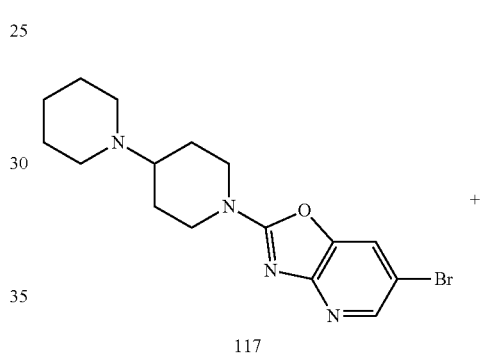

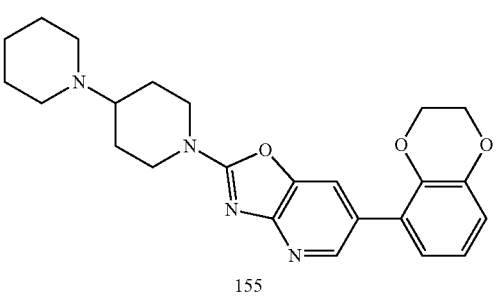

155

Compound 155 was prepared using the method described to make compound 118.

Example 152

Preparation of Compound 156

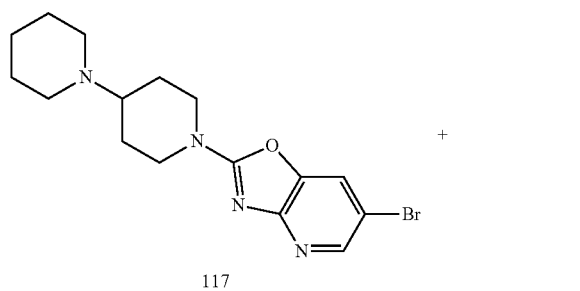

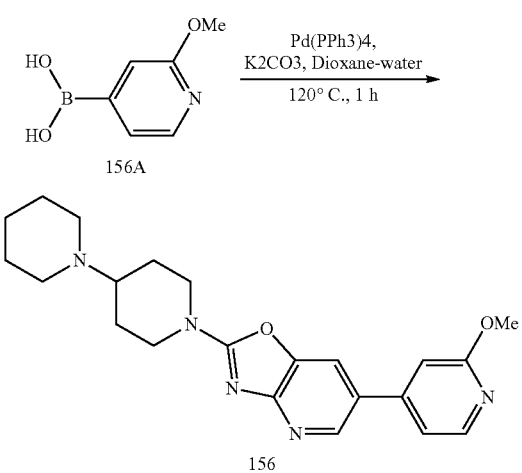

Compound 156 was prepared using the method described to make compound 118.

Example 153

Preparation of Compound 157

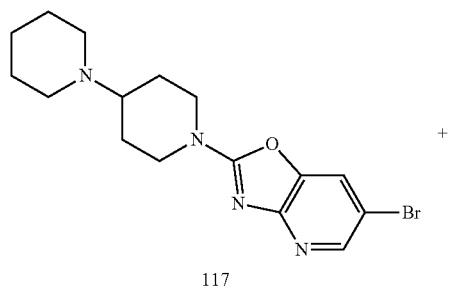

-continued

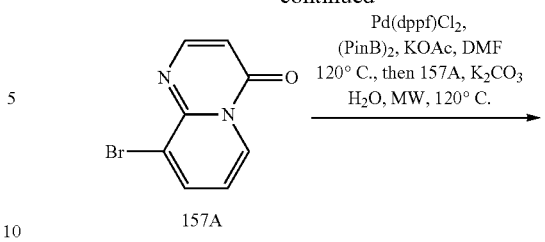

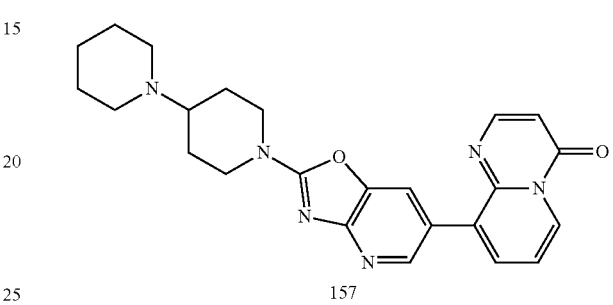

A mixture of Compound 117 (80 mg, 0.22 mmol), bis(pinacolato)diboron (61 mg, 0.242 mmol), and KOAc (65 mg, 0.66 mmol) in DMF (4 ml) was microwaved at 120° C. for 1 h. The reaction was cooled to room temperature. 157A (50 mg, 0.22 mmol), $K_2CO_3$ (65 mg), and water (1 ml) was added. The mixture was again microwaved at 120° C. for 1 h. The reaction was cooled to room temperature and diluted with 1 N aq. NaOH solution. The mixture was extracted with EtOAc, dried over $Na_2SO_4$ and concentrated. The residue was purified by column chromatography and HPLC (Gilson) to give 157 (55 mg).

Example 154

Preparation of Compound 158

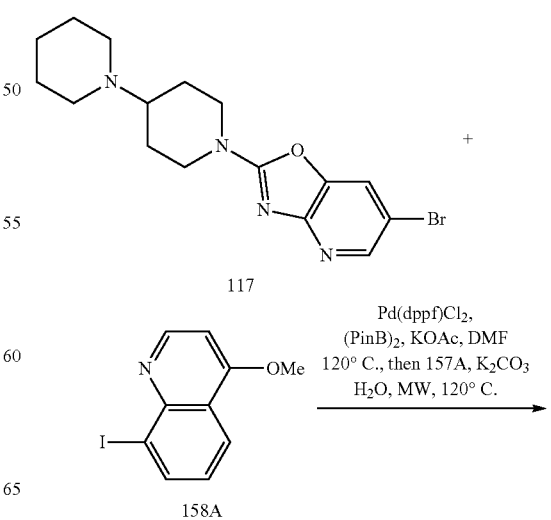

-continued
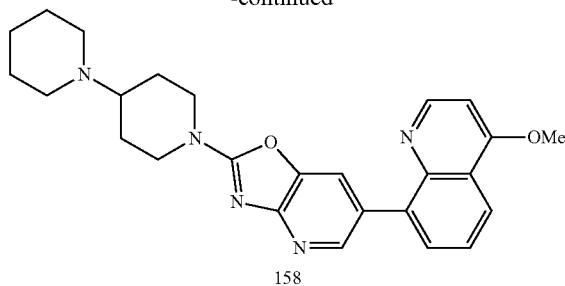
158
Compound 158 was prepared using the method described to make compound 157.
Example 155
Preparation of Compound 159
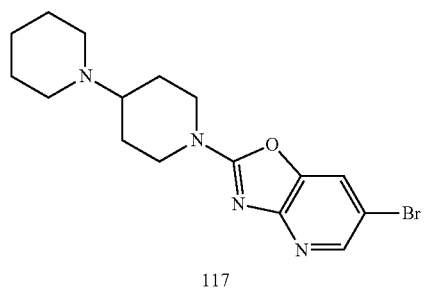
117
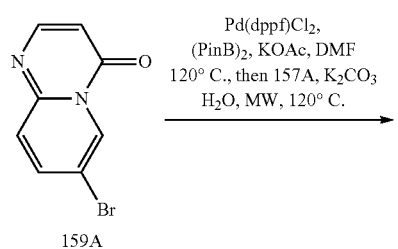
159A
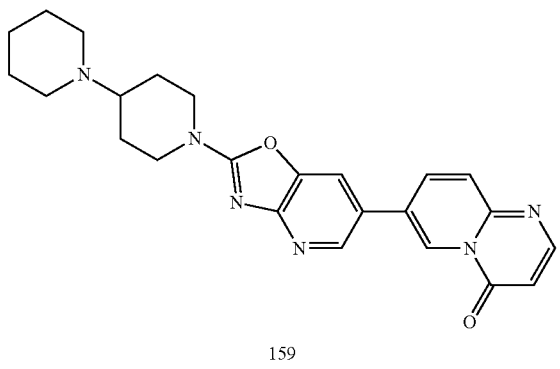
159
Compound 159 was prepared using the method described to make compound 157.
Example 156
Preparation of Compound 160
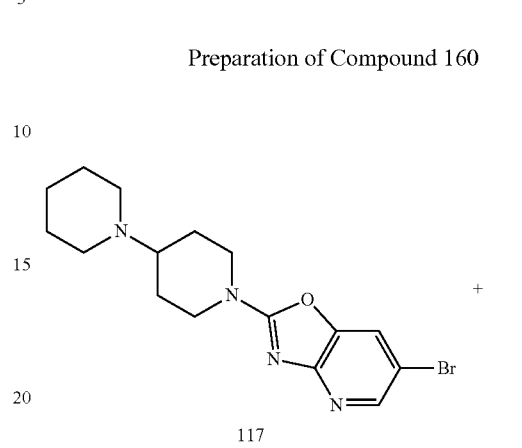
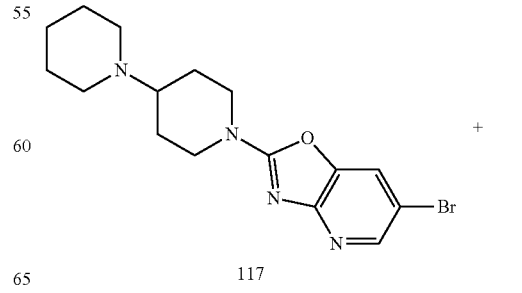
160
Compound 160 was prepared using the method described to make compound 157.
Example 157
Preparation of Compound 161
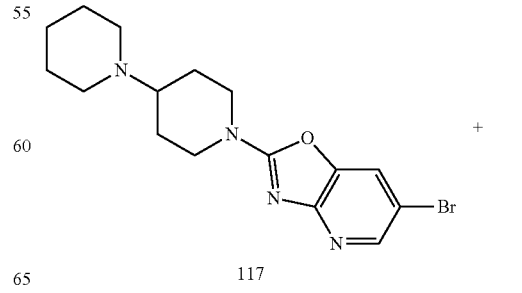
117

Example 158
Preparation of Compound 162
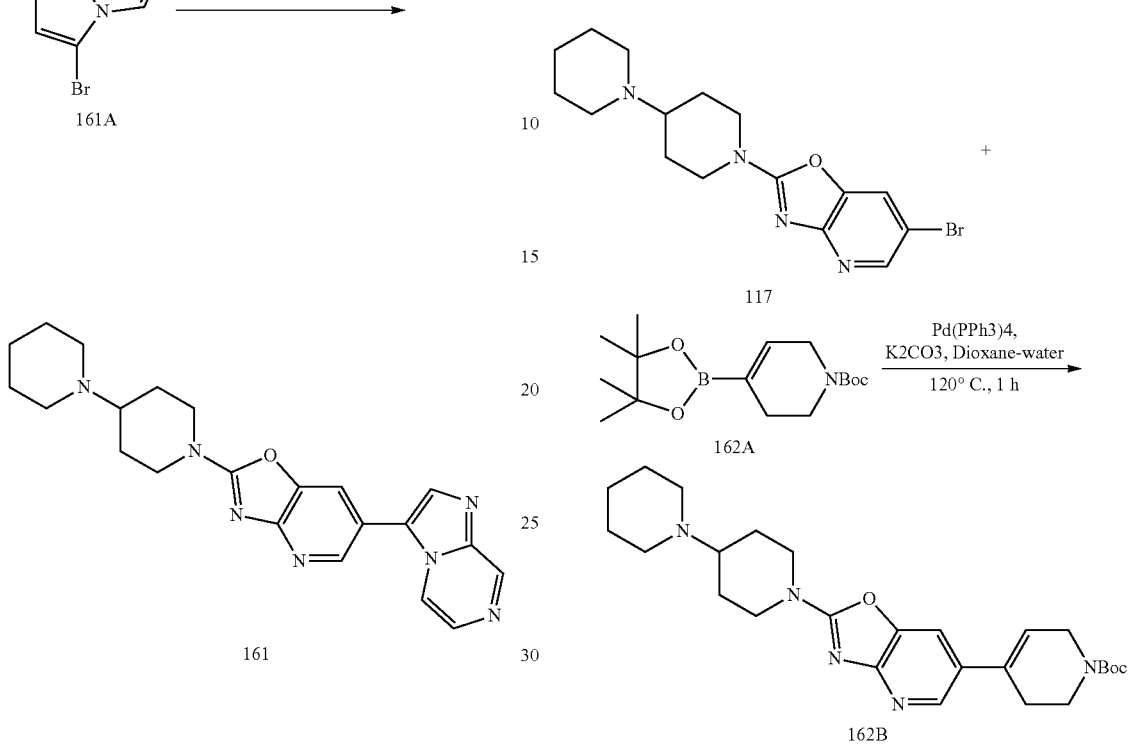
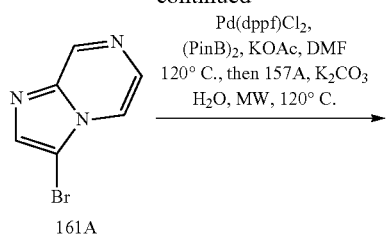
Compound 161 was prepared using the method described to make compound 157.
Compound 162B was prepared using the method described to make compound 118.
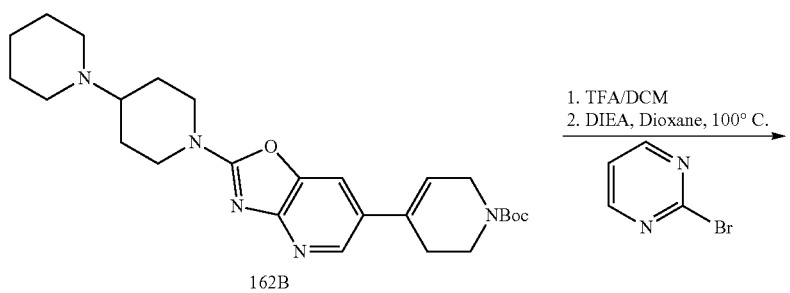
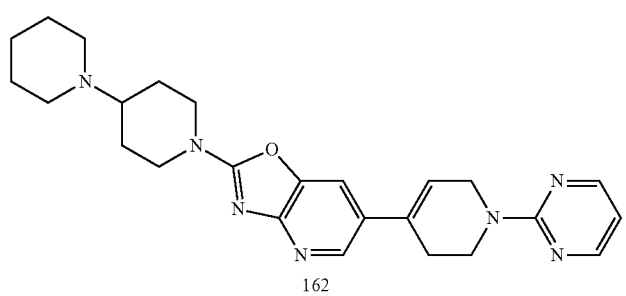

Compound 162B in DCM was treated with TFA at rt overnight. The reaction was concentrated and passing through a short column (Methanol/DCM, containing 2% NEt3). All the eluent was combined and concentrated to give the free amine which was used without further purification. The residue was dissolved in dioxane, to this solution was added DIEA and 2-bromopyrimidine. The mixture was heated at 100° C. for 5

A solution of compound 162B (160 mg) in methanol/DCM (6/3 ml) was added Pd/C (30 mg) and the system was exchanged with H₂ twice. The reaction was stirred under H₂ for 2 h and the Mass showed the disappearance of the starting material. The reaction was filtered off and concentrated. The residue was purified by column chromatography and HPLC (Gilson) to give 163A (150 mg).

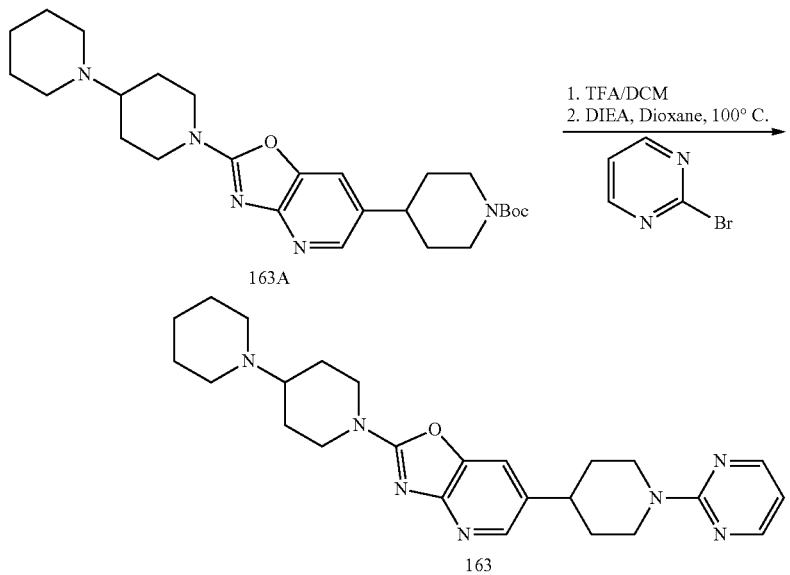

h. The reaction was cooled to room temperature and diluted with 1 N aq. NaOH solution. The mixture was extracted with EtOAc, dried over Na₂SO₄ and concentrated. The residue was purified by column chromatography and HPLC (Gilson) to give 162.

Compound 163 was prepared using the method described to make compound 162.

Example 159

Preparation of Compound 163

Example 160

Preparation of Compound 164

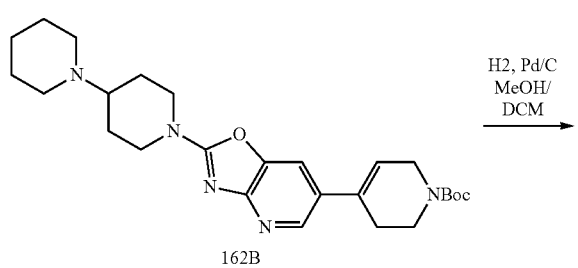

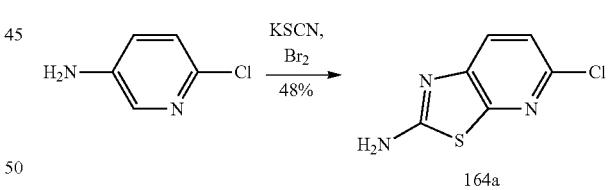

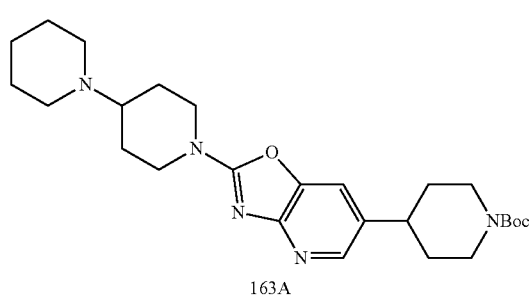

A mixture of 3-amino-6-chloropyridine (12.5 g, 98 mmol) and potassium thiocyanate (80 g, 820 mmol) in glacial acetic acid (200 mL) was cooled with ice bath. Bromine (0.6 mL, 11.6 mmol) was added dropwise. The resulting mixture was stirred at 0° C. for 1 h and room temperature overnight. Water (100 mL) was added to the mixture, and heated at 85° C. The mixture was filtered, while still warm. The solid was collected and washed with warm acetic acid. The combined filtrate was brought to basic by careful addition of ammonium hydroxide. DCM was added to the mixture. The aqueous layer was separated and extracted with DCM. The organic layer was combined, dried (MgSO₄), filtered and concentrated. The residue was purified with silica gel column to give 11.2 g (61%) of a white solid as the desired product 164a.

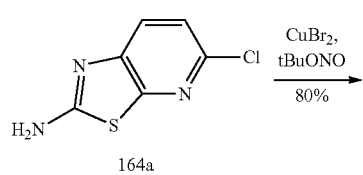

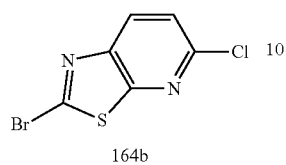

Copper (II) bromide (266 mg, 1.2 mmol) and tert-butylnitrile was mixed in CH₃CN (4 mL). Compound 164a (185 mg, 1.0 mmol) was added in three portions. The resulting mixture was stirred at room temperature for 2 h, until the reaction was complete by TLC. The mixture was loaded on a pad of silica gel, and eluted with EtOAc-hexanes (1:10). The filtrate was concentrated to give 132 mg (52%) white solid as the desired product 164b.

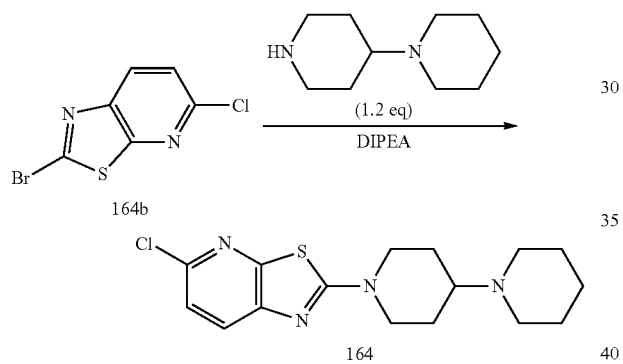

Starting material 164b (42 mg, 0.17 mmol) and DIPEA (0.12 mL) were dissolved in 0.8 mL PhCF₃-dioxane mixture (1:4, v/v). To the mixture, a solution of piperidinopiperidine (1M, 0.2 mL, 0.2 mmol) in PhCF₃-dioxane (1:4) was added. The mixture was heated at 160° C. in a microwave oven for 30 min. The mixture was concentrated and the residue was purified by preparative TLC, eluted with 1:10 7 N NH₃/MeOH-DCM, to give a white solid (40 mg, 70%) as desired product 164.

Example 161

Preparation of Compound 165

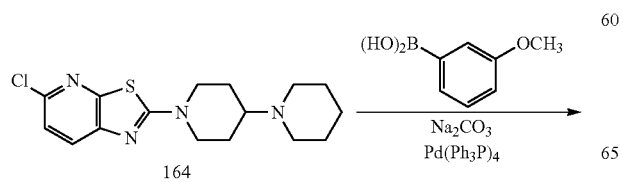

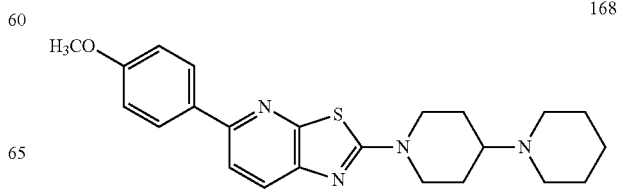

Compound 164 (100 mg, 0.30 mmol), 3-methoxyphenylboronic acid (82 mg, 0.54 mmol), Na₂CO₃ (95 mg, 0.90 mmol), and tetrakis(triphenylphosphine)palladium (34 mg, 0.03 mmol) were mixed in 3 mL of DME-H₂O (4:1). The mixture was heated in microwave oven at 160° C. for 40 min. The mixture was cooled to room temperature. EtOAc and water were added. The aqueous layer was separated and extracted with EtOAc. The organic extracts were combined, dried (MgSO₄), filtered and concentrated. The residue was purified with preparative TLC, eluted with 1:10 7 N NH₃/MeOH-DCM, to give a white solid (28 mg, 23%) as desired product 165.

Example 162

Preparation of Compounds 166

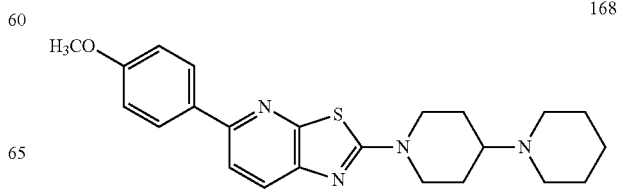

Compound 166 was prepared using the method described to make compound 165, with the respective boronic acid.

Example 163

Preparation of Compounds 167

Compound 167 was prepared using the method described to make compound 165, with the respective boronic acid.

Example 164

Preparation of Compounds 168

Compound 168 was prepared using the method described to make compound 165, with the respective boronic acid.

Example 165

Preparation of Compounds 169

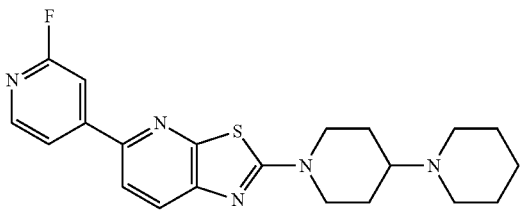

Compound 169 was prepared using the method described to make compound 165, with the respective boronic acid.

Example 166

Preparation of Compounds 170

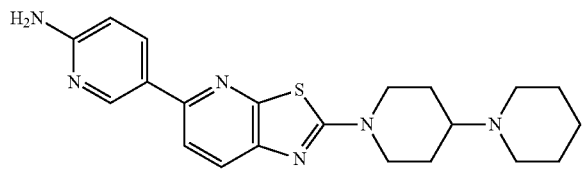

Compound 170 was prepared using the method described to make compound 165, with the respective boronic acid.

Example 167

Preparation of Compound 171

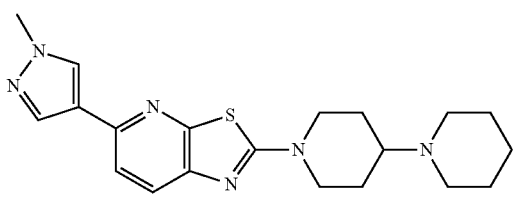

Compound 171 was prepared using the method described to make compound 165, with the respective boronic acid.

Example 168

$H_3$ Receptor Binding Assay

The source of the $H_3$ receptors in this experiment was guinea pig brain. The animals weighed 400-600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

Compounds of the invention to be tested were dissolved in DMSO and then diluted into the binding buffer (50 mM Tris, pH 7.5) such that the final concentration was 2 μg/ml with 0.1% DMSO. Membranes were then added (400 μg of protein) to the reaction tubes. The reaction was started by the addition of 3 nM [$^3$H]R-α-methyl histamine (8.8 Ci/mmol) or 3 nM [$^3$H]N$^\alpha$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Using this method, selected compounds of the present invention were tested and demonstrated Ki values ranging from about 1 nm to about 500 nM.

Example 169

In Vivo Effect of Compounds of the Invention on Glucose Levels in Diabetic Mice

Five-week-old male ICR mice were purchased from Taconic Farm (Germantown, N.Y.) and placed on a "western diet" containing 45% (kcal) fat from lard and 0.12% (w/w) cholesterol. After 3 weeks of feeding, the mice were injected once with low dose streptozocin (STZ, ip 75-100 mg/kg) to induce partial insulin deficiency. Two weeks after receiving the STZ injection, the majority of the STZ-treated mice developed type 2 diabetes and displayed hyperglycemia, insulin resistance, and glucose intolerance. The diabetic mice were then placed in one of three groups: (1) a non-treated control group, (2) a group treated with rosiglitazone (5 mg/kg/day in diet); or (3) a group treated with a compound of the present invention (30/mg/kg in diet) for four weeks.

Using this method, it was demonstrated that selected compounds of the present invention, when administered at 30/mg/kg in diet, significantly reduced non-fasting glucose and HbA1C levels relative to control mice and mice treated with rosiglitazone at 5 mg/kg/day in diet.

Example 170

Measuring the In Viva Effect of Compounds of the Invention on Glucose Levels in Diabetic Rats Adult, diabetic, Goto-Kakizaki rats (14 weeks old) can be used as a diabetic model for measuring the ability of the compounds of the present invention to lower elevated glucose levels. Glucose levels in test rats are first measured, then rats with glucose levels between 130 and 370 mg/dl are randomized into treatment (N=10) and control (N=10) groups. Animals in the treatment group are administered a compound of the present invention in their food chow at a dose of 10 mg/kg/day. After one week of treatment, blood is to be collected via tail snip and the non-fasting glucose level can then measured using a glucometer. The glucose levels of the treated animals is then compared to the glucose levels in non-treated control animals and the ability of the compounds of the invention to lower glucose levels, and thus treat diabetes, can be ascertained.

Uses of the Compounds of Formula (I)

The Compounds of Formula (I) are useful in human and veterinary medicine for treating or preventing a Condition in a patient. In accordance with the invention, the Compounds of Formula (I) can be administered to a patient in need of treatment or prevention of a Condition.

Accordingly, in one embodiment, the invention provides methods for treating a Condition in a patient comprising administering to the patient an effective amount of one or more compounds of Formula (I) or a pharmaceutically acceptable salt, solvate, ester or prodrug thereof. In addition, the present invention provides methods for treating or preventing Condition in a patient, comprising administering to the patient one or more Compounds of Formula (I) and an additional therapeutic agent that is not a Compound of Formula (I), wherein the amounts administered are together effective to treat or prevent the Condition.

In one embodiment, the compounds of the present invention can be ligands for the histamine $H_3$ receptor. In another embodiment, the compounds of the present invention can also be described as antagonists of the $H_3$ receptor, or as $H_3$ antagonists.

Treating or Preventing Allergy

The Compounds of Formula (I) are useful for treating or preventing allergy in a patient.

Accordingly, in one embodiment, the present invention provides a method for treating allergy in a patient, comprising administering to the patient an effective amount of one or more Compounds of Formula (I).

Non-limiting examples of allergy treatable or preventable using the present methods include Type I hypersensitivity reactions, Type II hypersensitivity reactions, Type III hypersensitivity reactions, Type IV hypersensitivity reactions, food allergies, allergic lung disorders, allergic reaction to a venomous sting or bite; mold allergies, environmental-related allergies (such allergic rhinitis, grass allergies and pollen allergies), anaphylaxis and latex allergy.

Treating or Preventing Allergy-Induced Airway Response

The Compounds of Formula (I) are useful for treating or preventing allergy-induced airway response in a patient.

Accordingly, in one embodiment, the present invention provides a method for treating allergy-induced airway response in a patient, comprising administering to the patient an effective amount of one or more Compounds of Formula (I).

Non-limiting examples of allergy-induced airway response treatable or preventable using the present methods include upper airway responses.

In one embodiment, the allergy-induced airway response is an upper airway response.

Treating or Preventing Congestion

The Compounds of Formula (I) are useful for treating or preventing congestion in a patient.

Accordingly, in one embodiment, the present invention provides a method for treating congestion in a patient, comprising administering to the patient an effective amount of one or more Compounds of Formula (I).

Non-limiting examples of congestion treatable or preventable using the present methods include nasal congestion and all types of rhinitis, including atrophic rhinitis, vasomotor rhinitis, gustatory rhinitis and drug induced rhinitis.

In one embodiment, the congestion is nasal congestion.

Treating or Preventing a Neurological Disorder

The Compounds of Formula (I) are useful for treating or preventing a neurological disorder in a patient. The term "neurological disorder," as used herein, refers to a disorder of any part of the central nervous system, including, but not limited to, the brain, nerves and spinal cord.

Accordingly, in one embodiment, the present invention provides a method for treating a neurological disorder in a patient, comprising administering to the patient an effective amount of one or more Compounds of Formula (I).

Non-limiting examples of neurological disorders treatable or preventable using the present methods include pain, hypotension, meningitis, a movement disorder (such as Parkinson's disease or Huntington's disease), delirium, dementia, Alzheimer's disease, a demyelinating disorder (such as multiple sclerosis or amyotrophic lateral sclerosis), aphasia, a peripheral nervous system disorder, a seizure disorder, a sleep disorder, a spinal cord disorder, stroke, attention deficit hyperactivity disorder (ADHD), hypo and hyperactivity of the central nervous system (such as agitation or depression) and schizophrenia.

In one embodiment, the neurological disorder is a sleep disorder.

In another embodiment, the neurological disorder is a movement disorder.

In another embodiment, the neurological disorder is Alzheimer's disease,

In yet another embodiment, the neurological disorder is schizophrenia.

In another embodiment, the neurological disorder is hypotension.

In still another embodiment, the neurological disorder is depression.

In a further embodiment, the neurological disorder is ADHD, which can be present in an adult or a child.

In one embodiment, the sleep disorder is a sleep disorder is hypersomnia, somnolence or narcolepsy.

In another embodiment, the movement disorder is Parkinson's disease or Huntington's disease.

In one embodiment, the neurological disorder is pain.

Non-limiting examples of pain treatable or preventable using the present methods include acute pain, chronic pain, neuropathic pain, nociceptive pain, cutaneous pain, somatic pain, visceral pain, phantom limb pain, cancer pain (including breakthrough pain), pain caused by drug therapy (such as cancer chemotherapy), headache (including migraine, tension headache, cluster headache, pain caused by arthritis, pain caused by injury, toothache, or pain caused by a medical procedure (such as surgery, physical therapy or radiation therapy).

In one embodiment, the pain is neuropathic pain.

In another embodiment, the pain is cancer pain.

In another embodiment, the pain is headache.

Treating or Preventing a Cardiovascular Disease

The Compounds of Formula (I) are useful for treating or preventing a cardiovascular disease in a patient.

Accordingly, in one embodiment, the present invention provides a method for treating a cardiovascular disease in a patient, comprising administering to the patient an effective amount of one or more Compounds of Formula (I).

Examples of cardiovascular diseases treatable or preventable using the present methods include, but are not limited to, an arrhythmia, an atrial fibrillation, a supraventricular tachycardia, arterial hypertension, arteriosclerosis, coronary artery disease, pulmonary artery disease, a cardiomyopathy, pericarditis, a peripheral artery disorder, a peripheral venous disorder, a peripheral lymphatic disorder, congestive heart failure, myocardial infarction, angina, a valvular disorder or stenosis.

In one embodiment, the cardiovascular disease is atherosclerosis.

In another embodiment, the cardiovascular disease is coronary artery disease.

Treating or Preventing a Gastrointestinal Disorder

The Compounds of Formula (I) are useful for treating or preventing a gastrointestinal disorder in a patient.

Accordingly, in one embodiment, the present invention provides a method for treating a gastrointestinal disorder in a patient, comprising administering to the patient an effective amount of one or more Compounds of Formula (I).

Examples of gastrointestinal disorders treatable or preventable using the present methods include, but are not limited to, hyper or hypo motility of the GI tract, acidic secretion of the GI tract, an anorectal disorder, diarrhea, irritable bowel syndrome, dyspepsia, gastroesophageal reflux disease (GERD), diverticulitis, gastritis, peptic ulcer disease, gastroenteritis, inflammatory bowel disease, a malabsorption syndrome or pancreatitis.

In one embodiment, the gastrointestinal disorder is GERD.

In another embodiment, the gastrointestinal disorder is hyper or hypo motility of the GI tract.

Treating or Preventing an Inflammatory Disease

The Compounds of Formula (I) are useful for treating or preventing an inflammatory disease in a patient.

Accordingly, in one embodiment, the present invention provides a method for treating an inflammatory disease in a patient, comprising administering to the patient an effective amount of one or more Compounds of Formula (I).

Treating or Preventing Non-Alcoholic Fatty Liver Disease

The Compounds of Formula (I) are useful for treating or preventing non-alcoholic fatty liver disease in a patient.

Accordingly, in one embodiment, the present invention provides a method for treating non-alcoholic fatty liver disease in a patient, comprising administering to the patient an effective amount of one or more Compounds of Formula (I).

Treating or Preventing a Metabolic Disorder

The Compounds of Formula (I) can be useful for treating a metabolic disorder. Accordingly, in one embodiment, the invention provides methods for treating a metabolic disorder in a patient, wherein the method comprises administering to the patient an effective amount of one or more Compounds of Formula (I), or a pharmaceutically acceptable salt, solvate, ester or prodrug thereof.

Examples of metabolic disorders treatable include, but are not limited to, metabolic syndrome (also known as "Syndrome X"), impaired glucose tolerance, impaired fasting glucose, dyslipidemia, hypercholesterolemia, hyperlipidemia, hypertriglyceridemia, low HDL levels, hypertension, phenylketonuria, post-prandial lipidemia, a glycogen-storage disease, Gaucher's Disease, Tay-Sachs Disease, Niemann-Pick Disease, ketosis and acidosis.

In one embodiment, the metabolic disorder is hypercholesterolemia.

In another embodiment, the metabolic disorder is hyperlipidemia.

In another embodiment, the metabolic disorder is hypertriglyceridemia.

In still another embodiment, the metabolic disorder is metabolic syndrome.

In a further embodiment, the metabolic disorder is low HDL levels.

In another embodiment, the metabolic disorder is dyslipidemia.

Treating or Preventing Obesity and Obesity-Related Disorders

The Compounds of Formula (I) can be useful for treating obesity or an obesity-related disorder. Accordingly, in one embodiment, the invention provides methods for treating obesity or an obesity-related disorder in a patient, wherein the method comprises administering to the patient an effective amount of one or more Compounds of Formula (I), or a pharmaceutically acceptable salt, solvate, ester or prodrug thereof.

Treating or Preventing Diabetes

The Compounds of Formula (I) are useful for treating or preventing diabetes in a patient. Accordingly, in one embodiment, the present invention provides a method for treating diabetes in a patient, comprising administering to the patient an effective amount of one or more Compounds of Formula (I).

Examples of diabetes treatable or preventable using the Compounds of Formula (I) include, but are not limited to, type I diabetes (insulin-dependent diabetes mellitus), type II diabetes (non-insulin dependent diabetes mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), type A insulin resistance syndrome, type B insulin resistance syndrome, lipatrophic diabetes, diabetes induced by β-cell toxins, and diabetes induced by drug therapy (such as diabetes induced by antipsychotic agents).

In one embodiment, the diabetes is type I diabetes.

In another embodiment, the diabetes is type II diabetes.

Treating or Preventing a Diabetic Complication

The Compounds of Formula (I) are useful for treating or preventing a diabetic complication in a patient. Accordingly, in one embodiment, the present invention provides a method for treating a diabetic complication in a patient, comprising administering to the patient an effective amount of one or more Compounds of Formula (I).

Examples of diabetic complications treatable or preventable using the Compounds of Formula (I) include, but are not limted to, diabetic cataract, glaucoma, retinopathy, aneuropathy (such as diabetic neuropathy, polyneuropathy, mononeuropathy, autonomic neuropathy, microaluminuria and progressive diabetic neuropathyl), nephropathy, gangrene of the feet, immune-complex vasculitis, systemic lupus erythematosus (SLE), atherosclerotic coronary arterial disease, peripheral arterial disease, nonketotic hyperglycemic-hyperosmolar coma, foot ulcers, joint problems, a skin or mucous membrane complication (such as an infection, a shin spot, a candidal infection or necrobiosis lipoidica diabeticorumobesity), hyperlipidemia, hypertension, syndrome of insulin resistance, coronary artery disease, a fungal infection, a bacterial infection, and cardiomyopathy.

In one embodiment, the diabetic complication is neuropathy.

In another embodiment, the diabetic complication is retinopathy.

In another embodiment, the diabetic complication is nephropathy.

Treating or Preventing Impaired Glucose Tolerance

The Compounds of Formula (I) are useful for treating or preventing impaired glucose tolerance in a patient.

Accordingly, in one embodiment, the present invention provides a method for treating impaired glucose tolerance in a patient, comprising administering to the patient an effective amount of one or more Compounds of Formula (I).

Treating or Preventing Impaired Fasting Glucose

The Compounds of Formula (I) are useful for treating or preventing impaired fasting glucose in a patient.

Accordingly, in one embodiment, the present invention provides a method for treating impaired fasting glucose in a patient, comprising administering to the patient an effective amount of one or more Compounds of Formula (I).

Combination Therapy

Accordingly, in one embodiment, the present invention provides methods for treating a Condition in a patient, the method comprising administering to the patient one or more Compounds of Formula (I), or a pharmaceutically acceptable salt or solvate thereof and at least one additional therapeutic agent that is not a Compound of Formula (I), wherein the amounts administered are together effective to treat or prevent a Condition.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Compounds of Formula (I) is administered during at time when the additional therapeutic agent(s) exert their prophylactic or therapeutic effect, or vice versa.

In another embodiment, the one or more Compounds of Formula (I) and the additional therapeutic agent(s) are administered in doses commonly employed when such agents are used as monotherapy for treating a Condition.

In another embodiment, the one or more Compounds of Formula (I) and the additional therapeutic agent(s) are administered in doses lower than the doses commonly employed when such agents are used as monotherapy for treating a Condition.

In still another embodiment, the one or more Compounds of Formula (I) and the additional therapeutic agent(s) act synergistically and are administered in doses lower than the doses commonly employed when such agents are used as monotherapy for treating a Condition.

In one embodiment, the one or more Compounds of Formula (I) and the additional therapeutic agent(s) are present in the same composition. In one embodiment, this composition is suitable for oral administration. In another embodiment, this composition is suitable for intravenous administration.

The one or more Compounds of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Compounds of Formula (I) and the additional therapeutic agent(s) may inhibit the resistance of a Condition to these agents.

In one embodiment, when the patient is treated for diabetes, a diabetic complication, impaired glucose tolerance or impaired fasting glucose, the other therapeutic is an antidiabetic agent which is not a Compound of Formula (I). In another embodiment, when the patient is treated for pain, the other therapeutic agent is an analgesic agent which is not a Compound of Formula (I).

In another embodiment, the other Therapeutic agent is an agent useful for reducing any potential side effect of a Compound of Formula (I). Such potential side effects include, but are not limited to, nausea, vomiting, headache, fever, lethargy, muscle aches, diarrhea, general pain, and pain at an injection site.

In one embodiment, the other therapeutic agent is used at its known therapeutically effective dose. In another embodiment, the other therapeutic agent is used at its normally prescribed dosage. In another embodiment, the other therapeutic agent is used at less than its normally prescribed dosage or its known therapeutically effective dose.

Examples of antidiabetic agents useful in the present methods for treating diabetes or a diabetic complication include a sulfonylurea; an insulin sensitizer (such as a PPAR agonist, a DPPIV inhibitor, a PTP-1B inhibitor and a glucokinase activator); an α-glucosidase inhibitor; an insulin secretagogue; a hepatic glucose output lowering agent; an anti-obesity agent; an antihypertensive agent; a meglitinide; an agent that slows or blocks the breakdown of starches and sugars in viva; a peptide that increases insulin production; and insulin or any insulin-containing composition.

In one embodiment, the antidiabetic agent is an insulin sensitizer or a sulfonylurea.

Non-limiting examples of sulfonylureas include glipizide, tolbutamide, glyburide, glimepiride, chlorpropamide, acetohexamide, gliamilide, gliclazide, glibenclamide and tolazamide.

Non-limiting examples of insulin sensitizers include PPAR activators, such as troglitazone, rosiglitazone, pioglitazone and englitazone; biguanidines such as metformin and phenformin; DPPIV inhibitors such as sitagliptin, saxagliptin, denagliptin and vildagliptin; PIP-1B inhibitors; and α-glucokinase activators, such as miglitol, acarbose, and voglibose.

Non-limiting examples of hepatic glucose output lowering agents include Glucophage and Glucophage XR.

Non-limiting examples of insulin secretagogues include sulfonylurea and non-sulfonylurea drugs such as GLP-1, exendin, GIP, secretin, glipizide, chlorpropamide, nateglinide, meglitinide, glibenclamide, repaglinide and glimepiride.

The term "insulin" as used herein, includes all formulations of insulin, including long acting and short acting forms of insulin.

In one embodiment, the antidiabetic agent is anti-obesity agent.

Non-limiting examples of anti-obesity agents useful in the present methods for treating diabetes include a 5-HT2C agonist, such as lorcaserin; a neuropeptide Y antagonist; an MCR4 agonist; an MCH receptor antagonist; a protein hormone, such as leptin or adiponectin; an AMP kinase activator; and a lipase inhibitor, such as orlistat. Appetite suppressants are not considered to be within the scope of the anti-obesity agents useful in the present methods.

Non-limiting examples of antihypertensive agents useful in the present methods for treating diabetes include β-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

Non-limiting examples of meglitinides useful in the present methods for treating diabetes include repaglinide and nateglinide.

Non-limiting examples of insulin sensitizing agents include biguanides, such as metformin, metformin hydrochloride (such as GLUCOPHAGE® from Bristol-Myers Squibb), metformin hydrochloride with glyburide (such as GLUCOVANCE™ from Bristol-Myers Squibb) and buformin; glitazones; and thiazolidinediones, such as rosiglitazone, rosiglitazone maleate (AVANDIA™ from GlaxoSmithKline), pioglitazone, pioglitazone hydrochloride (ACTOS™, from Takeda) ciglitazone and MCC-555 (Mitstubishi Chemical Co.)

In one embodiment, the insulin sensitizer is a thiazolidinedione.

In one embodiment, the insulin sensitizer is a biguanide.

Non-limiting examples of antidiabetic agents that slow or block the breakdown of starches and sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of orally administrable insulin and insulin containing compositions include AL-401 from Autoimmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

Non-limiting examples of other analgesic agents useful in the present methods for treating pain include acetaminophen, an NSAID, an opiate or a tricyclic antidepressant.

In one embodiment, the other analgesic agent is acetaminophen or an NSAID.

In another embodiment, the other analgesic agent is an opiate.

In another embodiment, the other analgesic agent is a tricyclic antidepressant.

Non-limiting examples of NSAIDS useful in the present methods for treating pain include a salicylate, such as aspirin, amoxiprin, benorilate or diflunisal; an arylalkanoic acid, such as diclofenac, etodolac, indometacin, ketorolac, nabumetone, sulindac or tolmetin; a 2-arylpropionic acid (a "profen"), such as ibuprofen, carprofen, fenoprofen, flurbiprofen, loxoprofen, naproxen, tiaprofenic acid or suprofen; a fenamic acid, such as mefenamic acid or meclofenamic acid; a pyrazolidine derivative, such as phenylbutazone, azapropazone, metamizoie or oxyphenbutazone; a coxib, such as celecoxib, etoricoxib, lumiracoxib or parecoxib; an oxicam, such as piroxicam, lornoxicam, meloxicam or tenoxicam; or a sulfonanilide, such as nimesulide.

Non-limiting examples of opiates useful in the present methods for treating pain include an anilidopiperidine, a phenylpiperidine, a diphenylpropylamine derivative, a benzomorphane derivative, an oripavine derivative and a morphinane derivative. Additional illustrative examples of opiates include morphine, diamorphine, heroin, buprenorphine, dipipanone, pethidine, dextromoramide, alfentanil, fentanyl, remifentanil, methadone, codeine, dihydrocodeine, tramadol, pentazocine, vicodin, oxycodone, hydrocodone, percocet, percodan, norco, dilaudid, darvocet or lorcet.

Non-limiting examples of tricyclic antidepressants useful in the present methods for treating pain include amitryptyline, carbamazepine, gabapentin or pregabalin.

The Compounds of Formula (I) can be combined with an $H_1$ receptor antagonist (i.e., the Compounds of Formula (I) can be combined with an $H_1$ receptor antagonist in a pharmaceutical composition, or the Compounds of Formula (I) can be administered with one or more $H_1$ receptor antagonists).

Numerous chemical substances are known to have histamine $H_1$ receptor antagonist activity and can therefore be used in the methods of this invention. Many $H_1$ receptor antagonists useful in the methods of this invention can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, International Publication No. WO98/06394.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

More preferably, said $H_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Most preferably, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole.

Even more preferably, said $H_1$ antagonist is selected from loratadine, descarboethoxyloratadine, fexofenadine or cetirizine. Still even more preferably, said $H_1$ antagonist is loratadine or descarboethoxyloratadine.

In one preferred embodiment, said $H_1$ receptor antagonist is loratadine.

In another preferred embodiment, said $H_1$ receptor antagonist is descarboethoxyloratadine.

In still another preferred embodiment, said $H_1$ receptor antagonist is fexofenadine.

In yet another preferred embodiment, said $H_1$ receptor antagonist is cetirizine.

Preferably, in the above methods, allergy-induced airway responses are treated.

Also, preferably, in the above methods, allergy is treated.

Also, preferably, in the above methods, nasal congestion is treated.

In the methods of this invention wherein a combination of an $H_3$ antagonist of this invention (compound of formula I) is administered with a $H_1$ antagonist, the antagonists can be administered simultaneously or sequentially (first one and then the other over a period of time). In general, when the antagonists are administered sequentially, the $H_3$ antagonist of this invention (compound of formula I) is administered first.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Compound(s) of Formula (I) and the other agent(s) for treating diseases or conditions listed above can be administered simultaneously or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Compounds of Formula (I) and the additional therapeutic agent(s) can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

Compositions and Administration

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions, As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the Compound of Formula (I) is administered orally.

In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen far oral administration can range from about 1 mg/day to about 300 mg/day, preferably 1 mg/day to 75 mg/day, in two to four divided doses.

When the invention comprises a combination of one or more compounds of Formula (I) and an additional therapeutic agent, the two active components may be co-administered simultaneously or sequentially, or a single pharmaceutical composition comprising one or more compounds of Formula (I) and an additional therapeutic agent in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages because of the advantageous effect of the combination.

In one embodiment, when the components of a combination therapy regime are to be administered simultaneously, they can be administered in a single composition with a pharmaceutically acceptable carrier.

In another embodiment, when the components of a combination therapy regime are to be administered separately or sequentially, they can be administered in separate compositions, each containing a pharmaceutically acceptable carrier.

The components of the combination therapy can be administered individually or together in any conventional dosage form such as capsule, tablet, powder, cachet, suspension, solution, suppository, nasal spray, etc.

Kits

In one aspect, the present invention provides a kit comprising a effective amount of one or more Compounds of Formula (I), or a pharmaceutically acceptable salt or solvate of the compound and a pharmaceutically acceptable carrier, vehicle or diluent.

In another aspect the present invention provides a kit comprising an amount of one or more Compounds of Formula (I), or a pharmaceutically acceptable salt or solvate of the compound and an amount of at least one additional therapeutic agent listed above, wherein the combined amounts are effective for treating or preventing diabetes, a diabetic complication impaired glucose tolerance or impaired fasting glucose in a patient.

When the components of a combination therapy regime are to are to be administered in more than one composition, they can be provided in a kit comprising in a single package, one container comprising a Compound of Formula (I) in pharmaceutically acceptable carrier, and a separate container comprising an additional therapeutic agent in a pharmaceutically acceptable carrier, with the active components of each composition being present in amounts such that the combination is therapeutically effective.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound which is selected from the group consisting of:

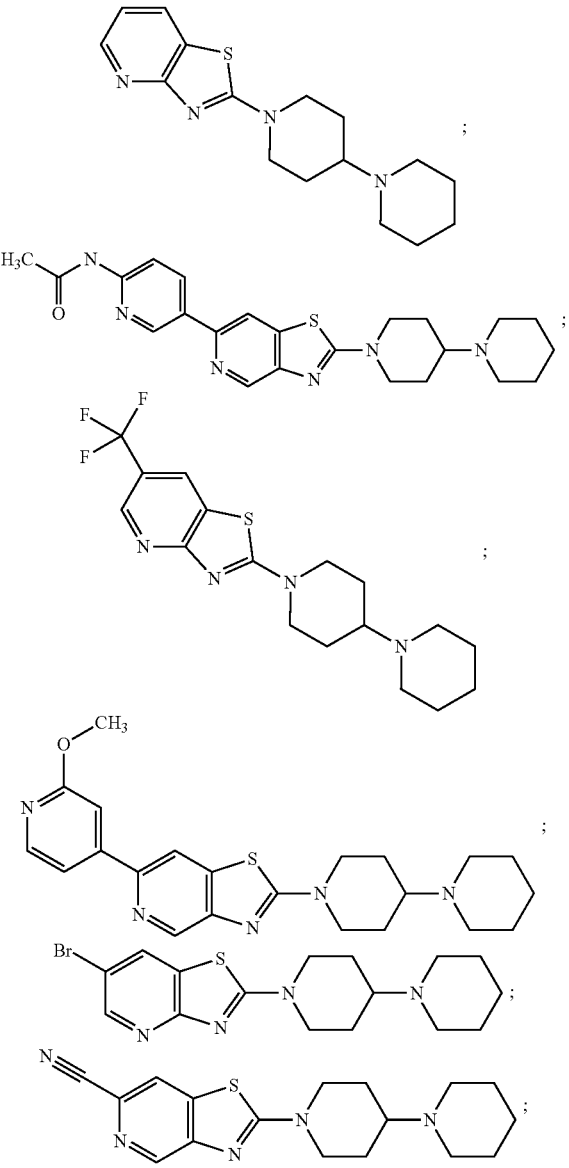

-continued

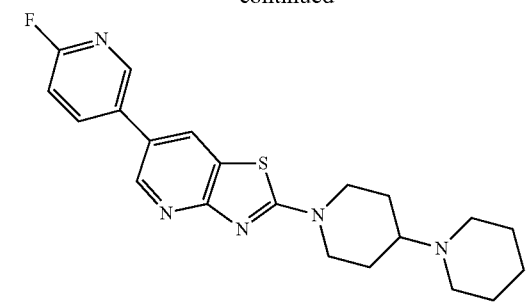
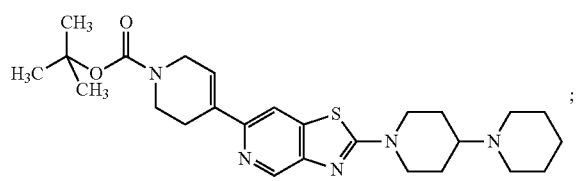
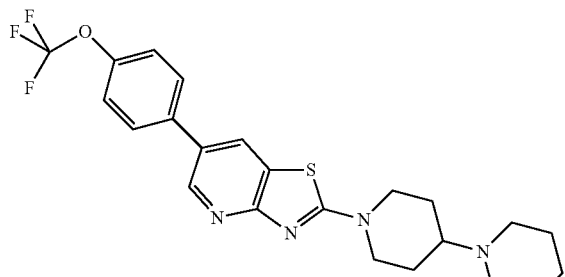
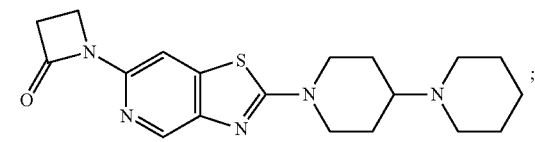
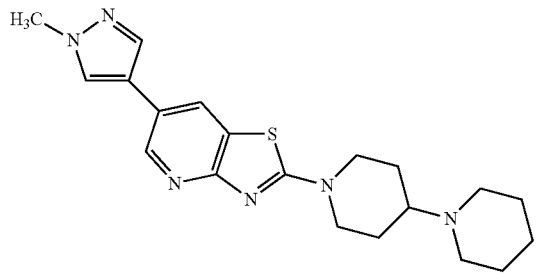
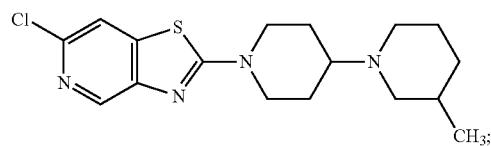
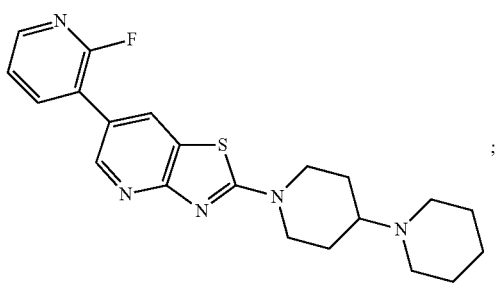
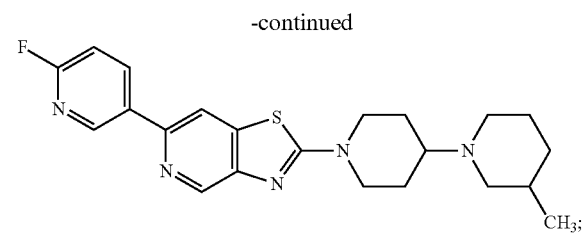
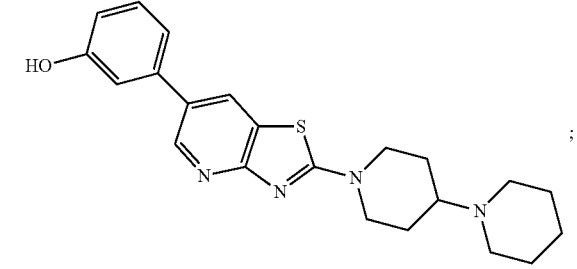
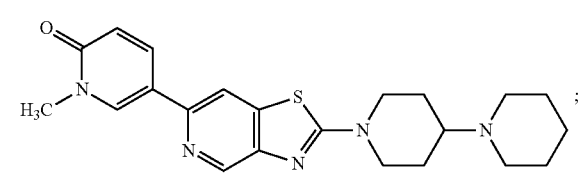
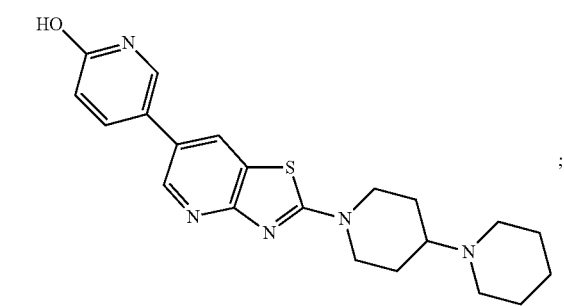
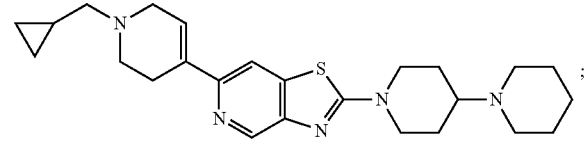
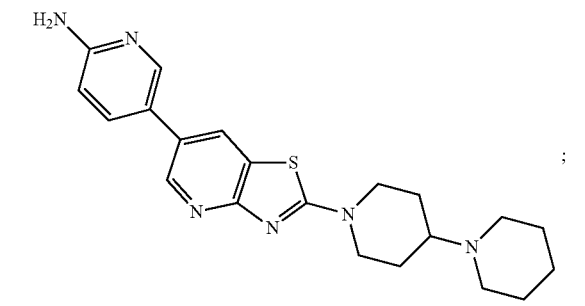
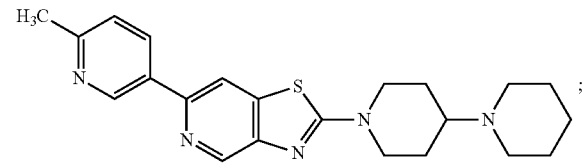

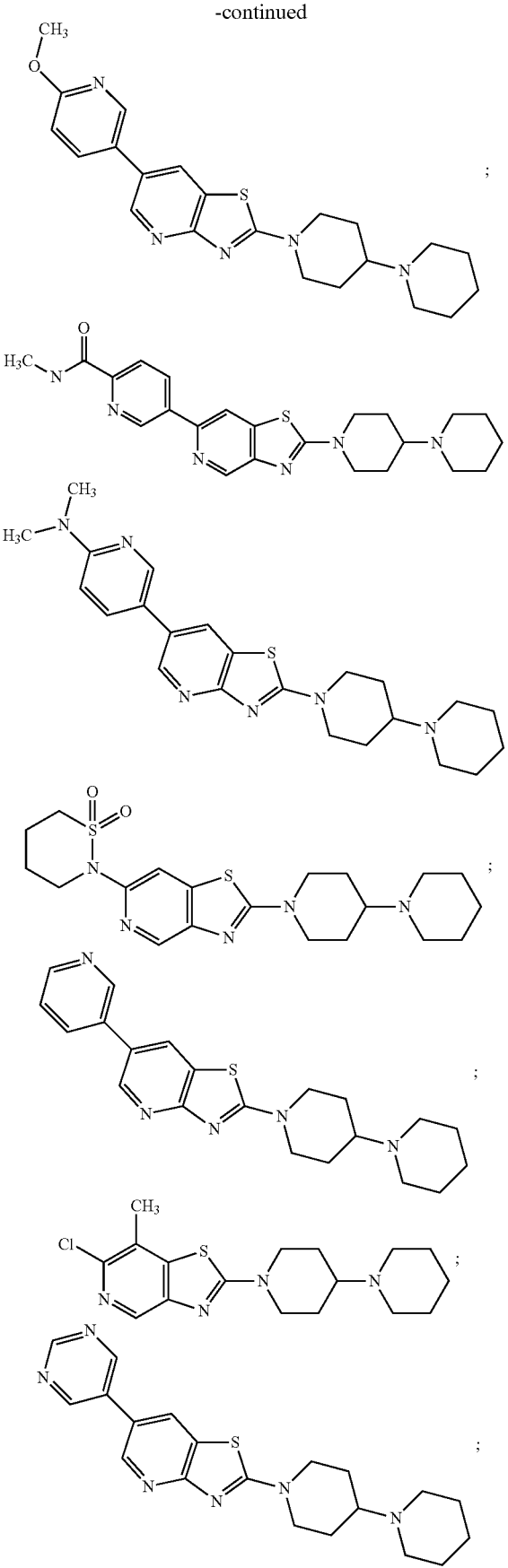
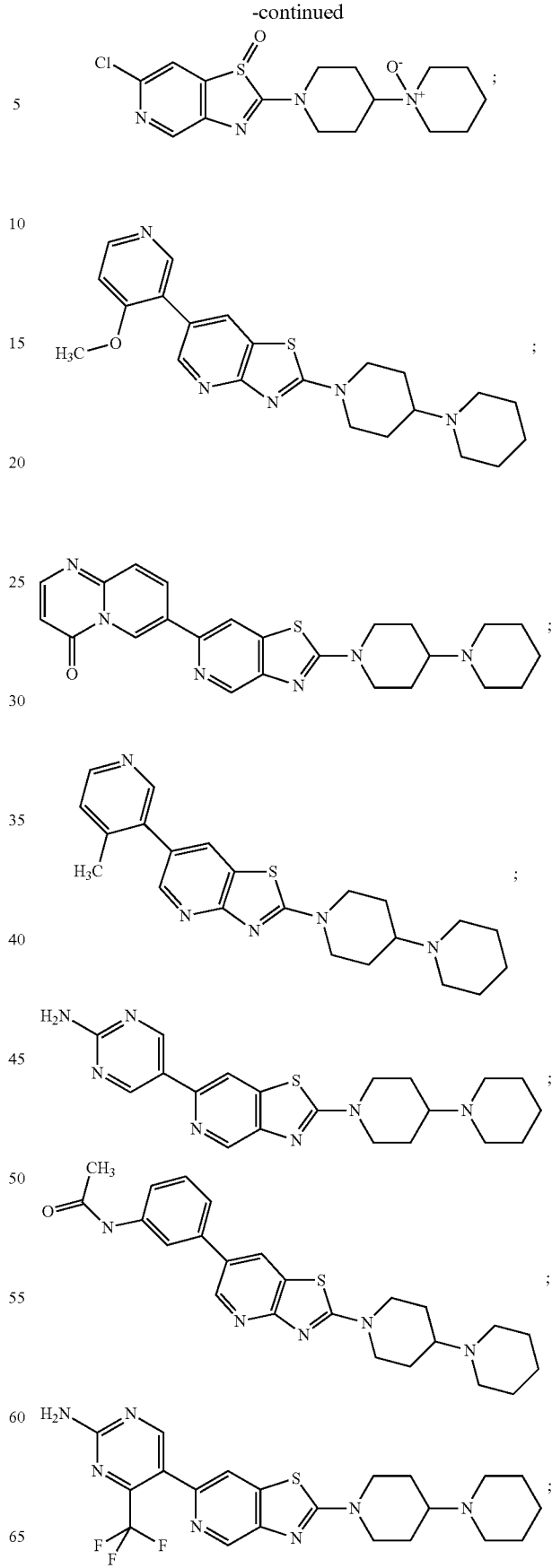

177
-continued
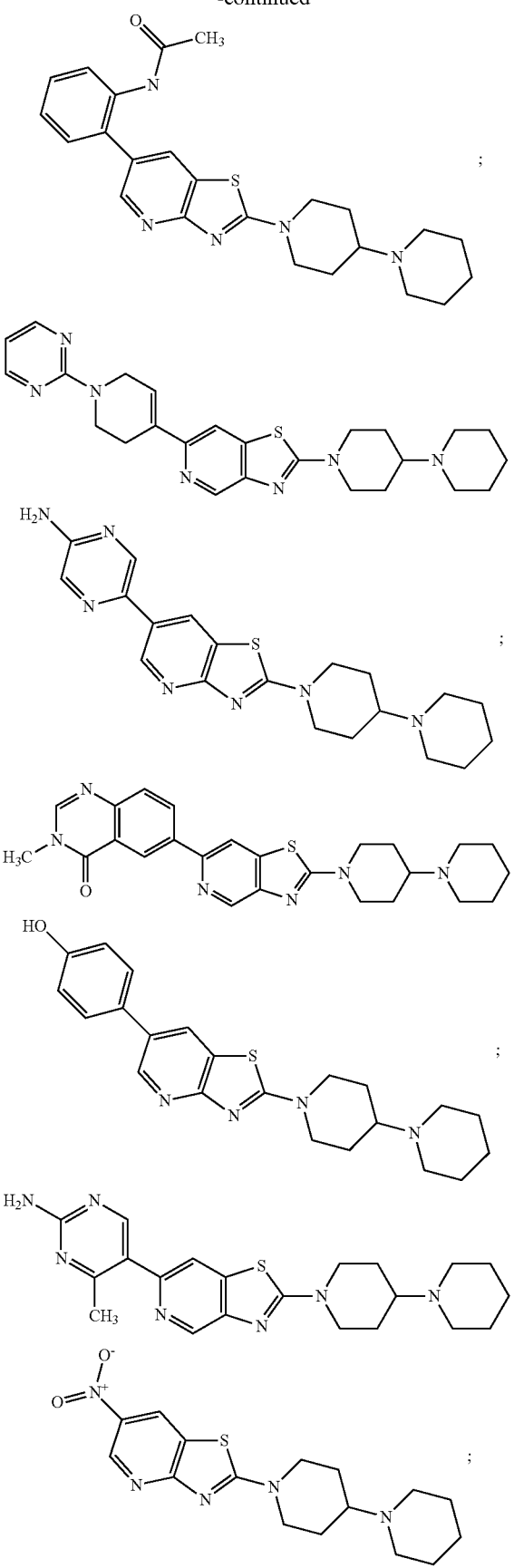
178
-continued
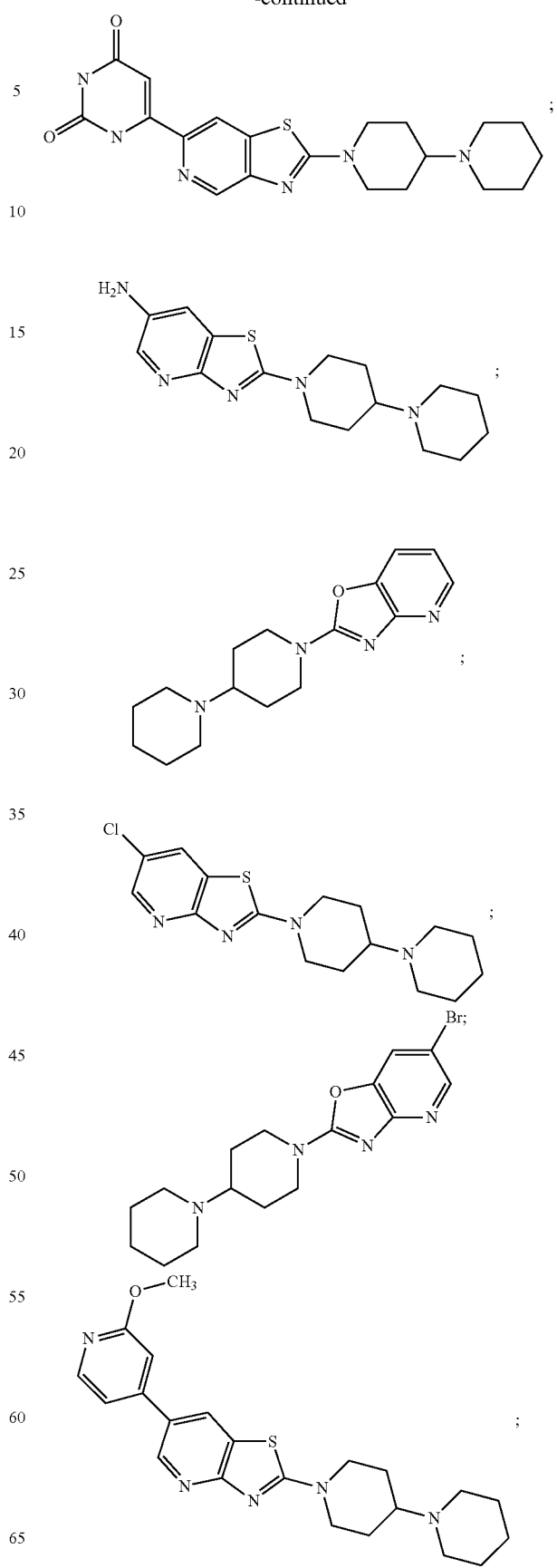

179
-continued
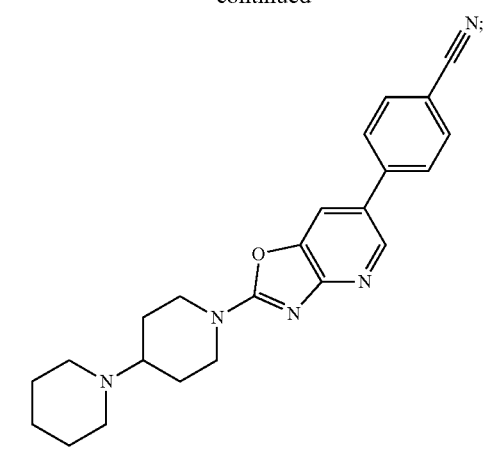
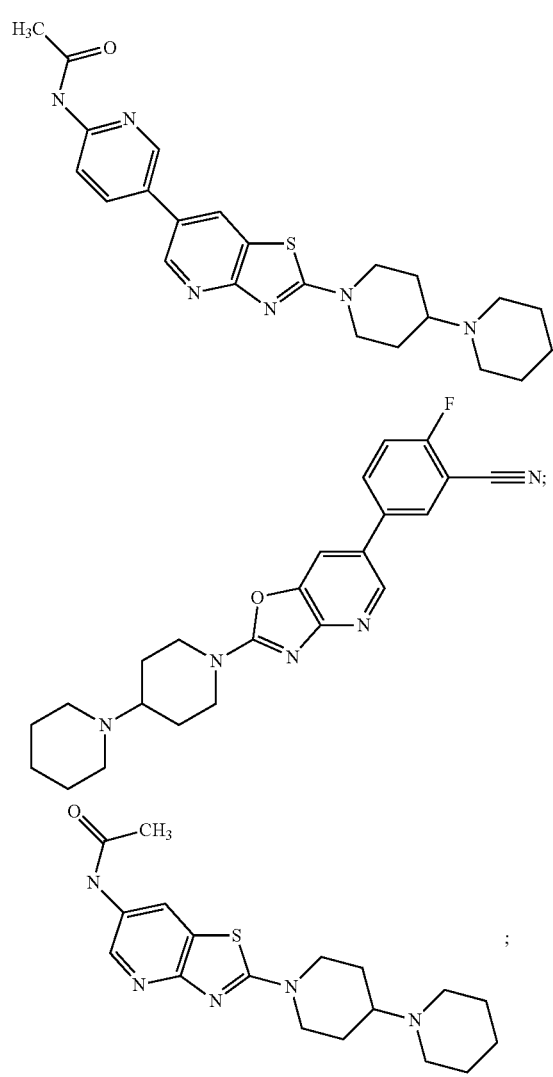
180
-continued
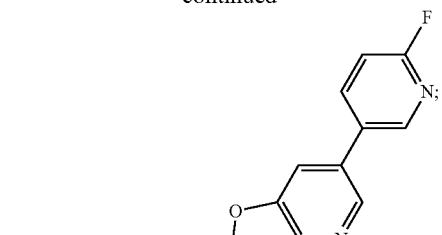
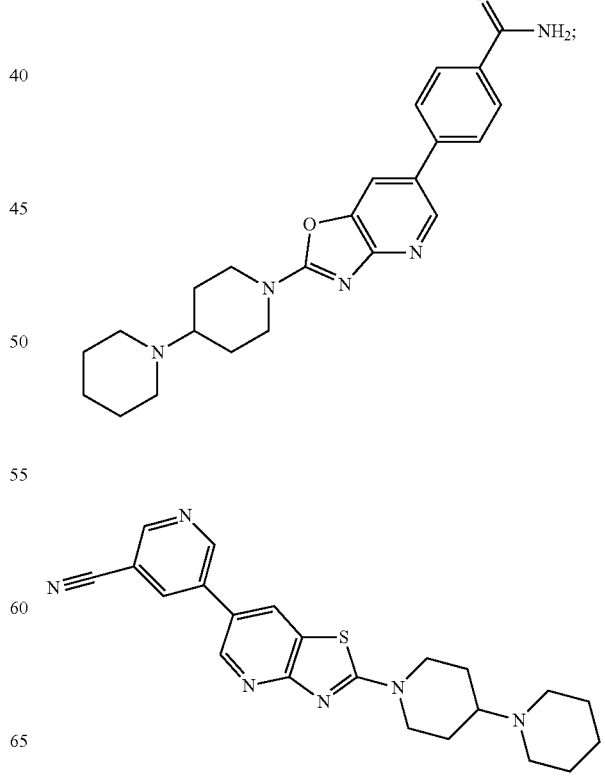

181
-continued
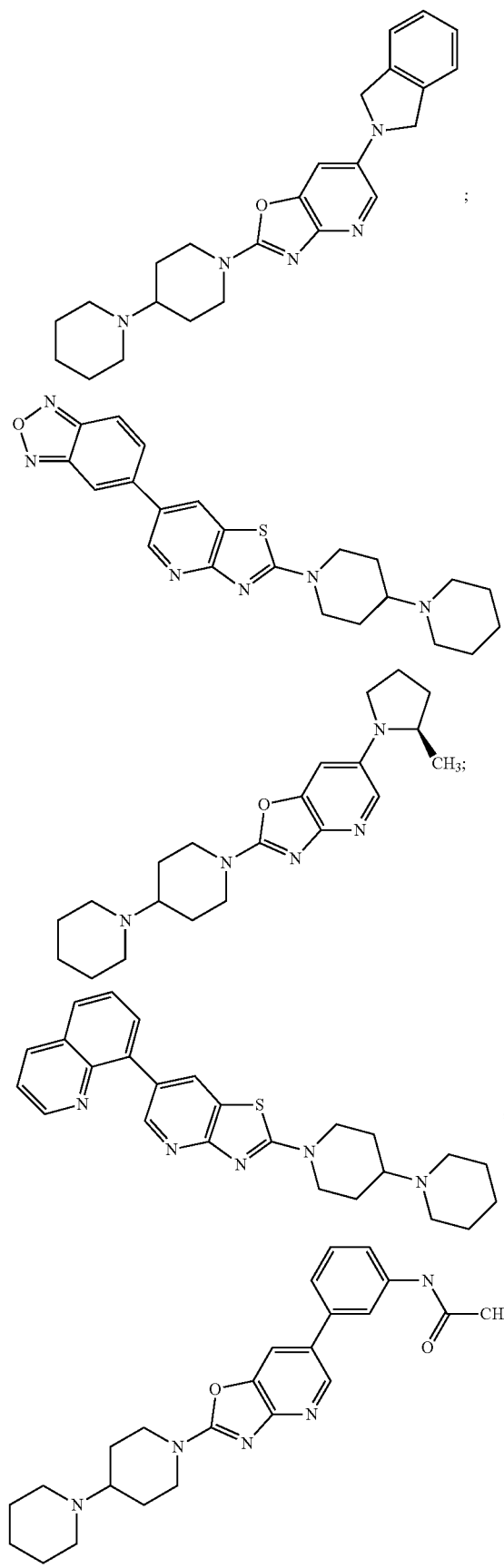
182
-continued
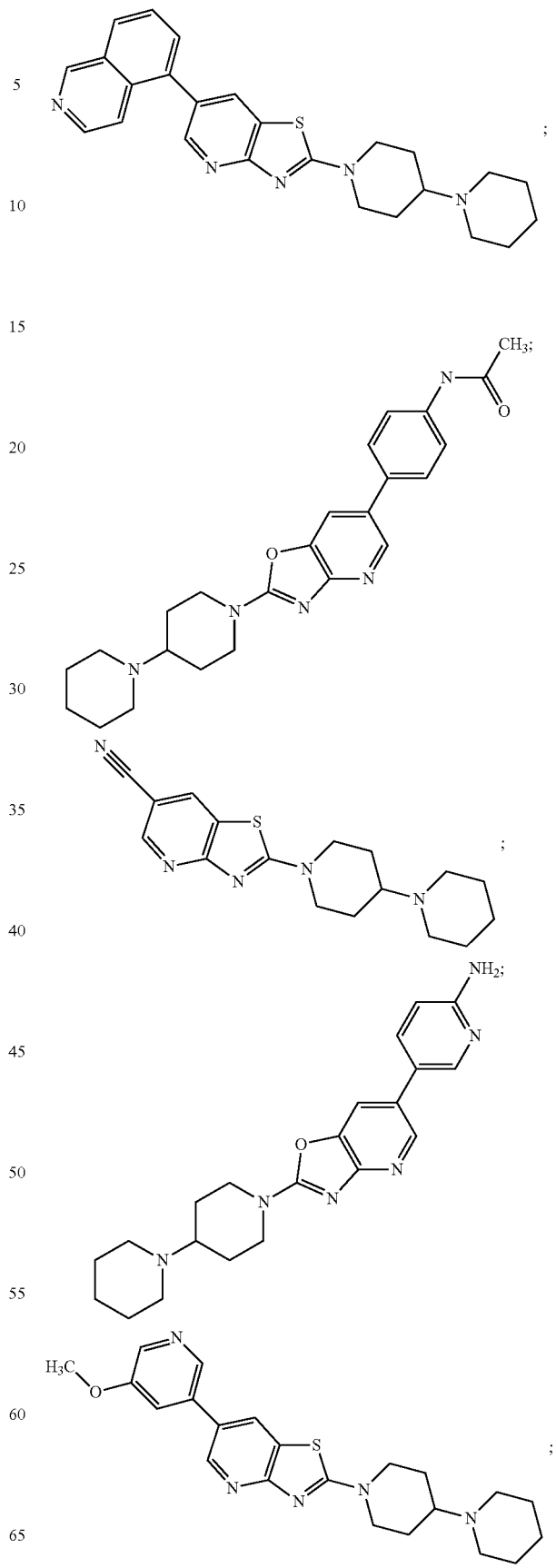

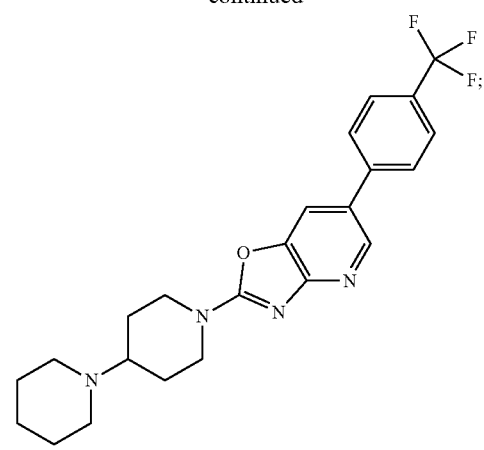
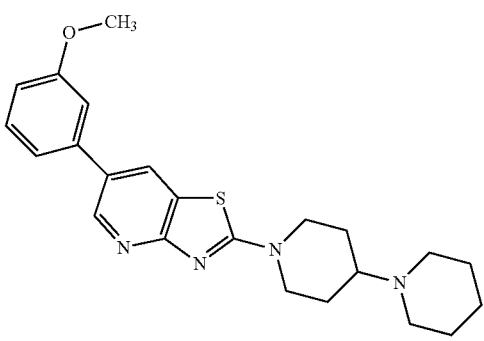
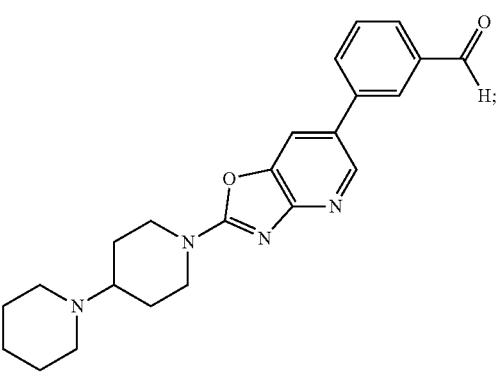
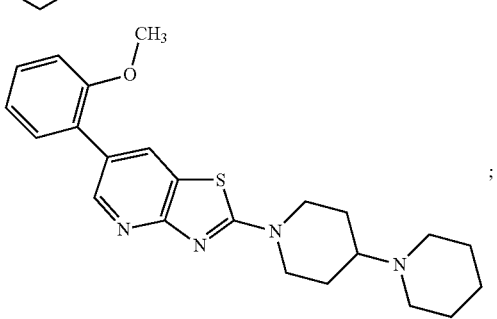
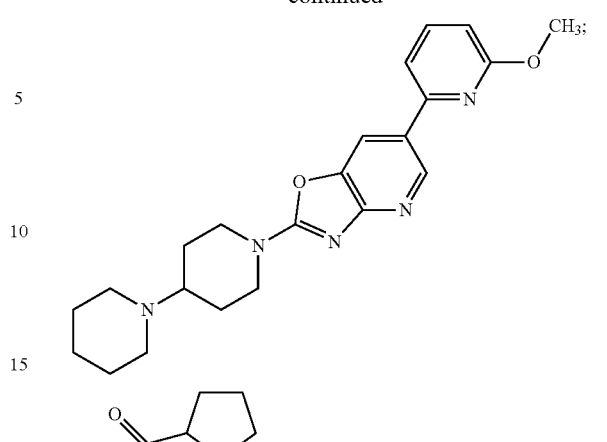
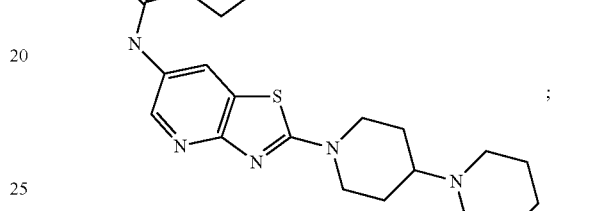
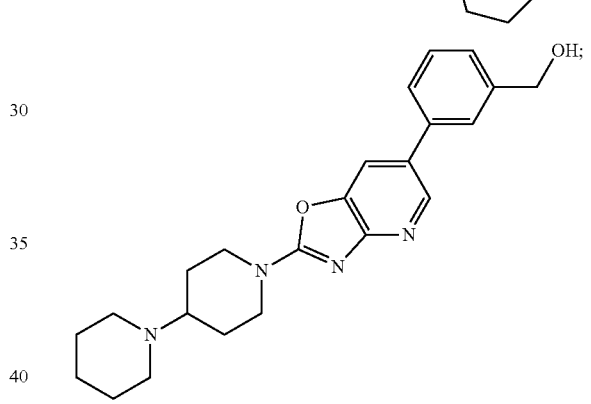
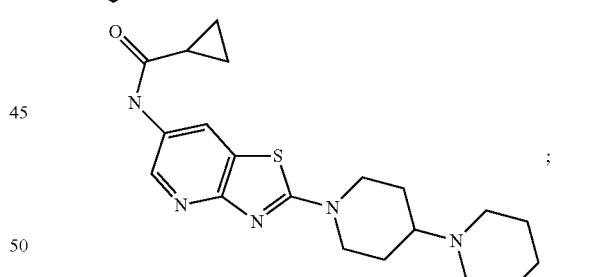
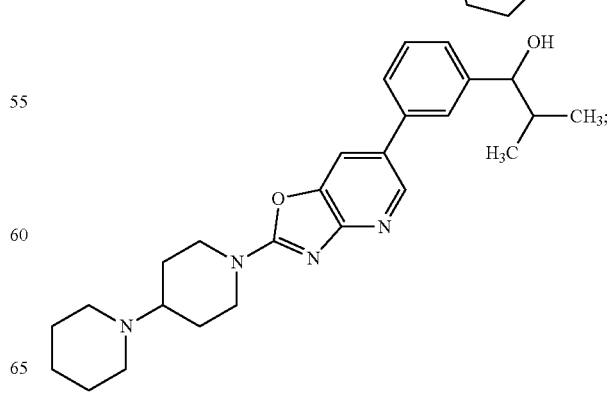

185
-continued
186
-continued
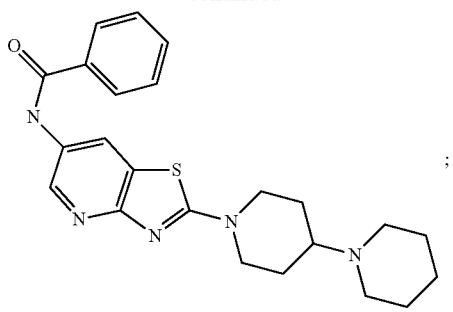
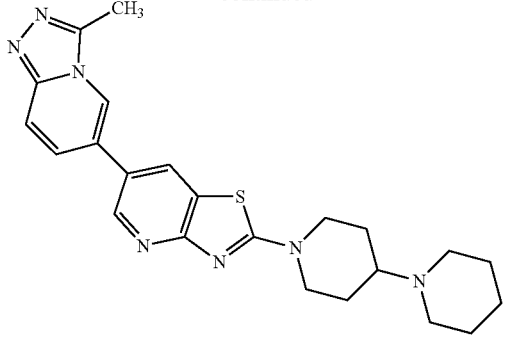
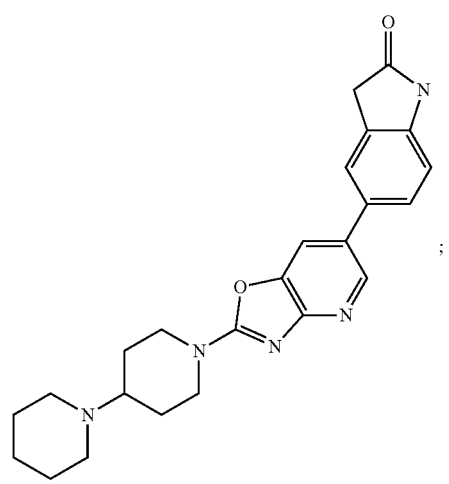
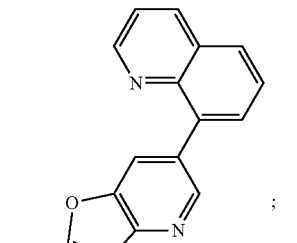
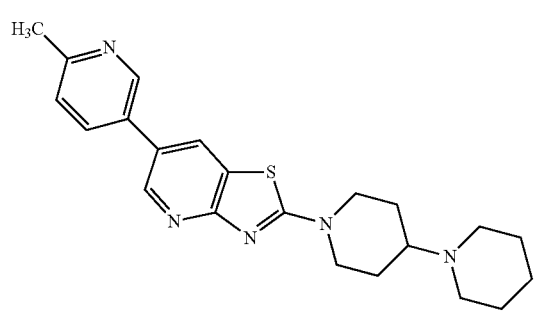
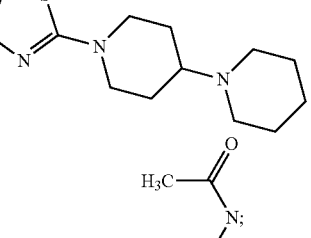
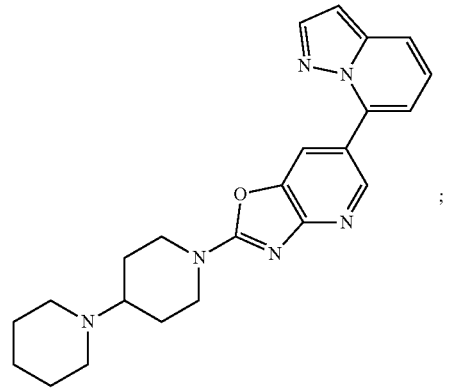
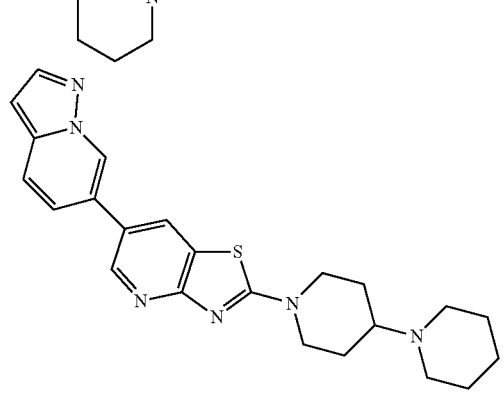

187
-continued
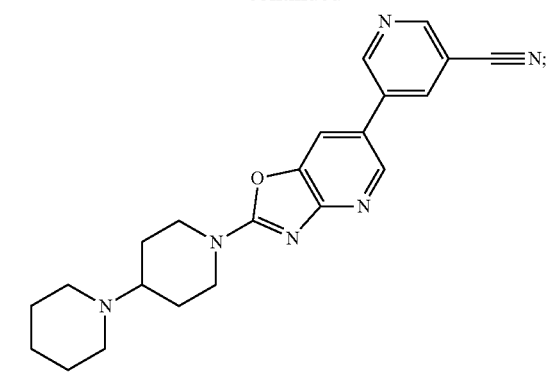
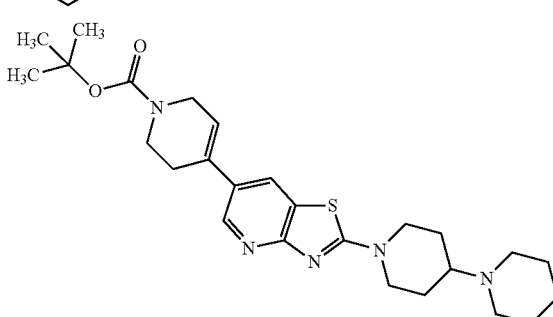
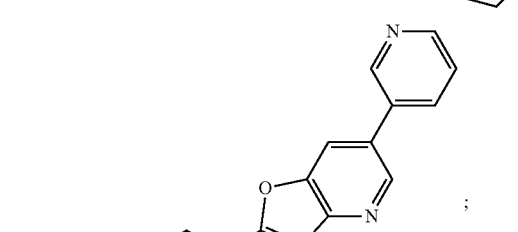
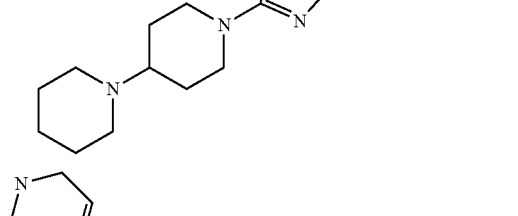
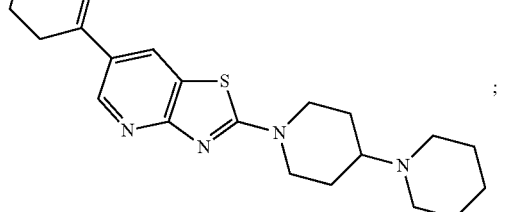
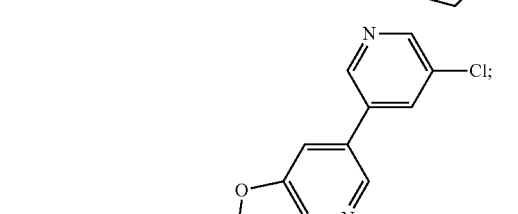
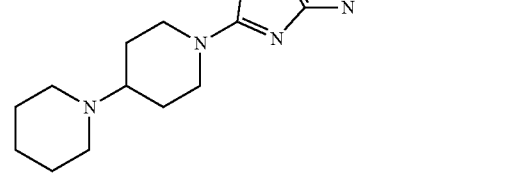
188
-continued
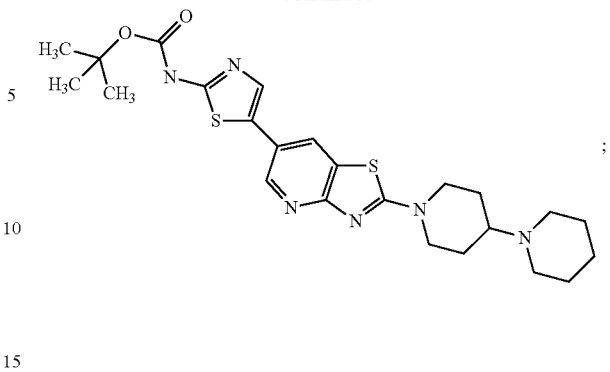
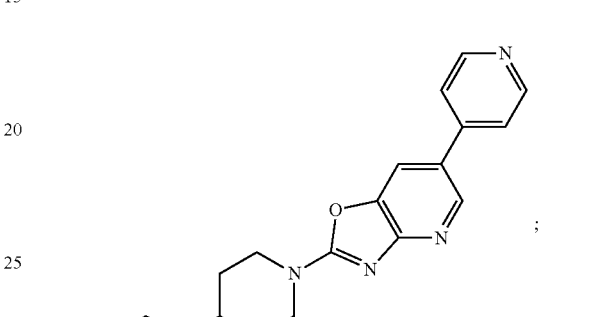
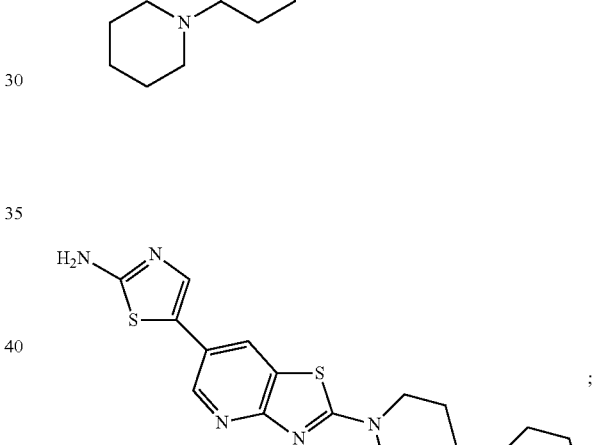
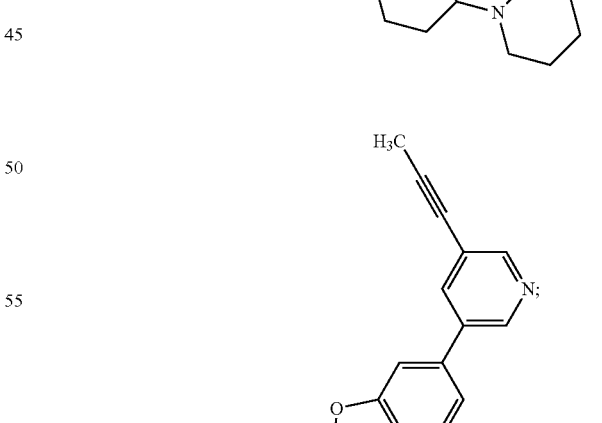
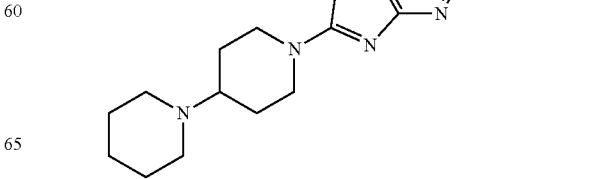

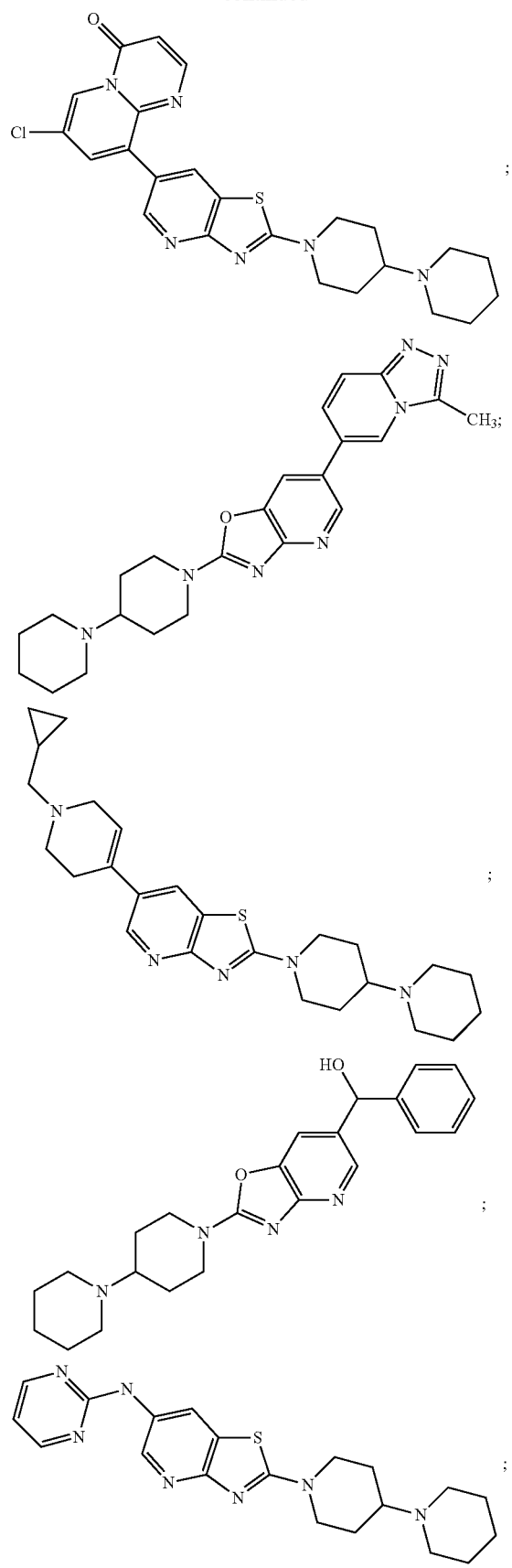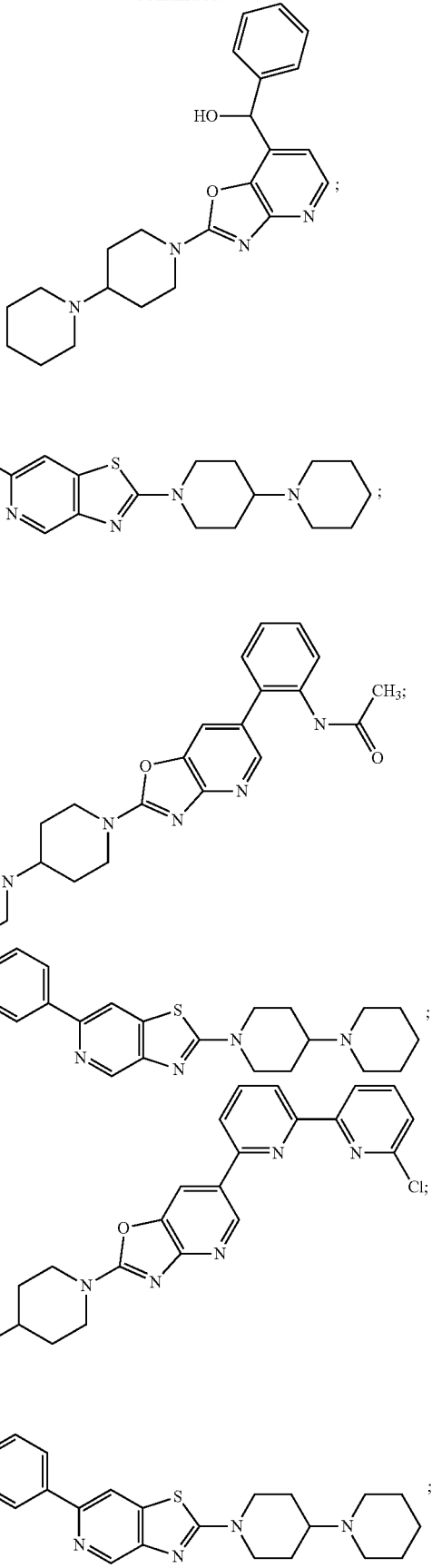

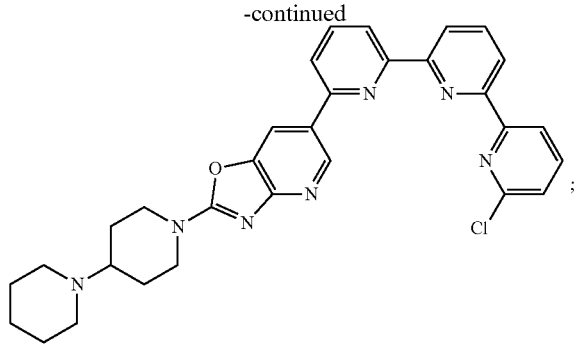
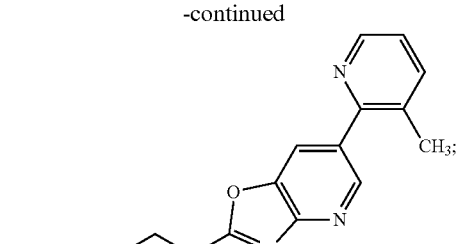
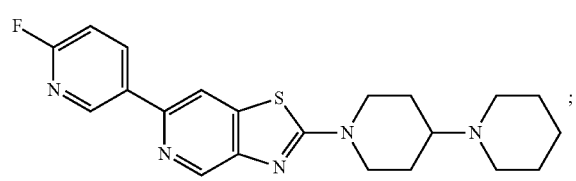
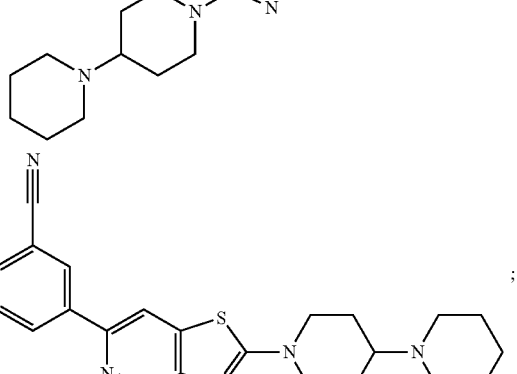
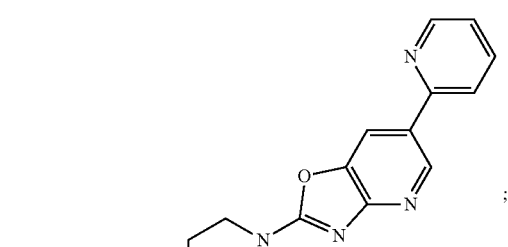
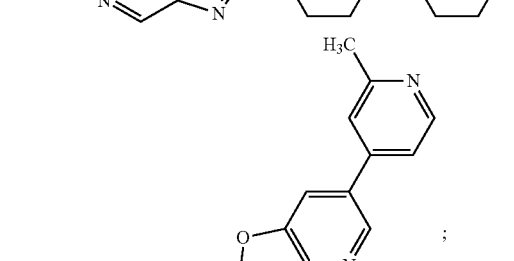
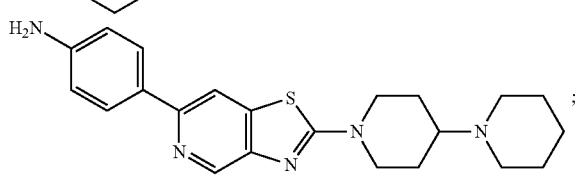
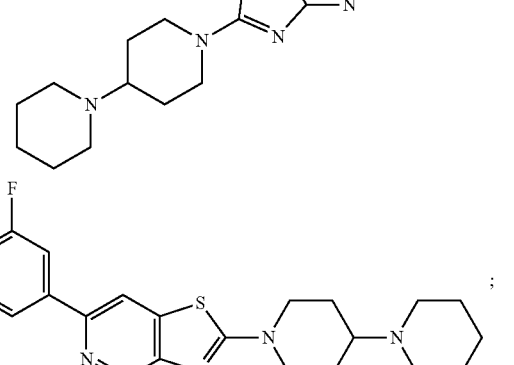
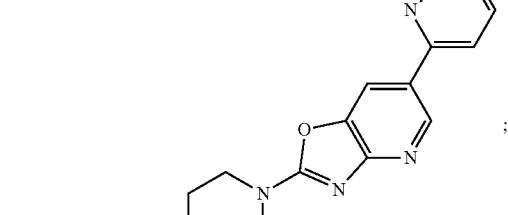
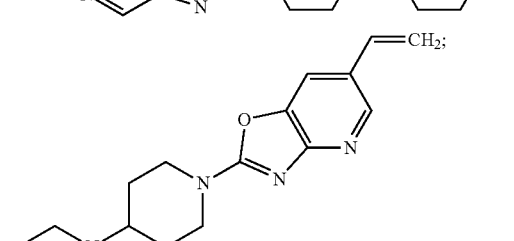
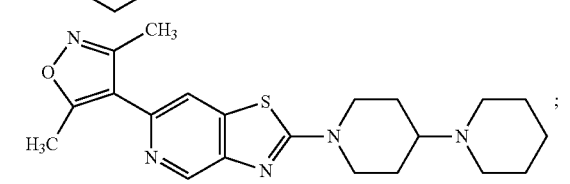
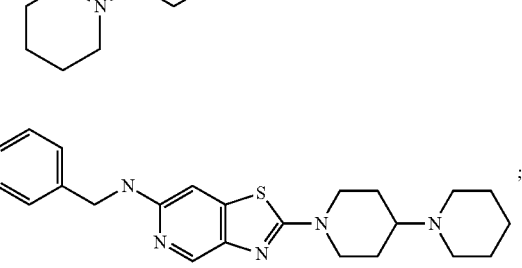

193
-continued
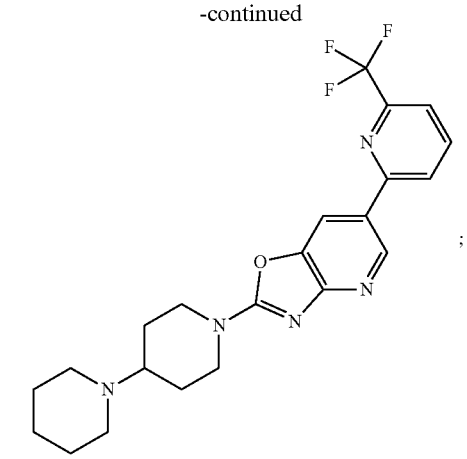
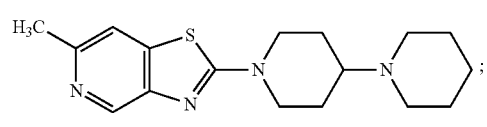
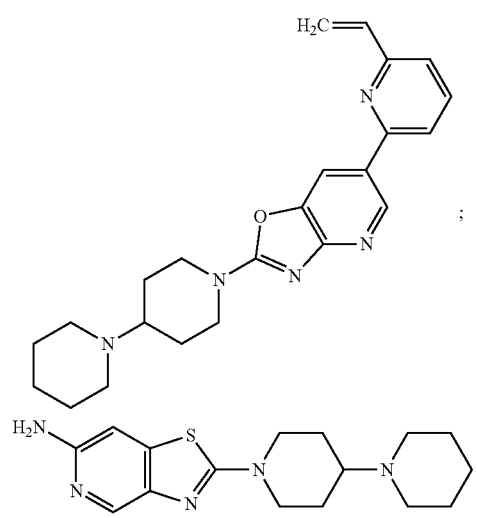
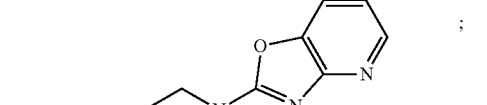
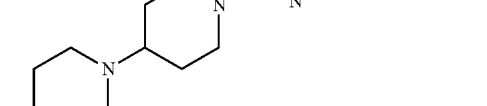
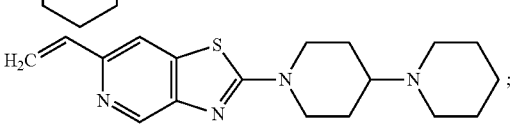
194
-continued
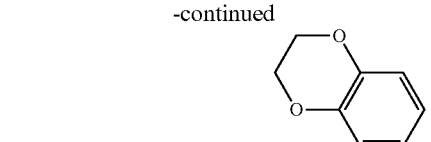
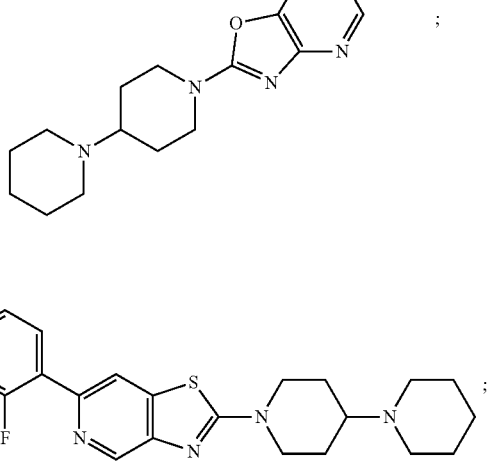
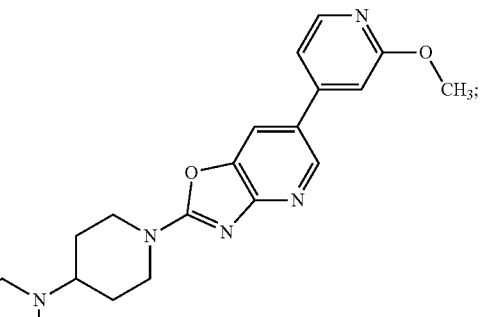
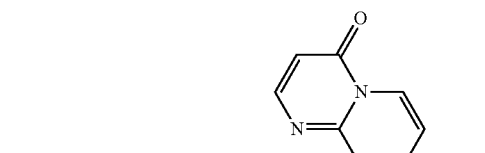
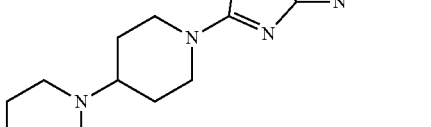
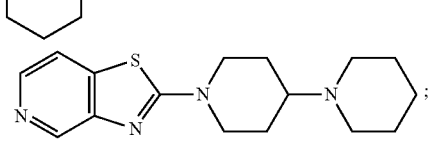

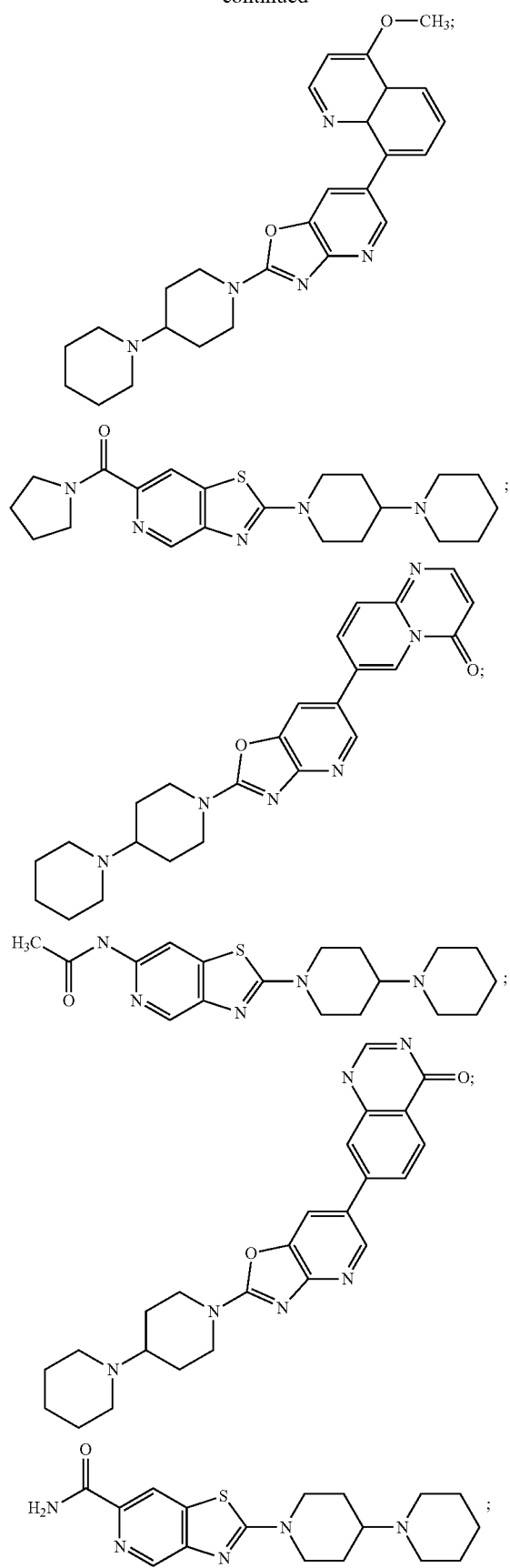
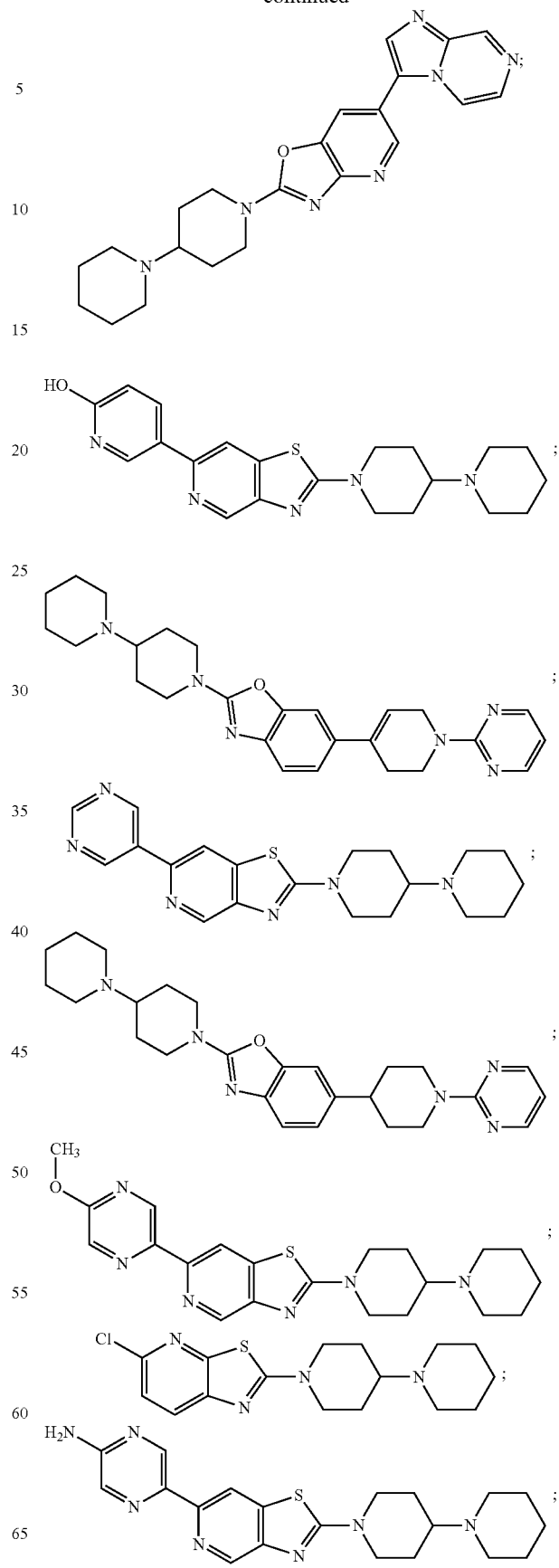

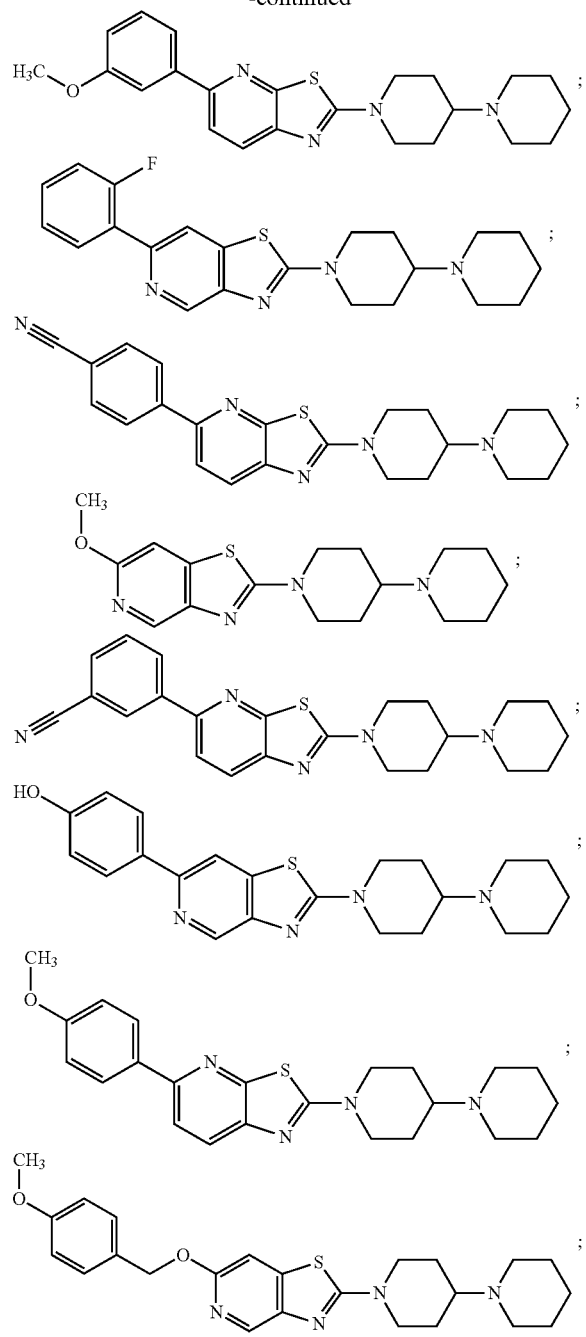
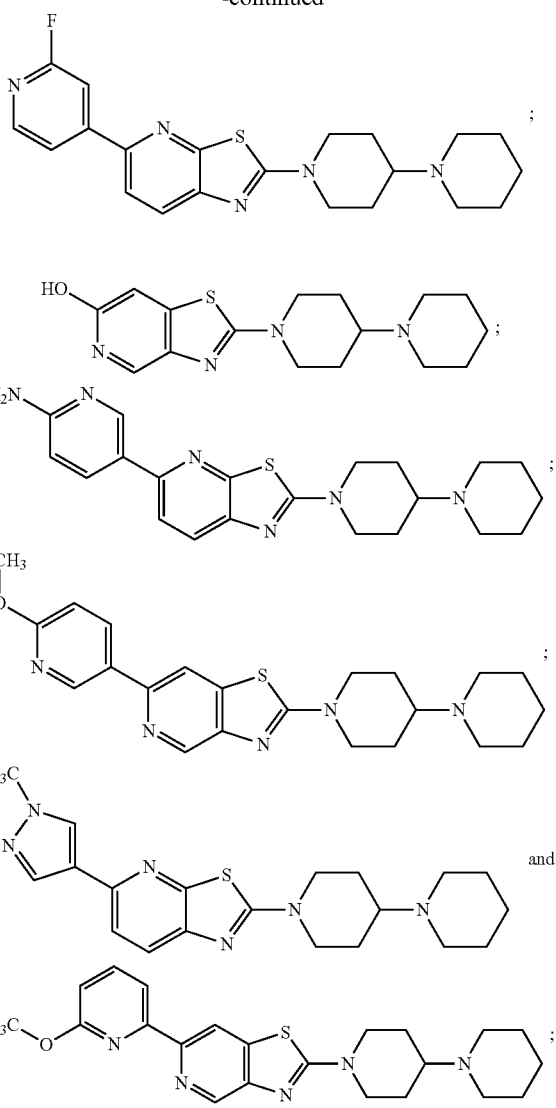
or a pharmaceutically acceptable salt thereof.
2. A pharmaceutical composition comprising the compound of claim 1 or a pharmaceutically acceptable salt thereof, and a pharmaceutically acceptable carrier.
* * * * *